US010201499B2

(12) United States Patent
Bell et al.

(10) Patent No.: US 10,201,499 B2
(45) Date of Patent: Feb. 12, 2019

(54) NANOPARTICLE FORMULATION

(71) Applicant: United Kingdom Research and Innovation, Swindon (GB)

(72) Inventors: Jimmy Bell, London (GB); Elizabeth Louise Thomas, London (GB); Leigh Brody, London (GB); Meliz Sahuri Arisoylu, London (GB); Andrew Miller, London (GB); Gary Frost, London (GB)

(73) Assignee: United Kingdom Research and Innovation, Swindon (GB)

( * ) Notice: Subject to any disclaimer, the term of this patent is extended or adjusted under 35 U.S.C. 154(b) by 280 days.

(21) Appl. No.: 14/424,332

(22) PCT Filed: Aug. 28, 2013

(86) PCT No.: PCT/GB2013/052258
§ 371 (c)(1),
(2) Date: Feb. 26, 2015

(87) PCT Pub. No.: WO2014/033453
PCT Pub. Date: Mar. 6, 2014

(65) Prior Publication Data
US 2015/0224054 A1 Aug. 13, 2015

(30) Foreign Application Priority Data
Aug. 28, 2012 (GB) .................................. 1215289.8

(51) Int. Cl.
*A61K 31/19* (2006.01)
*A61K 9/127* (2006.01)
*A61K 47/24* (2006.01)
*A61K 47/28* (2006.01)

(52) U.S. Cl.
CPC ............ *A61K 9/127* (2013.01); *A61K 9/1271* (2013.01); *A61K 9/1277* (2013.01); *A61K 31/19* (2013.01); *A61K 47/24* (2013.01); *A61K 47/28* (2013.01); *Y10S 977/773* (2013.01); *Y10S 977/906* (2013.01); *Y10S 977/907* (2013.01)

(58) Field of Classification Search
CPC ....................................................... A61K 9/127
See application file for complete search history.

(56) References Cited

U.S. PATENT DOCUMENTS

| 6,146,847 A * | 11/2000 | Goffe ................... A61K 31/131 435/455 |
| 2003/0073615 A1* | 4/2003 | Li ........................ A61K 31/337 514/449 |
| 2004/0161457 A1* | 8/2004 | Gabizon .............. A61K 31/704 424/450 |
| 2005/0019387 A1* | 1/2005 | Rahman ................. A61K 9/127 424/450 |
| 2008/0075763 A1* | 3/2008 | Miller ................. A61K 9/1272 424/450 |
| 2010/0297023 A1 | 11/2010 | Miller et al. |
| 2011/0305769 A1 | 12/2011 | Zhao et al. |

FOREIGN PATENT DOCUMENTS

| JP | 2002-532407 | 10/2002 |
| JP | 2009509531 | 3/2009 |
| WO | WO-2000/35422 | 6/2000 |
| WO | WO-0030620 A1 | 6/2000 |
| WO | WO-0224195 A1 | 3/2002 |
| WO | WO-2006076734 A2 | 7/2006 |
| WO | WO 2006/127977 | 11/2006 |
| WO | WO-2006127977 A1 | 11/2006 |
| WO | WO-2006128888 A1 | 12/2006 |
| WO | 2007041071 | 4/2007 |
| WO | WO 2010056403 A1 * | 5/2010 ........... A61K 9/1272 |

OTHER PUBLICATIONS

SM Berge, LD Bighley, DC Monkhouse. "Pharmaceutical Salts." Journal of Pharmaceutical Sciences, vol. 66 No. 1, Jan. 1977, pp. 1-19. (Year: 1977).*
M Fitzpatrick. "1 M HEPES, pH = 7.0". https://theolb.readthedocs.io/en/latest/buffers/1-m-hepes-ph-70.html accessed Apr. 30, 2018, 2 printed pages. (Year: 2018).*
Anastasovska et al, "Fermentable Carbohydrate Alters Hypothalamic Neuronal Activity and Protects Against the Obesogenic Environment", Obesity, No. 20, 2012, pp. 1016-1023.
Arora et al, "Differential Effects of Two Fermentable Carbohydrates on Central Appetite Regulation and Body Composition", PLoS ONE, vol. 7, Issue 8, e43263, pp. 1-10.
Canani et al, "Potential beneficial effects of butyrate in intestinal and extraintestinal diseases", World of Gastroenterology, No. 17(12), 2011, pp. 1519-1528.
Chambers et al, "Effects of targeted delivery of propionate to the human colon on appetite regulation, body weight maintenance and adiposity in overweight adults", Gut, 2014, pp. 0:1-11.
Chen et al, "Short-Chain Fatty Acid Inhibitors of Histone Deacetylases Promising Anticancer Therapeutics?", Current Cancer Drug Targets, No. 3, 2003, pp. 219-236.
Coradini et al, "Hyaluronan: a suitable carrier for an histone deacetylase inhibitor in the treatment of human solid tumors", Cancer Therapy, vol. 2, 2004, pp. 201-216.
Frost et al, "The short-chain fatty acid acetate reduces appetite via a central homeostatic mechanism", Nature Communications, No. 5:3611, 2014, pp. 1-11.
Hamer et al, "Review Article: the role of butyrate on colonic function", Alimentary Pharmacology & Therapeutics, No. 27, 2008, pp. 104-119.

(Continued)

Primary Examiner — Isaac Shomer
(74) Attorney, Agent, or Firm — Norton Rose Fulbright US LLP

(57) ABSTRACT

The present invention concerns nanoparticle formulations suitable for the delivery of one or more therapeutic agents, the formulations comprising: a cationic cholesterol derivative; a neutral phospholipid; cholesterol or a neutral cholesterol derivative; and a saturated fatty acid, PEGylated neutral derivative of phosphatidylethanolamine or phosphatidylcholine.

12 Claims, 38 Drawing Sheets

(56) References Cited

OTHER PUBLICATIONS

Figure 1:
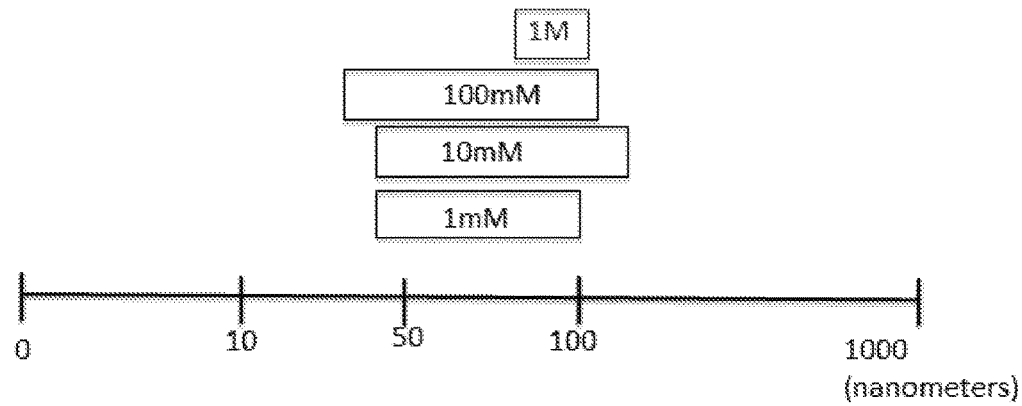

Kamaly et al: "Folate receptor targeted bimodal liposomes for tumor magnetic resonance imaging", Bioconjugate Chemistry, Apr. 15, 2009, vol. 20, No. 4, pp. 648-655, ACS, Washington, DC.

Kamaly et al: "Bimodal paramagnetic and fluorescent liposomes for cellular and tumor magnetic resonance imaging", Bioconjugate Chemistry, Jan. 16, 2008, vol. 19, No. 1, pp. 118-129, ACS, Washington, DC.

Lasic, "Novel applications of liposomes", Trends in Biotechnology, Jul. 1, 1998, vol. 16, No. 7, pp. 307-321, Elsevier Publications, Cambridge, GB.

Office Action issued in Chinese Application No. 201380055336.1, dated Apr. 21, 2017 (English translation. provided).

Yamashita et al., "Improvement of Obesity and Glucose Tolerance by Acetate in Type 2 Diabetic Otsuka Long-Evans Tokushima Fatty (OLETF) Rats," *Biosci. Biotechnol. Biochem.*, 2007; 71(5): 1236-1243.

Kritchevsky, David, et al; "Dietary Fiber—Chemistry, Physiology, and Health Effects"; SpringerLink.com; Proceeding of the George Vahouny Fiber Conference; 1990, pp. 317-318.

Office Action issued in Japanese Application No. 2002-532407, dated Oct. 3, 2017 (and English translation provided).

New Cosmetics Handbook, 2006, 710-712 (no English-language version available).

Fragrance Journal, 1996, 24(9), 70-78 (no English-language version available).

Office Action of corresponding Japanese Patent Application No. 529120/2015, dated May 18, 2018, in Japanese.

Office Action of corresponding Japanese Patent Application No. 529120/2015, dated May 18, 2018, English translation.

\* cited by examiner

D

E (a)

(b)

NANOPARTICLE FORMULATION

CROSS REFERENCE TO RELATED APPLICATIONS

This application is a national phase application under 35 U.S.C. § 371 that claims priority to International Application No. PCT/GB2013/052258 filed on Aug. 28, 2013, designating the United States, which claims the benefit of priority to Great Britain Patent Application No. 1215289.8 filed Aug. 28, 2012, all of which are incorporated herein by reference in their entirety.

The present invention relates to nanoparticle formulations. In particular, though not exclusively, it concerns the nanoparticle-assisted delivery of therapeutic agents for the treatment of metabolic and oncogenic diseases.

Cellular metabolic deregulation is a central premise in the development of many chronic diseases including cancer. Recently, there has been renewed interest in the potential of metabolic engineering, through the use of small molecules, to achieve metabolic re-transformation of abnormal cells and tissues. However, making sufficient and sustained metabolic impact through such methods can be difficult, since suitable small molecules need to be identified and an appropriate mode of delivery developed.

Metabolic engineering provides a powerful and effective tool, because it allows for the systematic manipulation and fine-tuning of cellular metabolic activities. A means of re-engineering the metabolism of the deregulated or oncogenic state is desirable. Such a means could have particular application in the prophylaxis or treatment of obesity, a range of cancers, and any related conditions associated with metabolic disequilibrium.

Obesity is a global health concern and is associated with a number of co-morbidities, including type 2 diabetes, hypertension, and cardiovascular disease, as well as representing an independent risk factor for the development of a number of cancer types. The social and economic burden of increasing obesity rates worldwide means there is an urgent demand for interventional therapeutic strategies.

The liver, in particular, plays a fundamental role in controlling the body's metabolism. Extensive epidemiological studies have demonstrated that an obesogenic state is linked to the development of non-alcoholic steatohepatitis (NASH), hepatic fibrosis, cirrhosis, and most notably hepatocellular carcinoma (HCC), one of the most lethal cancers, with a 5 year survival rate of only 4-8%. Studies indicate that liver dysfunction may occur following surplus calorific intake as a result of excess hepatic triglyceride synthesis, which in turn leads to an over-accumulation of lipid in the parenchymal liver cells. This accumulation of fat may also be accompanied by a progressive state of inflammation, steatohepatitis, which is thought to mediate the development of HCC.

Currently, the most effective treatments for tackling obesity focus on improvements in diet and regular exercise. Dietary patterns suggested involve fruit, vegetables and whole grains, due to the ample amounts of fibre and water that dilutes the metabolisable energy content per volume of food. Previous studies indicate that diets high in dietary fibres, which are a major determinant of energy density, have beneficial effects on symptoms of metabolic syndrome, including a reduction in bodyweight, total body fat and blood glucose levels. Estimates also suggest that dietary fibre intake has declined significantly in most developed countries, and the predominant dietary fibre type has changed from highly fermentable carbohydrates obtained from nuts, seeds and tubers to low fermentable cereal grain fibres.

In particular, increased intake of fermentable carbohydrates in rodents has been shown to lead to an increase in large bowel short-chain fatty acids production, decreased bodyweight and improved insulin sensitivity. A number of human trials have also suggested that fermentable carbohydrates may aid appetite suppression and weight loss.

Although the mechanisms behind fermentable carbohydrate-mediated changes in appetite remain largely unknown, one hypothesis points towards short-chain fatty acids (the end product of carbohydrate fermentation in the colon) increasing the circulating concentrations of anorexigenic hormones. However, in humans it has been difficult to consistently demonstrate that the suppression of appetite as a result of increased intake of fermentable carbohydrates is linked to an increase in circulating anorexigenic hormones.

In fact, the present inventors have found that an anorexigenic effect obtained by chronic elevations in short-chain fatty acid concentrations, induced through diets rich in fermentable carbohydrates, or via direct administration (e.g. intraperitoneal injection), may not only be the result of an increase in anorexigenic hormones, but rather a direct effect on the central nervous system. One problem associated with the therapeutic use of short-chain fatty acids, however, relates to the fact that they are readily metabolised by colonocytes and the liver, with very low concentrations reaching the peripheral circulation. It is therefore difficult to administer such compounds in a concentration that is non-toxic and which will provide a beneficial therapeutic effect.

Short-chain fatty acids such as butyrate are already known to be produced by intestinal microbial fermentation of mainly undigested dietary carbohydrates, and are known to exhibit possible therapeutic effects. For example, butyrate is known to act as an inhibitor of histone deacetylases (HDAC) and thus has the ability to impose cell cycle arrest, differentiation and/or apoptosis in many tumour cell types (Chen et al. *Curr Cancer Drug Targets,* 2003, 3 (3), 219-36). In addition, it has been shown to reduce the growth of colon carcinoma cells and to induce apoptosis in the same, thereby finding utility in the treatment of metabolic syndromes (Canini et al. *World J Gastroenterol* 2011, 17 (12), 1519-28).

However, butyrate in particular has not been used in vivo with much success because it has a very short half life. As such, a high concentration is required to be administered in order to elicit a beneficial effect. Accordingly, previous studies have focused on providing the means to deliver butyrate in a controlled manner.

For example, Coradini et al. *Cancer Therapy* 2004, 2, 201-16 have described the use of hyaluronan as a suitable carrier for HDAC inhibitors such as butyrate in the treatment of human solid tumours. Hamer et al. *Aliment Pharmacol Ther* 2008, 27, 104-119 have described the effect of butyrate on colonic function and summarised the delivery of butyrate by tablets coated with a slow release pH-dependent coating, the consumption of butyrate-producing probiotic bacteria, prodrugs comprising butyrate derivatives (such as tributyrin), and the employment of rectal enemas for delivering butyrate to the distal colon.

Other examples of strategies for delivering short-chain fatty acids include those described in WO2006/127977, which details the use of specific sugar-butyrate hybrid molecules as prodrug-like small molecules. WO2006/07634 describes a prodrug-based approach for delivering short chain fatty acids by means of their attachment to amino acids, e.g. serine. WO2006/128888 describes solid lipid nanoparticles comprising covalently-linked cholesterol-propionate/butyrate derivatives for slow release of the respective short-chain fatty acids. Furthermore, WO2002/024195 relates to alkoxylated acyl glycerine as a carrier containing short-chain fatty acids as the alkoxy unit, and which are useful for the treatment of gastrointestinal disorders such as colitis. However, none of these prior art examples is capable of delivering such therapeutic agents to the target organ of choice, in their native form, for effective release and distribution to the required sites of interest.

Accordingly, it is an object of the present invention to provide nanoparticle formulations which are suitable to facilitate the long-term delivery of therapeutic agents to the central nervous system.

In one aspect of the invention there is provided a nanoparticle formulation suitable for the delivery of one or more therapeutic agents, the formulation comprising (i) a cationic cholesterol derivative, (ii) a neutral phospholipid, (iii) cholesterol or a neutral cholesterol derivative, and (iv) a saturated fatty acid, PEGylated, neutral derivative of phosphatidylethanolamine or phosphatidylcholine.

By specific design of the lipid-based nanoparticles of the invention, controlled delivery of a therapeutic agent to target organs may be achieved. In the case of short-chain fatty acids, this has the potential to lead to positive effects on hepatic cellular lipids levels, decreased body fat retention, and a reduction in the rate of related cancer growth.

As used herein, the term "neutral" refers to an entity that resides in an uncharged or neutral zwitterionic form at a selected pH. The term "cationic" refers to an entity that resides in a positively charged form at a selected pH. A suitable pH may, for example, be 7.4+/−0.5.

The term "phospholipid" refers to a lipid comprising a hydrophilic head group comprising a phosphate group, usually negatively charged, and a hydrophobic tail group. Suitable examples include lipids based on: phosphatidic acid (phosphatidate) (PA); phosphatidylethanolamine (cephalin) (PE); phosphatidylcholine (lecithin) (PC); phosphatidylserine (PS); phosphatidylinositol (PI); phosphatidylinositol phosphate (PIP); phosphatidylinositol bisphosphate (PIP2); phosphatidylinositol triphosphate (PIP3); ceramide phosphorylcholine (Sphingomyelin) (SPH); ceramide phosphorylethanolamine (Sphingomyelin) (Cer-PE); and ceramide phosphorylglycerol.

The term "short-chain fatty acid" refers to aliphatic carboxylic acids composed of 1 to 6 carbon atoms, which may be linear or branched. Suitable short-chain fatty acids include: formic acid; acetic acid; propionic acid; butyric (butanoic) acid; isobutyric (2-methylbutanoic) acid; valeric (pentanoic) acid; isovaleric (3-methylbutanoic); and caproic (hexanoic) acid and analogues including halogenated derivatives, such as dichloroacetate (DCA). The term "fatty acid", on the other hand, refers to linear or branched, saturated or unsaturated carboxylic acids or derivatives thereof comprising a carbon chain of $C_{7-24}$. Typically, saturated fatty acids comprise a carbon chain of $C_{12-24}$.

The term "nanoparticle" refers to small particles which behave as a whole unit in terms of their transport and properties, and which typically exhibit an average particle size diameter (determined, for example, by a light scattering technique) in the range of 1 to 500 nm (preferably 1 to 250 nm). The term "ultrafine particles" may be used synonymously with the term "nanoparticles". A liposome is an exemplary type of nanoparticle which may be considered as an artificially-prepared vesicle composed of a lipid bilayer.

The term "PEGylated" refers to an entity, typically a polymer- or lipid-based entity, which is covalently attached to a polyethylene glycol (PEG) polymer chain. The PEG chain is derived from a molecular formula of $C_{2n}H_{4n+2}O_{n+1}$ and has a molecular mass of less than 20,000 g/mole.

The formulation may further comprise one or more therapeutic agents which are to be delivered by means of the nanoparticles. Due to the physical nature and composition of the nanoparticles, the therapeutic agent(s) can be delivered to the anatomical location of interest where the agents are subsequently released. The release may be directly inside the cell or organ of interest or initially to the surrounding tissue, and then to other locations of the body, such as the brain, via the circulatory system.

Such therapeutic agents may be associated with the nanoparticles by means of chemical attachment, i.e. covalent linkage, to the surface of the particle, by incorporation within the physical structure of the particle, or by encapsulation within an internal volume of the particle. For example, in a preferred embodiment, the nanoparticle is a liposome, such as a cationic liposome, whereby the liposome may be substantially spheroidal and comprises one or more lipid bilayer membranes. In this embodiment, the one or more therapeutic agents may be contained within an encapsulated aqueous volume, or a hydrophobic interior structure of the liposome. One advantage of using liposome technology in this way is that it is possible to target certain tissues, e.g. liver, with controlled release of the therapeutic agent(s), thus increasing the amount of circulating agent and aiding its delivery more consistently over a longer period of time.

When the therapeutic agent(s) are encapsulated within the nanoparticle, or liposome, the concentration of the encapsulated therapeutic agent(s) may be in the range of 0.1 to 100 mM, preferably 0.5 to 15 mM, more preferably 1 to 10 mM. In a particularly preferred embodiment, the encapsulated concentration is in the range of 1 to 7 mM.

One group of therapeutic agents which are particularly suitable for use in the formulation of the present invention are short-chain fatty acids. Such short-chain fatty acids include, for example, acetic acid, propionic acid, butyric acid and/or valeric acid. Short-chain fatty acid receptors (e.g. $FFAR_2$ and $FFAR_3$) are found widely throughout the human body and therefore represent ideal targets for the treatment of diabetes and obesity, and associated cancers.

In particular, acetate, propionate, and butyrate are favoured from a therapeutic point of view, due to their favourable toxicological profile in humans compared to other small molecule therapeutics. Furthermore, the present inventors have found that acetate is especially efficacious in terms of its propensity to be encapsulated within the nanoparticle formulation of the invention, its stability within the formulation itself and its evident positive effects on appetite suppression, body fat retention, and growth suppression of related cancers. Biodistribution studies have shown that there is a major uptake by liver, heart, kidney and muscle tissues of liposomes of the claimed formulation.

The size of the nanoparticles has not been found to be a limiting factor. However, from a practical point of view the average size (by diameter, measured for example by means of a light scattering technique) of the nanoparticles may be in the range of 1 to 500 nm, preferably 10 to 300 nm, more preferably 20 to 250 nm. More specifically, it will be appreciated that in terms of the physical formation of such nanoparticles and their encapsulation of therapeutic agents, nanoparticles with an average size of 30 to 200 nm are preferable, particularly from 40 to 120 nm. Nanoparticles in the size range of 40 to 120 nm are more easily formed and exhibit a greater level of stability with regard to storage and administration. The average size of the nanoparticles in the Examples described herein was measured with a Zetasizer Nano ZS90 (Malvern Instruments, Ltd., UK) using a dynamic light scattering principle for particle size and electrophoretic light scattering for zeta potential.

When the one or more therapeutic agents are encapsulated within the nanoparticles, it is advantageous that the concentration of agent encapsulated is in the range of 0.1 to 100 mM, preferably 0.1 to 50 mM, 0.1 to 25 mM, or 0.5 to 15 mM. More preferably, the concentration of encapsulated agent is in the range of 1 to 10 mM, since this gives rise to a more stable nanoparticle and allows for an appropriate quantity of agent in order to elicit the required biological effects. The concentration of encapsulated agent may be determined using nuclear magnetic resonance spectroscopy. In the Examples described herein, $^1$H NMR spectra were acquired on a Bruker Biospin scanner (Bruker, USA) with a 5 mm inverse mode BBI probe at the following parameters: 500.13 MHz, sweep width 12 ppm (6009 Hz), data points 32 k, acquisition time 2.726 seconds, relaxation delay 3 seconds (overall recycle delay 5.726 seconds), pulse width 6 µs (corresponding to a 55 degree pulse), 64 averages and temperature of 298K. MestRe-C software was used to analyse the acquired spectra. The free induction decay (FID) signal was apodized to reduce noise and fourier transformed. Baseline correction was carried out using a spline function and peaks were integrated for relative quantification. The concentration of encapsulated agent was determined relative to a reference peak of lactate at 1.3 ppm.

The formulation of the invention comprises a cationic cholesterol derivative. Such a derivative may comprise a cholesterol-based hydrocarbon framework as a head group linked to a polar organic tail group, such as a polyamine hydrocarbon chain. Although the head group may be any framework based on the common cholesterol structure, cholesterol is particularly preferred and may be linked to the tail group via the 3-hydroxyl group. Suitable specific cationic cholesterol derivatives include 4-aza-N$^1$-cholesteryloxycarbonyl-1,7-heptanediamine (ACH), N$^1$-cholesteryloxy-carbonyl-3,7-diaza-1,9-nonanediame (CDAN), N$^{10}$-cholesteryloxycarbonyl-4,8,13-triaza-1,16-hexadecanediamine (CTAH), N$^1$-cholesteryloxy-carbonyl-4,9-diaza-1,12-dodecanediamine (CDAD), and N$^{15}$-cholesteryloxycarbonyl-3,7,12-triaza-1,15-pentadecanediamine (CTAP). Turning to the structure of the tail group, a polyamine appendage is preferred based on the following formula: H$_2$N(CH$_2$)$_x$NH(CH$_2$)$_y$NH(CH$_2$)$_z$NHC(O)—, wherein x is 1 to 10, y is 1 to 10, and z is 1 to 10. In this embodiment, x is preferably 1 to 4, y is preferably 1 to 4, and z is preferably 1 to 4. It is believed that this cholesterol-based cationic lipid increases the uptake of the nanoparticle into hepatocytes. In addition, it helps ensure that any therapeutic agents remain encapsulated. In an embodiment, the cationic cholesterol derivative is N$^1$-cholesteryloxy-carbonyl-3,7-diaza-1,9-nonanediame (CDAN).

The formulation of the invention also comprises a neutral phospholipid. Suitable neutral phospholipids for inclusion in the formulation include phosphatidylethanolamines, such as dioleoyl phosphatidylethanolamine (DOPE), palmitoyloleoylphosphatidylethanolamine (POPE), and distearoylphosphatidylethanolamine (DSPE); phosphatidylcholines, such as dioleoylphosphatidylcholine (DOPC), dipalmitoylphosphatidylcholine (DPPC), palmitoyloleoylphosphatidylcholine (POPC), and distearoylphosphatidylcholine (DSPC); phosphatidylglycerol; phosphatidylglycerols, such as dioleoylphosphatidylglycerol (DOPG), dipalmitoylphosphatidylglycerol (DPPG), and distearoylphosphatidylglycerol (DSPG); phosphatidylserines, such as dioleoyl- or dipalmitoylphosphatidylserine; and diphosphatidylglycerols. The neutral phospholipid may be a saturated neutral phospholipid, preferably a phosphatidylcholine or phosphatidylethanolamine lipid. When the neutral phospholipid is a phosphatidylcholine or phosphatidylethanolamine lipid, the lipid preferably comprises fatty acid chains of $C_{7-24}$, more preferably $C_{8-22}$, most preferably $C_{10-20}$. In particular, a phosphatidylcholine lipid comprising a fatty acid chain of $C_{10-20}$ is preferred. When the fatty acid chain of such lipids is in the range of $C_{10-20}$, it is believed that a more stable nanoparticle is formed. Most preferably, the neutral phospholipid is distearoylphosphatidylcholine (DSPC).

The formulation of the invention also comprises cholesterol (IUPAC name: (3β)-cholest-5-en-3-ol) or a neutral cholesterol derivative. The neutral cholesterol derivative may comprise a cholesterol-based hydrocarbon framework which may be covalently attached to a hydrocarbon-based chain by means of the 3-hydroxyl group, for example by an ester linkage. Suitable such derivatives include: cholesteryl acetate; cholesteryl butyrate, cholesteryl valerate; cholesteryl caprylate; cholesteryl dodecanoate; cholesteryl oleate; cholesteryl heptadecanoate; cholesteryl stearate; cholesteryl linoleate; cholesteryl linolelaidate; cholesteryl palmitate; cholesteryl palmitelaidate; cholesteryl myristate; cholesteryl behenate; cholesteryl erucate; cholesteryl arachidonate; cholesteryl 10-undecenoate; and cholesteryl phenylacetate. It is believed that this component provides the nanoparticles with a level of rigidity which allows them to store the associated therapeutic agent(s) until the desired point of delivery, at which time the nanoparticle is able to disperse the active contents. Most preferably, the formulation comprises cholesterol, since this component affords a favourable balance of strength and dispersion, with a beneficial toxicological profile in humans.

The formulation of the invention also comprises a saturated fatty acid PEGylated neutral derivative of phosphatidylethanolamine or phosphatidylcholine. The phosphatidylethanolamine or phosphatidylcholine derivatives may comprise saturated fatty acid chains of $C_{10-24}$, preferably $C_{12-20}$. Suitable derivatives of phosphatidylethanolamines include dioleoyl phosphatidylethanolamine (DOPE), palmitoyloleoylphosphatidylethanolamine (POPE), and distearoylphosphatidylethanolamine (DSPE), and suitable derivatives of phosphatidylcholine include dioleoylphosphatidylcholine (DOPC), dipalmitoylphosphatidylcholine (DPPC), palmitoyloleoylphosphatidylcholine (POPC), and distearoylphosphatidylcholine (DSPC). Most preferably, the derivative is distearoylphosphatidylcholine (DSPC) or distearoylphosphatidylethanolamine (DSPE). With regard to the PEG component, the neutral phosphatidylethanolamine or phosphatidylcholine derivative may be covalently attached to a polyethylene glycol chain, which is indicative as to their average molecular weights. For example a PEG chain with n=9 would have an average molecular weight of approximately 400 daltons and would be identified as PEG400. The PEG chain can be in the range of 550 to 5000, preferable 1200 to 3000, and even more preferably 1500 to 2500. Most preferably, the PEG chain has an average molecular weight of approximately 2000.

The nanoparticle formulation may also comprise fluorescent phospholipids as visualisation tools. Exemplary lipids include 1,2-dioleoyl-sn-glycero-3-phosphoethanolamine-N-(5-dimethylamino-1-naphthalenesulfonyl, 1,2-dioleoyl-sn-glycero-3-phosphoethanolamine-N-(1-pyrenesulfonyl), 1,2-dioleoyl-sn-glycero-3-phosphoethanolamine-N-(carboxyfluorescein), 1-oleoyl-2-[6-[(7-nitro-2-1,3-benzoxadiazol-4-yl)amino]hexanoyl]-sn-glycero-3- phospho-L-Serine, {25-1N-[(7-nitrobenz-2-oxa-1,3-diazol-4-yl)-methyl]amino}-27-norcholesterol, oleoyl-2-[6-[(7-nitro-2-1,3-benzoxadiazol-4-yl)amino]hexanoyl]-sn-glycero-3-phosphoethanolamine and 1,2-dioleoyl-sn-glycero-3-phosphoethanolamine-N-(Lissamine Rhodamine B Sulfonyl). A preferred fluorescent lipid is 1,2-dioleoyl-sn-glycero-3-phosphoethanolamine-N-(Lissamine Rhodamine B Sulfonyl).

Typically, the nanoparticles of the invention have a size of 150 nm or less, or 100 nm or less. By carefully nanoengineering, nanoparticle formation may be controlled such that their size remains below 150 nm, preferably 100 nm. This size range is considered optimal for the accumulation of nanoparticles in solid tumours due to the characteristics of tumour tissue. Tumour tissue is considered to possess a universal affinity for macromolecular agents, termed the enhanced permeation and retention effect (EPR), whereby macromolecular agents accumulate in tumour tissue. It is believed that tumour properties such as increased angiogenesis, a heterogeneous and destructive vascular infrastructure, impaired lymphatic drainage and a "leaky" endothelial layer are all factors that contribute to the accumulation of macromolecular structures within tumour tissue.

Accordingly, in a further embodiment of the present invention, the nanoparticle formulation may further comprise a tumour targeting agent. Nanoparticles of the present invention comprising a tumour targeting agent typically comprise a ligand for a receptor that is over-expressed in tumour cells relative to the expression of said receptors in the cells of non-tumourous tissue of mammals.

One example of such a tumour targeting agent is one which comprises a folate moiety. In preferred examples of the present invention, the tumour targeting agent is a phospholipid-polyethylene glycol-folate compound. More preferably the phospholipid-polyethylene glycol-folate compound is DSPE-PEG(2000)-Folate [distearoylphosphatidylethanolamine-polyethylene glycol (2000)-folate].

Typically, the amount of the folate moiety present in the nanoparticle formulation is 1-2 mol % of the total formulation, exclusive of any incorporated therapeutic agent(s). When the nanoparticle is a liposome, the amount of the folate moiety present in the liposome is generally 1-2 mol % of the total liposome formulation.

As an example of a tumour targeting agent, folate is a good example of such a targeting moiety; as folate-based targeting systems present an effective means of selectively delivering therapeutic or imaging agents to tumours. It is known that aggressive or undifferentiated tumours at an advanced stage have an increased folate receptor (FR) density, indicating that cancer therapy could benefit from the broad approach that FR mediated drug delivery offers. The FR is over-expressed in several cancer types, such as brain, kidney, lung and breast cancers and in particular, in epithelial carcinomas such as ovarian cancers. The FR ligand, folate (or folic acid), is a vitamin that is used for the biosynthesis of nucleotides and is utilized in high levels to meet the needs of proliferating cancer cells.

In addition to numerous drug delivery efforts, folate-targeted technology has been successfully applied to radio-imaging of therapeutic agents, fluorescence imaging of cancer cells, MRI contrast agents, and gadolinium liposomes. Nanoparticles, particularly liposomes, are able to accumulate within tumour tissue due to the widely reported enhanced permeation and retention effect (EPR) which relies on the passive accumulation of colloidal macromolecules of ~40 kDa and above in tumours. The EPR effect arises due to aberrant tumour endothelium, which as a result of its "leakiness" allows the penetration of nanoparticles into tumour tissue. Liposome accumulation in tumour tissue could be improved through the use of receptor targeting moieties that are either post-conjugated to the surface of liposomes, or are attached to lipids that become incorporated within the liposomal bilayer. Since FR binding affinity (Kd=1×1$^{-10}$ M (1×10$^{-1}$ M)) does not appear to be affected when its ligand, folate is conjugated to an imaging agent or therapeutic moiety via its γ-carboxyl, a folate ligand tethered onto the distal end of a lipidic PEG amphiphile allows for the development of a FR targeted liposomal system.

In addition, further lipids for improving magnetic resonance imaging and nuclear magnetic resonance imaging may be included. Illustrative examples include Gd-DTPA-bis(stearylamide) (Gd-B SA); Gd-DTPA-bis(myrisitylamide) (GdDTPA-BMA); 1,2-dimyristoyl-sn-glycero-3-phosphoethanolaminediethylene-triaminepentaacetate: Gd3+ (DMPEDTPA:Gd3+); D35-1.2-dihexanoyl-sn-glycero-3-phosphocholine; gadolinium (III) 2-{4,7-bis-carboxymethyl-10-[(N,N-distearylamidomethyl-N"-amido-methyl]-1,4,7,10-tetra-azacyclododec-1-yl}-acetic acid (Gd.DOTA.DSA); gadolinium (III) 1,4,7,10-tetraazacyclododecane-1,4,7,10-tetraacetic acid mono(N1-Cholesteryloxy-3-carbonyl-1,2-diaminoethane)amide (Gd.DOTA.Chol); gadolinium (III) 1,4,7,10-tetraazacyclododecane-1,4,7,10-tetraacetic acid mono(N1-distearoylphosphatidylethanolamine)amide (Gd.DOTA.DSPE) and gadolinium (III) diethylenetriamine-1,1,4,7,10-penta(acetic acid)-10-acetic acid mono(N1-cholesteryloxy-3-carbonyl-1,2-diaminoethane)amide (Gd.DTPA.Chol).

The composition of the nanoparticle formulation in terms of molar ratio with respect to components (i) to (iv) may, in embodiments, satisfy the following ranges: (i) 10 to 50; (ii) 10 to 50; (iii) 20 to 70; and (iv) 1 to 20. More preferably, the molar ratio of (i) to (iv) satisfies the following ranges: (i) 20 to 40; (ii) 20 to 40; (iii) 25 to 55; and (iv) 1 to 10. In a particularly preferred embodiment, the molar ratio of (i) to (iv) satisfies the following ranges: (i) 30 to 35; (ii) 30 to 35; (iii) 30 to 35; and (iv) 1 to 5.

The nanoparticle formulation of the invention may potentially be used to deliver a wide variety of therapeutic agents, and as such has widespread utility for preparing medicaments. In particular, the formulation exhibits advantageous efficacy when used, in association with appropriate therapeutic agents, in the prophylaxis or treatment of obesity or cancer. In a preferred aspect, the nanoparticle formulation comprises liposomes encapsulating short-chain fatty acids, most preferably acetate, which are effective when used in the prophylaxis or treatment of obesity or cancer. Specific forms of cancer which may be mitigated by the use of the claimed nanoparticle formulations include liver cancer, such as hepatocellular carcinoma, cholangiocarcinoma and hemangioendotheliomas, colon cancer, and renal cancer, such as renal cell carcinoma and urothelial cell carcinoma. Other conditions which may be alleviated or treated using the claimed technology include metabolic syndrome, ulcerative colitis, Crohn's disease, type 2 diabetes, hypertension, cardiovascular disease, hypercholesterolaemia, epilepsy and stroke (including post-stroke neurological damage).

In a related aspect of the invention, there is provided a pharmaceutical composition comprising a nanoparticle formulation according to the invention, and one or more pharmaceutically acceptable excipients. Such a pharmaceutical composition may be used as a medicament, in particular for use in the prophylaxis or treatment of obesity or cancer as noted above. In addition, the pharmaceutical composition may be employed in the prevention or treatment of any of the conditions noted above.

In another aspect of the invention, there is provided a method of preparing a nanoparticle formulation as defined above, the method comprising: providing a solution of (i) to (iv) in an organic solvent, and evaporating the solvent to obtain a thin-film of a mixture of (i) to (iv); rehydrating the thin-film with a defined volume of a polar solution, optionally containing one or more therapeutic agents; agitating the polar solution so as to cause the formation of a dispersion of the mixture of (i) to (iv) and the one or more optional therapeutic agents in the polar solution; optionally buffering the dispersion to a pH of approximately 7; and optionally purifying the dispersion by filtration.

Typically, the components (i) to (iv) are combined in their respective molar ratios identified above. They may be combined in any organic solvent, although dichloromethane ($CH_2Cl_2$), chloroform ($CHCl_3$), dimethylformamide, toluene, acetone, and ethyl acetate are preferred. In particular, an aprotic organic solvent such as acetone, dichloromethane or chloroform may be employed. Chloroform is highly preferred from a solubility perspective.

Rehydration of the thin-film produced initially may be achieved with a polar solution optionally containing one or more therapeutic agents. The polar solution is typically a protic solvent such as water, ethanol, and methanol, or the polarity of the solution may be increased by the presence of a polar compound solubilised therein. For example, an aqueous solution comprising an acidic species, such as 4-(2-hydroxyehtyl)-1-piperizineethanesulfonic acid (HEPES), acetic acid, propionic acid, or butyric acid. When the one or more therapeutic agents is a short-chain fatty acid, the polar solvent is preferably an aqueous solution comprising one or more short-chain fatty acids, most preferably acetic acid.

The concentration of the one or more therapeutic agents in the polar solution used for rehydrating the thin-film is preferably in the range of 1 mM to 10 M, more preferably 50 mM to 2 M, most preferably 75 mM to 1.5 M. For example, preferably the concentration of the one or more therapeutic agents is approximately 1 M.

The formulation may be agitated by stirring, shaking or sonicating the nanoparticle components in the polar solution. From a practical point of view, sonication of the required components is preferred because it produces a more evenly dispersed mixture of the nanoparticles in the polar solution. For example, as in the Examples herein, sonication may be achieved using an MXB Series Ultrasonic water bath (Grant Instruments, UK) for one hour on the highest setting at 30° C. After agitation and buffering, the nanoparticle mixture is preferably purified by dialysis filtration, using membrane or dynamic dialysis, such as a Spectra/Por® Float-A-Lyzer G2 sized for nanoparticles of a molecular weight of 100 kD, applied exactly as specified from Spectrum Labs, as in the Examples herein.

In a preferred embodiment of the method of preparing the nanoparticle formulation according to the invention, the dispersion is subjected to a cold temperature incubation at a temperature of from 0 to 10° C. after buffering of the dispersion to a pH of approximately 7, and prior to purifying the dispersion by filtration. When a cold temperature incubation step is employed in this manner, encapsulation of the one or more therapeutic agents is more effective. This is especially the case when the therapeutic agent is acetate.

In a preferred embodiment of the invention, the nanoparticle formulation is a cationic liposome comprising: (i) a cationic cholesterol derivative comprising a polyamine appendage of the formula $H_2N(CH_2)_xNH(CH_2)_y NH(CH_2)_zNHC(O)$—, wherein x is 1 to 4, y is 1 to 4, and z is 1 to 4; (ii) a saturated neutral phospholipid of phosphatidylcholine or phosphatidylethanolamine comprising a saturated fatty acid chain of $C_{10-20}$; (iii) cholesterol or a neutral cholesterol derivative selected from the group consisting of cholesteryl acetate, cholesteryl butyrate, cholesteryl valerate, cholesteryl caprylate, cholesteryl dodecanoate, cholesteryl oleate, and cholesteryl stearate; and (iv) a saturated fatty acid, PEGylated, neutral derivative of phosphatidylethanolamine or phosphatidylcholine comprising a saturated fatty acid chain of $C_{12-20}$ and a PEG chain with a molecular weight of 1500 to 2000, wherein a short-chain fatty acid selected from the group consisting of acetate, propionate and butyrate is encapsulated therein.

In another preferred embodiment of the invention, the nanoparticle formulation is a cationic liposome comprising: (i) a cationic cholesterol derivative comprising a polyamine appendage of the formula $H_2N(CH_2)_xNH(CH_2)_y NH(CH_2)_zNHC(O)$—, wherein x is 1 to 4, y is 1 to 4, and z is 1 to 4; (ii) a saturated neutral phospholipid of phosphatidylcholine or phosphatidylethanolamine comprising a saturated fatty acid chain of $C_{10-20}$; (iii) cholesterol; and (iv) a saturated fatty acid, PEGylated, neutral derivative of phosphatidylethanolamine or phosphatidylcholine comprising a saturated fatty acid chain of $C_{12-20}$ and a PEG chain with a molecular weight of 1500 to 2000, wherein a short-chain fatty acid selected from the group consisting of acetate, propionate and butyrate is encapsulated therein, and the components (i) to (iv) are present in the molar ratios of 20-40:20-40:25-55:1-10, respectively.

In a further preferred embodiment of the invention, the nanoparticle formulation is a cationic liposome comprising: (i) a cationic cholesterol derivative comprising a polyamine appendage of the formula $H_2N(CH_2)_xNH(CH_2)_y NH(CH_2)_zNHC(O)$—, wherein x is 1 to 4, y is 1 to 4, and z is 1 to 4; (ii) a saturated neutral phospholipid of phosphatidylcholine or phosphatidylethanolamine comprising a saturated fatty acid chain of $C_{10-20}$; (iii) cholesterol; and (iv) a saturated fatty acid, PEGylated, neutral derivative of phosphatidylethanolamine or phosphatidylcholine comprising a saturated fatty acid chain of $C_{12-20}$ and a PEG chain with a molecular weight of 1500 to 2000, wherein a short-chain fatty acid selected from the group consisting of acetate, propionate and butyrate is encapsulated therein at a concentration of 10 to 10 mM, and the components (i) to (iv) are present in the molar ratios of 20-40:20-40:25-55:1-10, respectively, and the average particle size of the liposomes is in the range of 40 to 120 nm.

In another preferred embodiment of the invention, the nanoparticle formulation is a cationic liposome comprising: (i) CDAN; (ii) a saturated neutral phospholipid of phosphatidylcholine or phosphatidylethanolamine comprising a saturated fatty acid chain of $C_{10-20}$; (iii) cholesterol; and (iv) a saturated fatty acid, PEGylated, neutral derivative of phosphatidylethanolamine or phosphatidylcholine comprising a saturated fatty acid chain of $C_{12-20}$ and a PEG chain with a molecular weight of approximately 2000, wherein a short-chain fatty acid selected from the group consisting of acetate, propionate and butyrate is encapsulated therein at a concentration of 10 to 10 mM.

In a further preferred embodiment of the invention, the nanoparticle formulation is a cationic liposome comprising: (i) a cationic cholesterol derivative comprising a polyamine appendage of the formula $H_2N(CH_2)_xNH(CH_2)_y NH(CH_2)_zNHC(O)$—, wherein x is 1 to 4, y is 1 to 4, and z is 1 to 4; (ii) a saturated neutral phospholipid of phosphatidylcholine comprising a saturated fatty acid chain of $C_{10-20}$; (iii) cholesterol; and (iv) a saturated fatty acid, PEGylated, neutral derivative of phosphatidylethanolamine comprising a saturated fatty acid chain of $C_{12-20}$ and a PEG chain with a molecular weight of approximately 2000, wherein acetate is encapsulated therein, and the average particle size of the liposomes is in the range of 40 to 120 nm.

The invention will now be described in more detail by way of example only and with reference to the following Figures. In relation to the Examples presented herein, comparable results may be obtained with propionic acid and butyric acid.

FIG. 1. Nanoparticle size distributions for varying concentrations of acetate in formulations according to Example 2.

Figure 2:
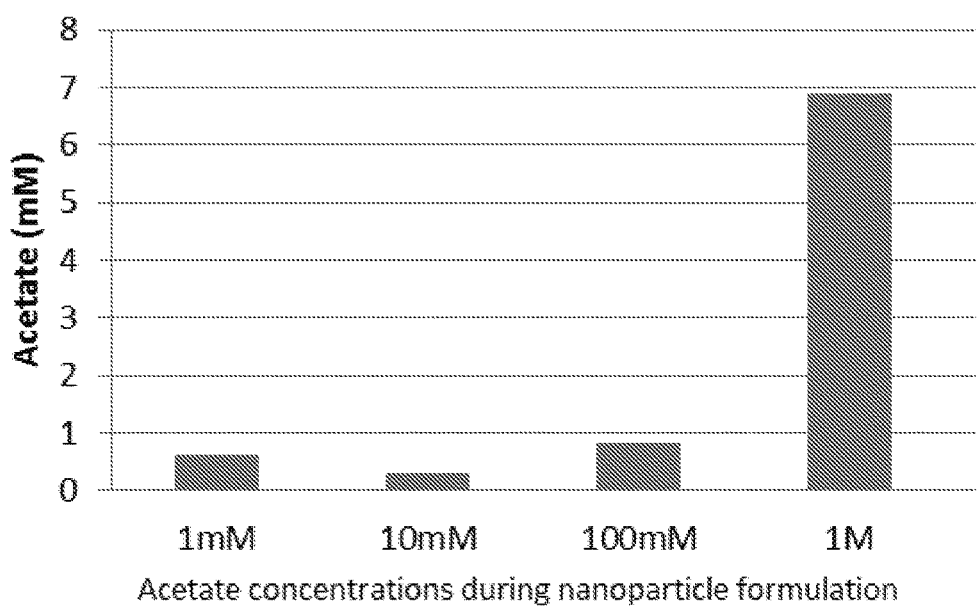

FIG. 2. $^1$H-NMR quantification of encapsulated acetate for varying concentrations of acetate in formulations according to Example 2.

Figure 3:
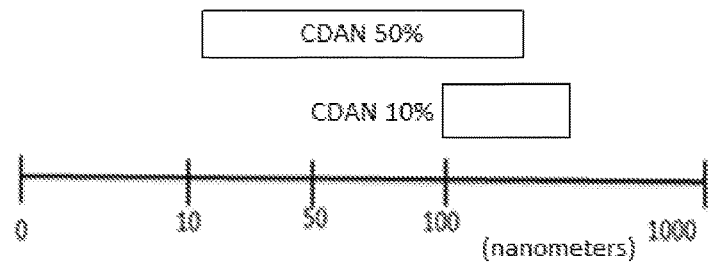

FIG. 3. Nanoparticle size distributions for varying amounts of component (i) (CDAN) in formulations produced by the method of Example 2.

Figure 4:
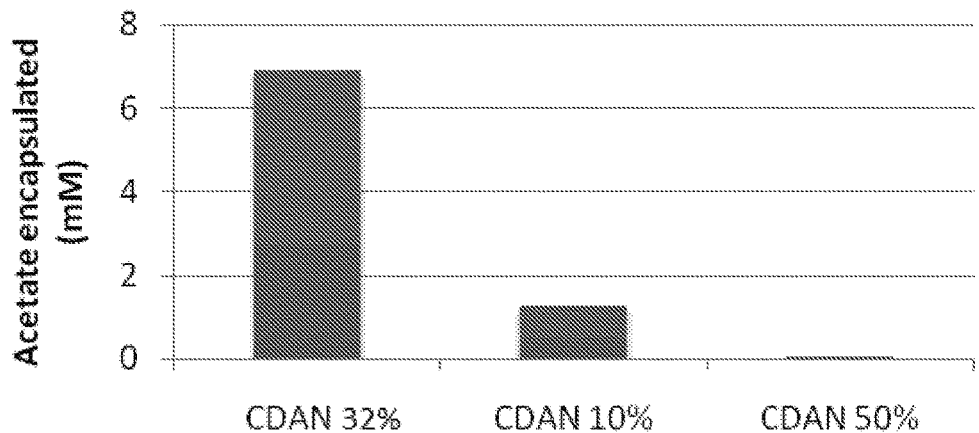

FIG. 4. $^1$H-NMR quantification of encapsulated acetate for varying amounts of component (i) (CDAN) in formulations produced by the method of Example 2.

Figure 5:
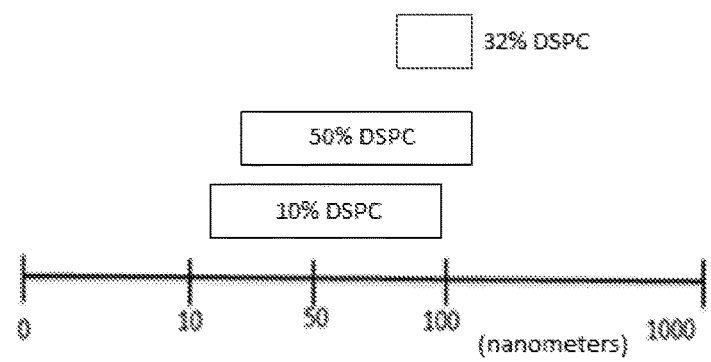

FIG. 5. Nanoparticle size distributions for varying amount of component (ii) (DSPC) in formulations produced by the method of Example 2.

Figure 6:
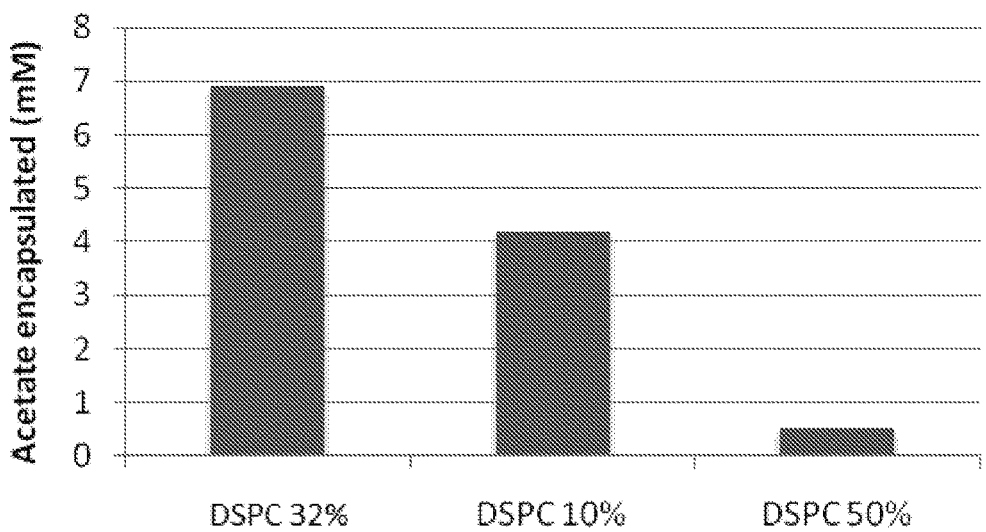

FIG. 6. $^1$H-NMR quantification of encapsulated acetate for varying amounts of component (ii) (DSPC) in formulations produced by the method of Example 2.

Figure 7:
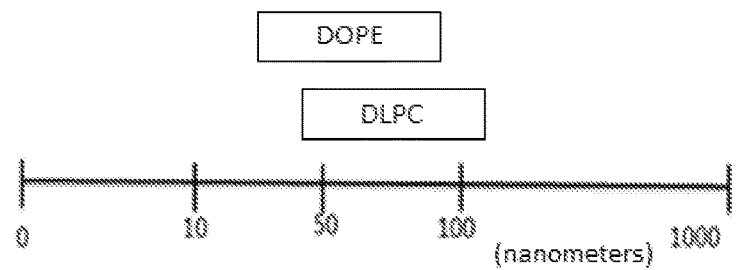

FIG. 7. Nanoparticle size distribution for varying nature of component (ii), with DOPE and DLPC in formulations produced by the method of Example 2.

Figure 8:
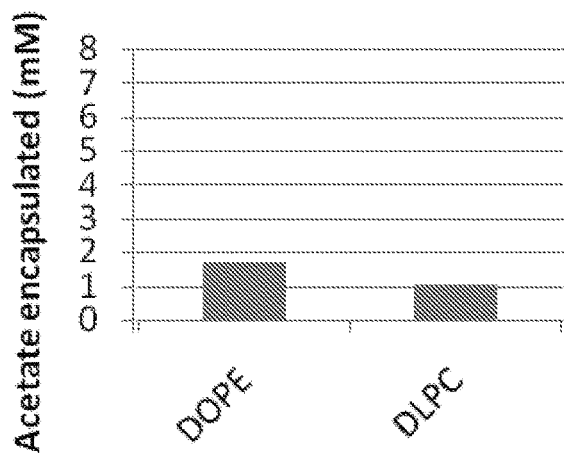

FIG. 8. $^1$H-NMR quantification of encapsulated acetate for varying nature of component (ii), with DOPE and DLPC in formulations produced by the method of Example 2.

Figure 9:
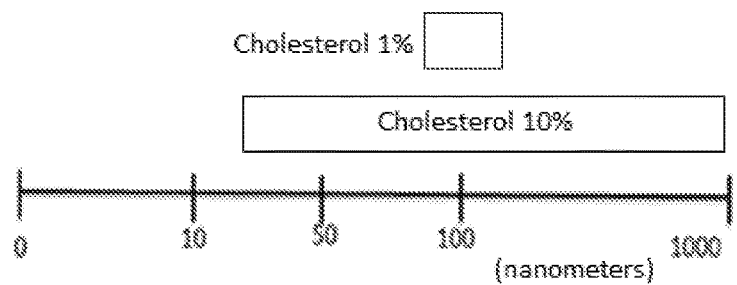

FIG. 9. Nanoparticle size distributions for varying amounts of component (iii) (cholesterol) in formulations produced by the method of Example 2.

Figure 10:
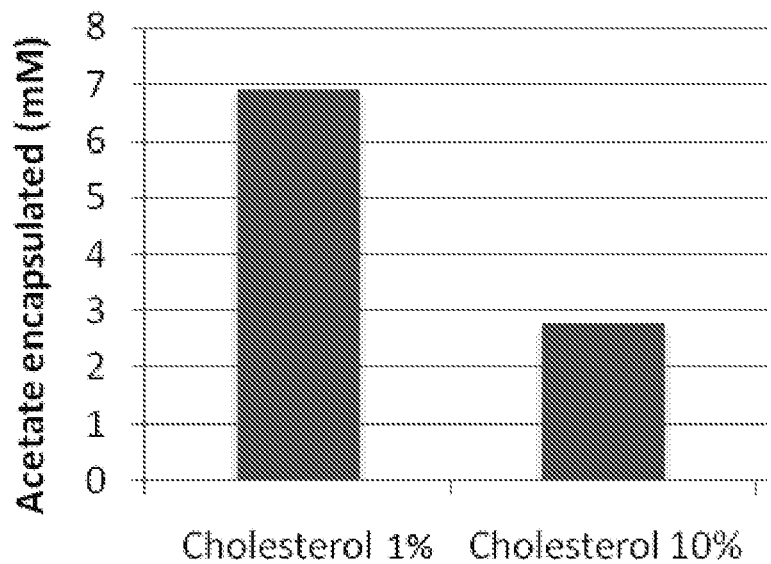

FIG. 10. $^1$H-NMR quantification of encapsulated acetate for varying amounts of component (iii) (cholesterol) in formulations produced by the method of Example 2.

Figure 11:
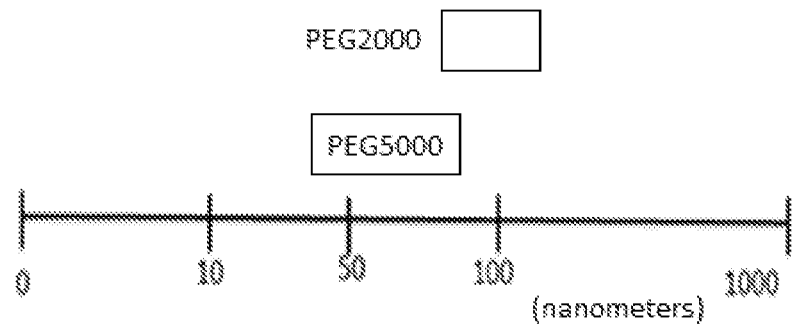

FIG. 11. Nanoparticle size distributions for varying nature of component (iv) (DSPE-PEG) in terms of the molecular weight of the PEG group in formulations produced by the method of Example 2.

Figure 12:
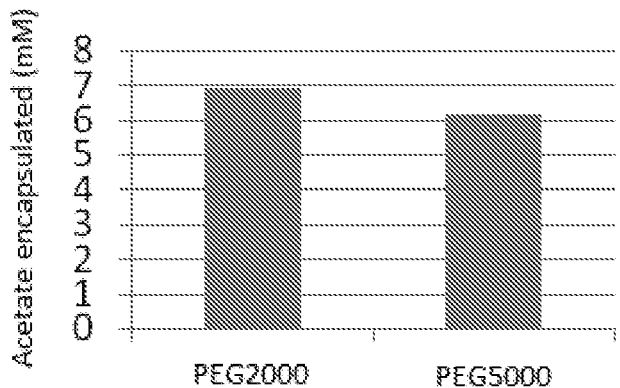

FIG. 12. $^1$H-NMR quantification of encapsulated acetate for varying nature of component (iv) (DSPE-PEG) in terms of the molecular weight of the PEG group in formulations produced by the method of Example 2.

Figure 13:
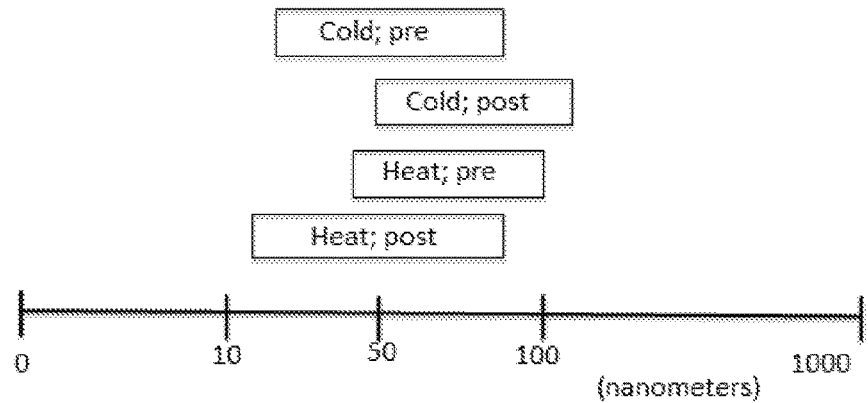

FIG. 13. Nanoparticle size distributions in terms of thermostability with regard to formulations produced by the method of Example 2.

Figure 14:
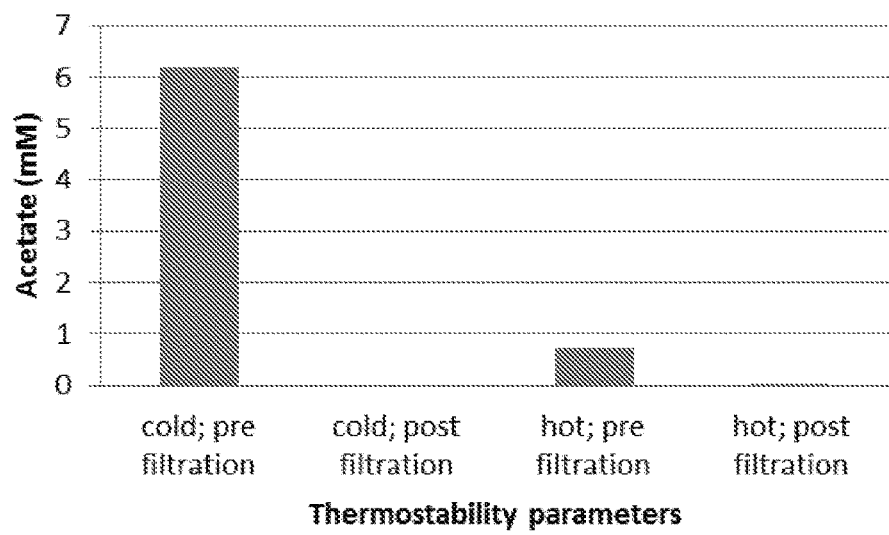

FIG. 14. $^1$H-NMR quantification of encapsulated acetate in terms of thermostability with regard to formulations produced by the method of Example 2.

Figure 15:
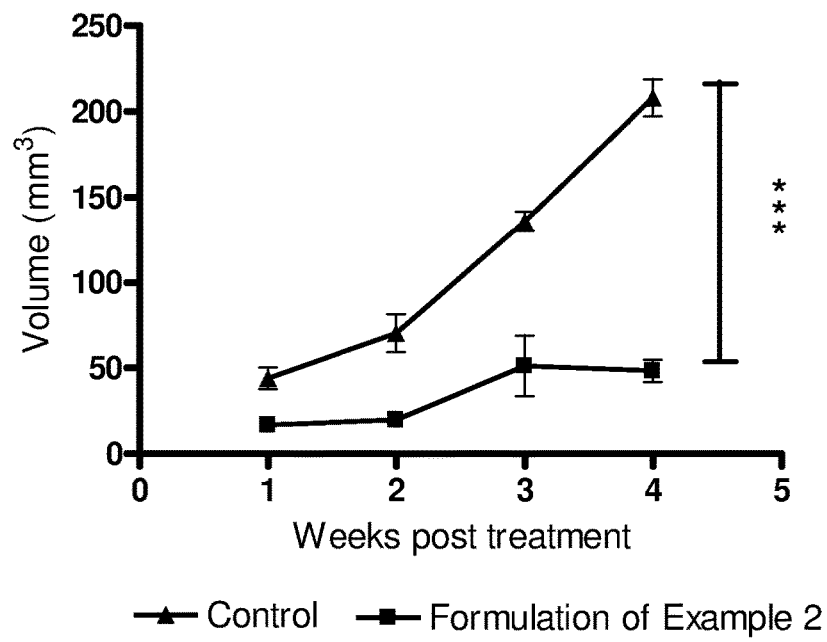

FIG. 15. The tumour growth rate of a control xenograft model and a model treated with the formulation of Example 2.

Figure 16:
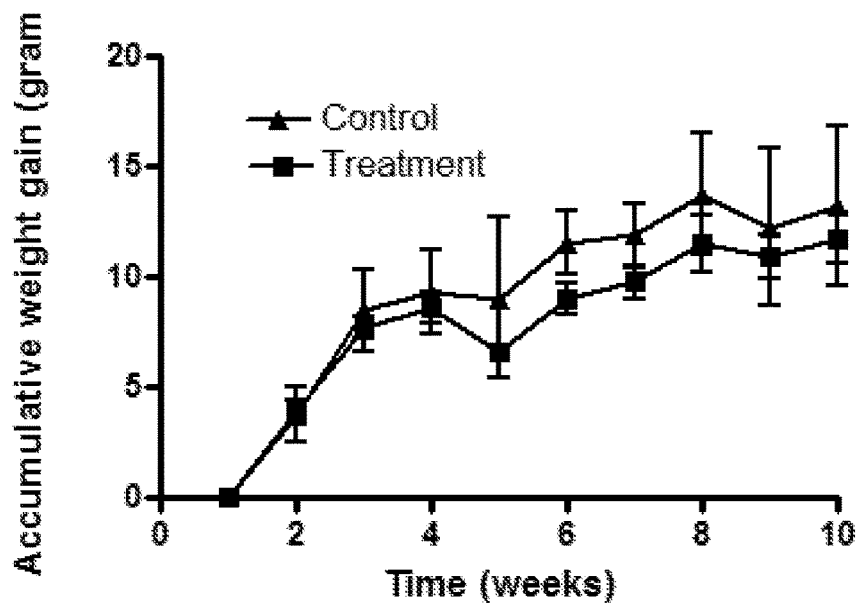

FIG. 16. The effect of twice daily intraperitoneal infusion of the formulation of Example 2 on the weight gain of high fat fed animals.

Figure 17:
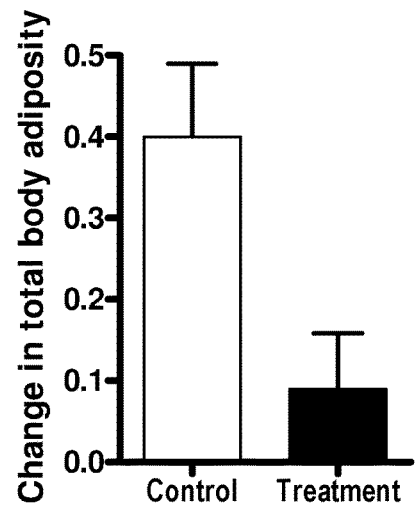

FIG. 17. The effect of twice daily intraperitoneal infusion of the formulation of Example 2 on the whole body adiposity of high-fat fed animals.

Figure 18:
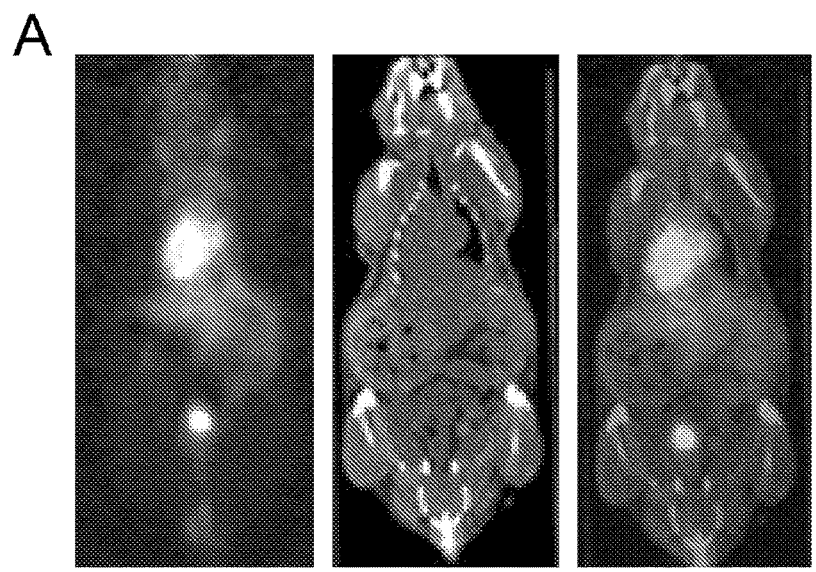
Figure 18:
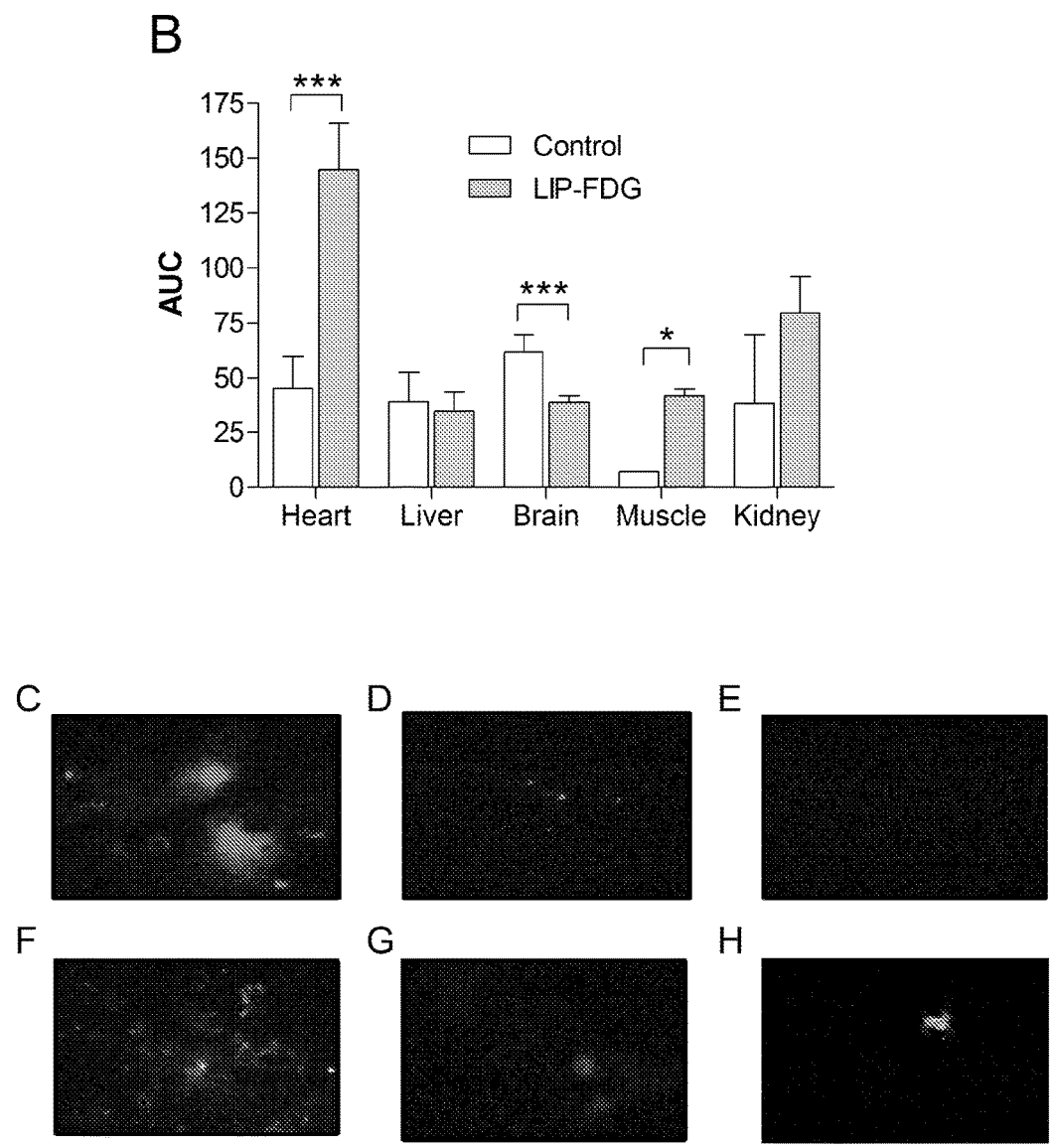
Figure 18:
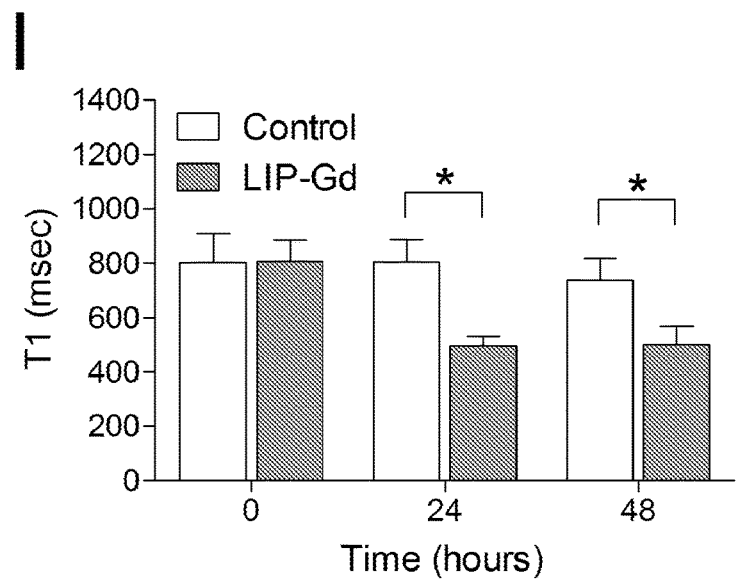
Figure 18:
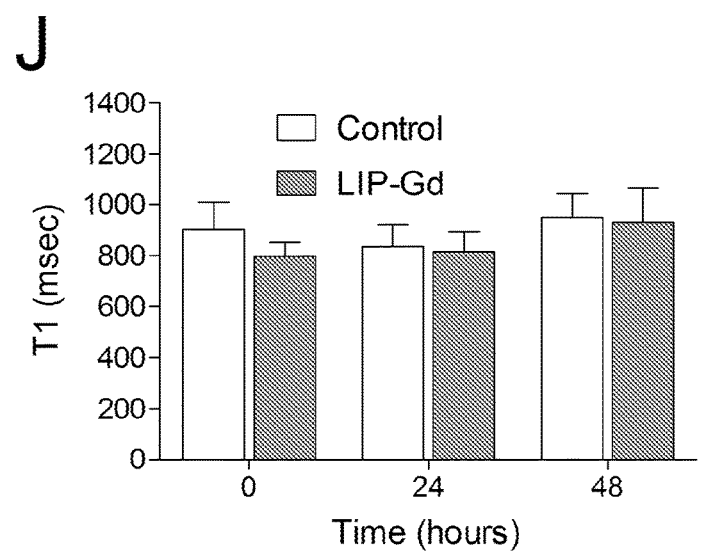
Figure 18:
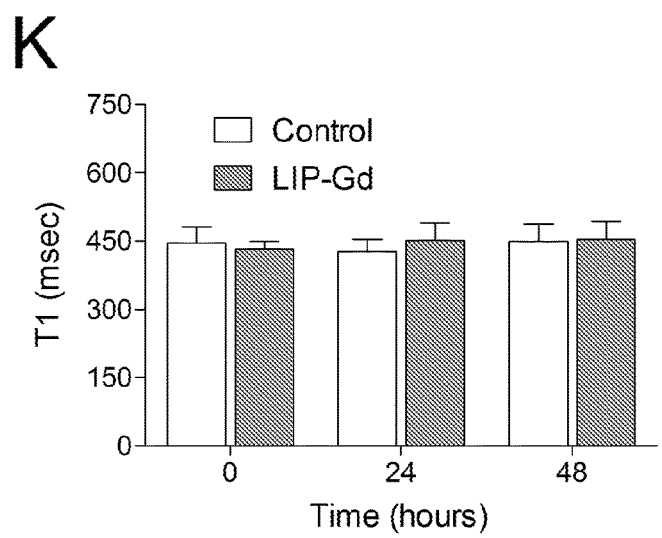

FIG. 18. Bio-distribution of liposomal conjugations. (A) Representative PET, CT and PET/CT fusion images at 2 h post injection in C57BL/6 mice injected with LIP-FDG nanoparticles (10 MBq of encapsulated 18F-FDG) (B) Area under the curve (AUC) data recorded from regions of interest (ROI) at 30 min post-injection of 18F-FDG (Control) or LIPFDG (n=4/group). (C-G) are representative histological images from C57BL/6 mice, collected 2 h post i.p. injection of LIP-Rhd; (C) Liver, (D) Heart, (E) Muscle, (F) Spleen and (G) Lung. (H) Representative histological image of xenograft tumour collected 2 h post i.p. injection of LIP-XG-Rhd. (I-K) are T1 values recorded at 0, 24 and 48 hours in ROI post i.p. injection of LITA-Gd or LITA (Control) nanoparticles (n=4/group); (I) Liver, (J) Kidney and (K) Subcutaneous fat. Results are displayed as mean±SD. Data analysed by student's t-test; *=$p<0.05$, ***=$p<0.001$.

Figure 19:
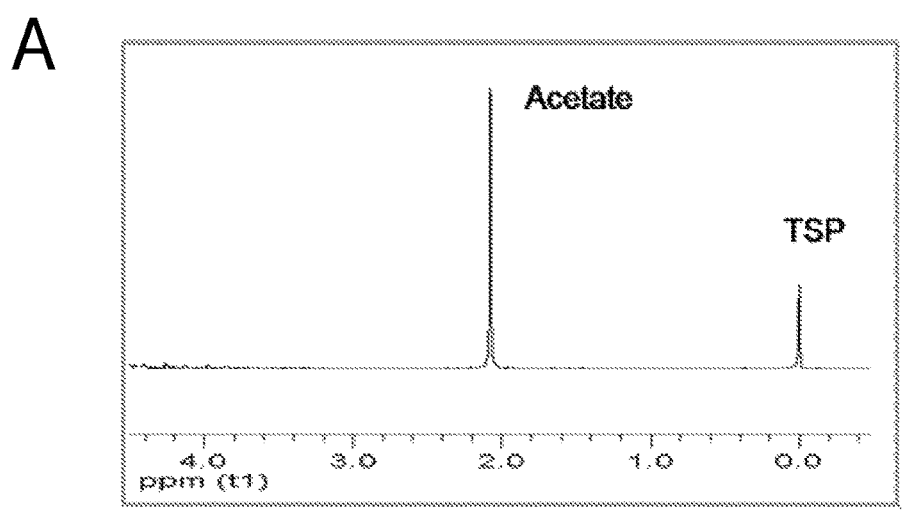
Figure 19:
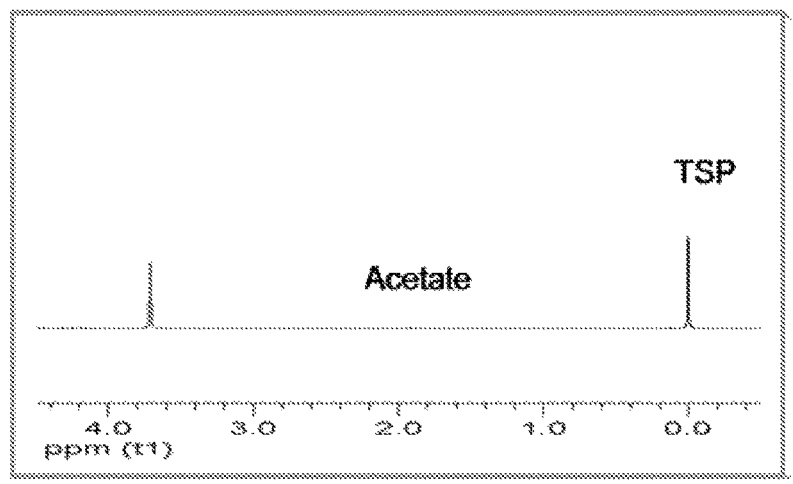
Figure 19:
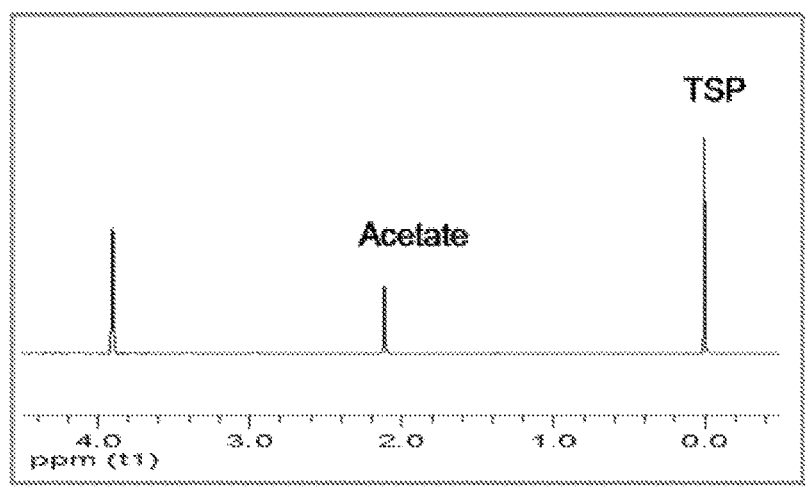
Figure 19:
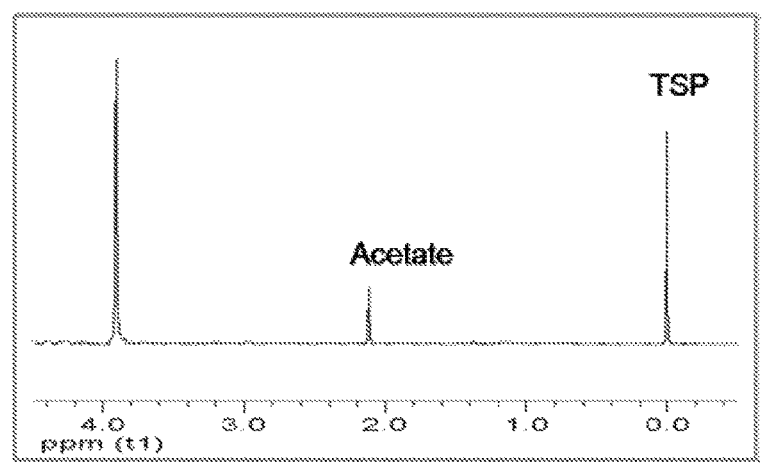
Figure 19:
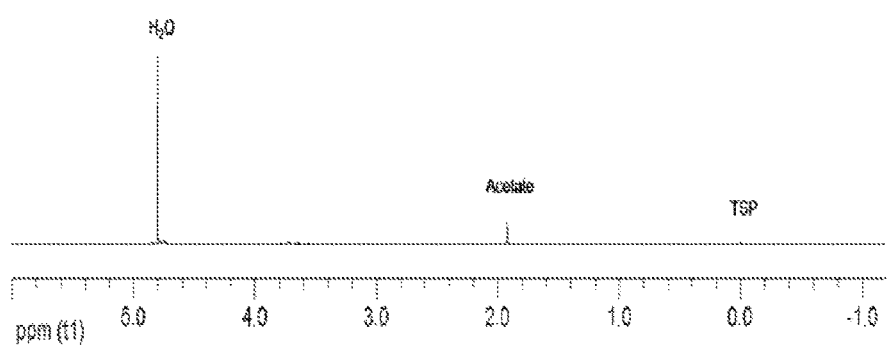
Figure 19:
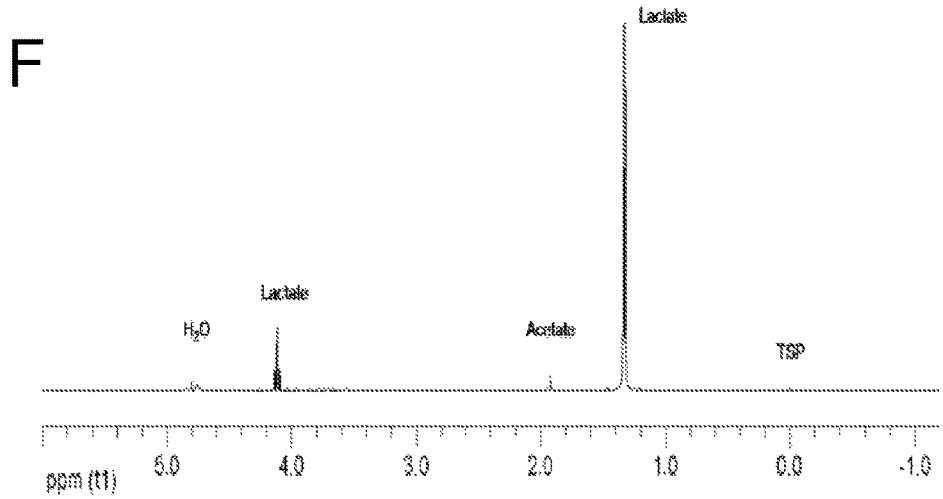
Figure 19:
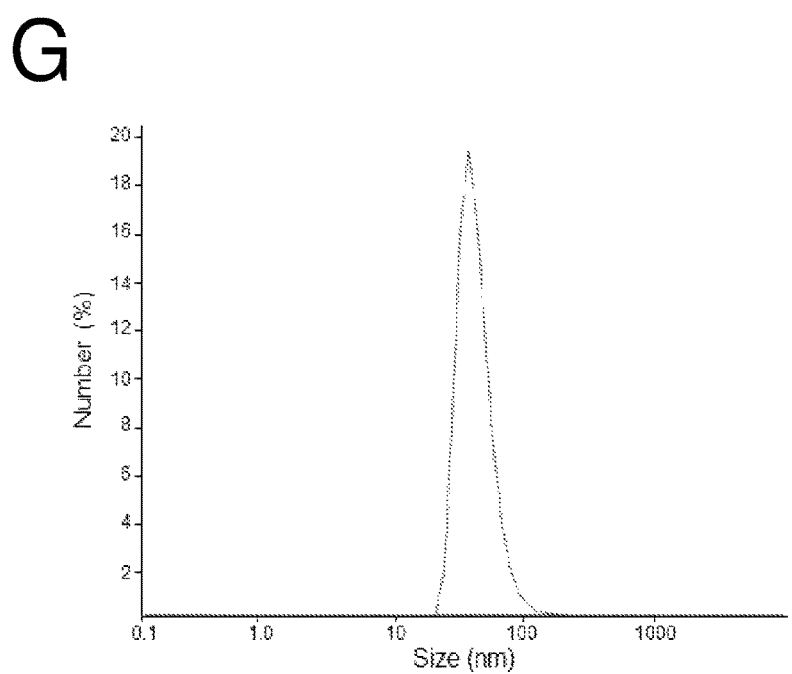
Figure 19:
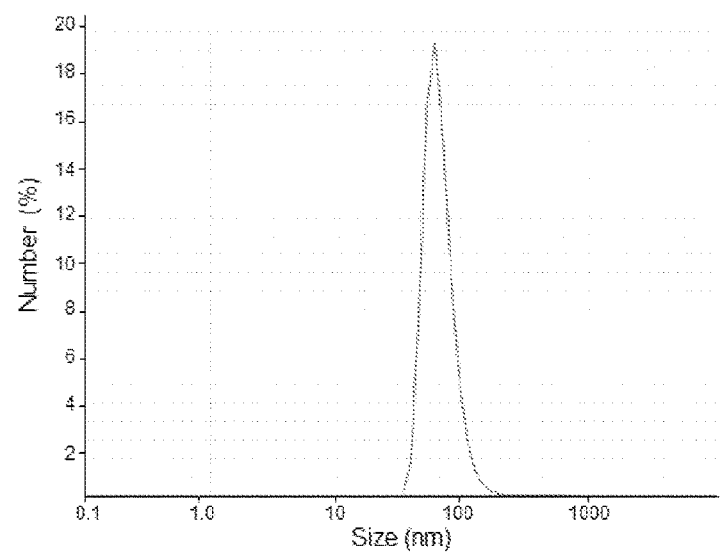
Figure 19:
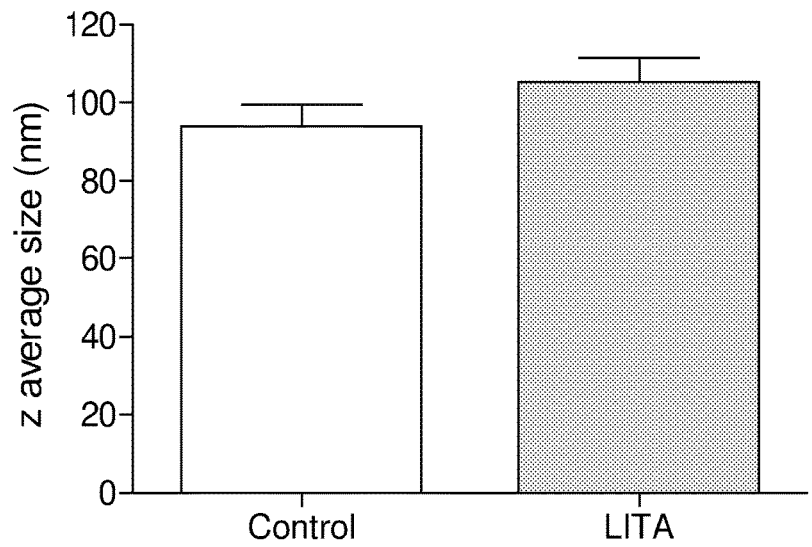

FIG. 19. Acetate encapsulation and quantification. 1H NMR spectra from 4.5 ppm to -0.5 ppm of (A) 4 mM acetate solution, (B) 4 mM acetate solution with albumin, (C) LITA solution with albumin (2 g); (D) LITA solution with albumin (4 g). Trimethylsilyl propionate (TSP) provides a reference at 0 ppm. The peak for acetate is normally observed at 2.03 ppm. The NMR spectra of LITA nanoparticles without lactate (E) and with lactate (5.2mg sodium lactate) (F) are shown. The size of liposome preparations was measured using a Zetasizer Nano (Malvern, UK), (G) and (H) show the size distribution of control (containing HEPES) and LITA (liposome encapsulated acetate) respectively, (I) average size of control and LITA liposomes.

Figure 20:
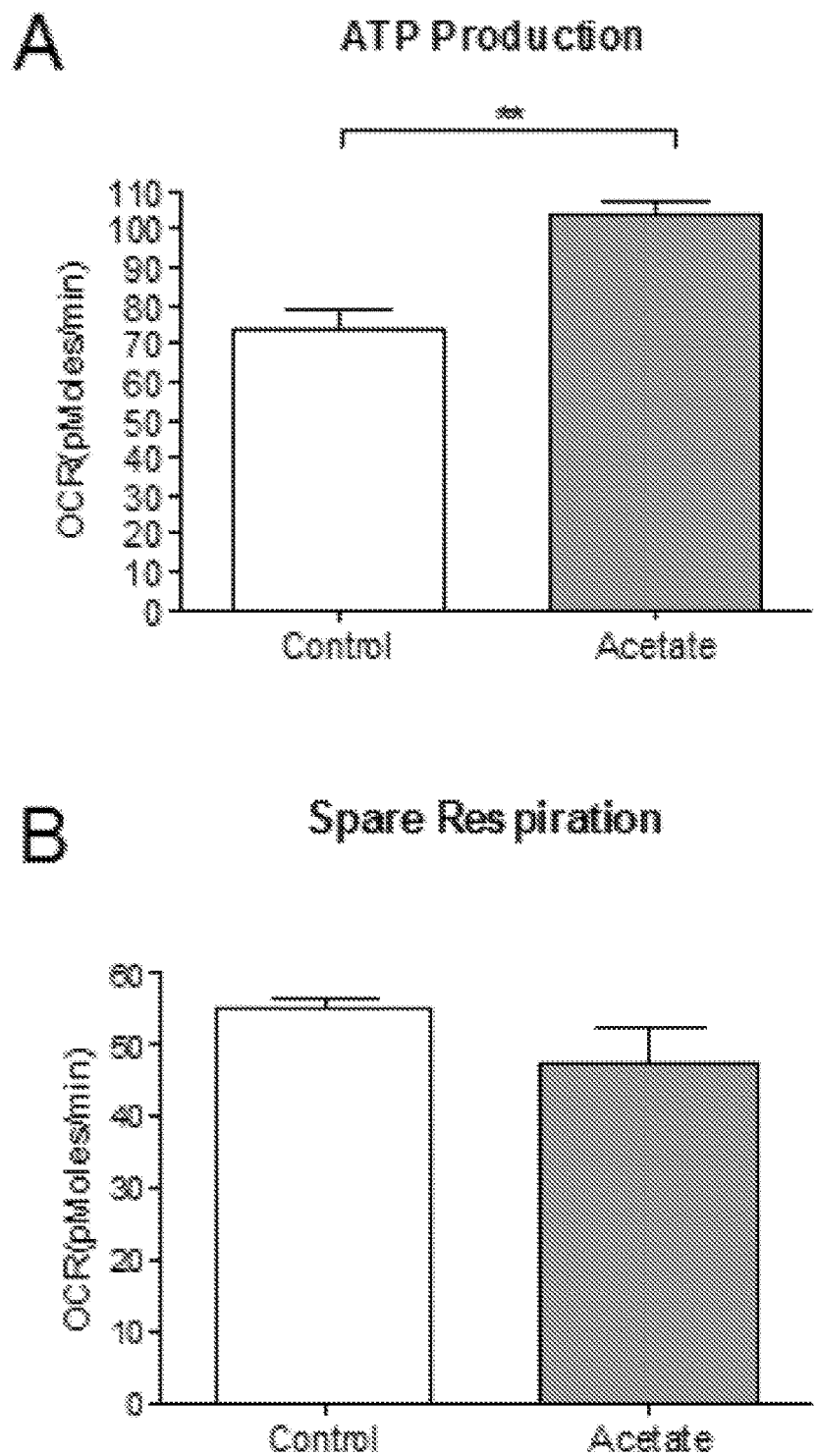

FIG. 20. Mitochondrial calorimetry. HT-29 cells were treated with acetate (5 mM) or without (Control) and assessed for ATP production by the Seahorse assay in vitro. (A) ATP production; (B) Spare respiration; n=4/group; **=$p<0.01$; data analysed using student t-test (GraphPad Prism); OCR: Oxygen consumption rate (pMoles/min).

Figure 21:
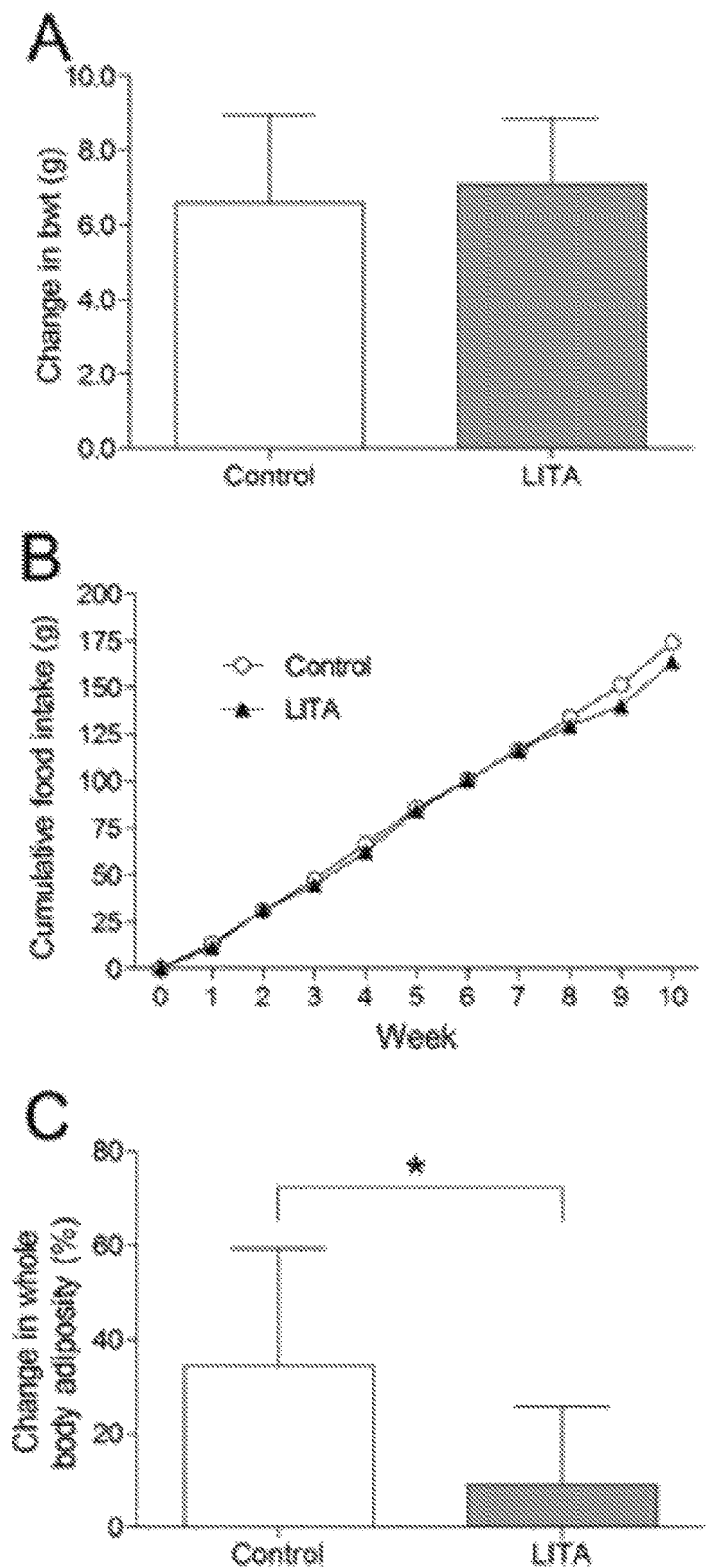
Figure 21:
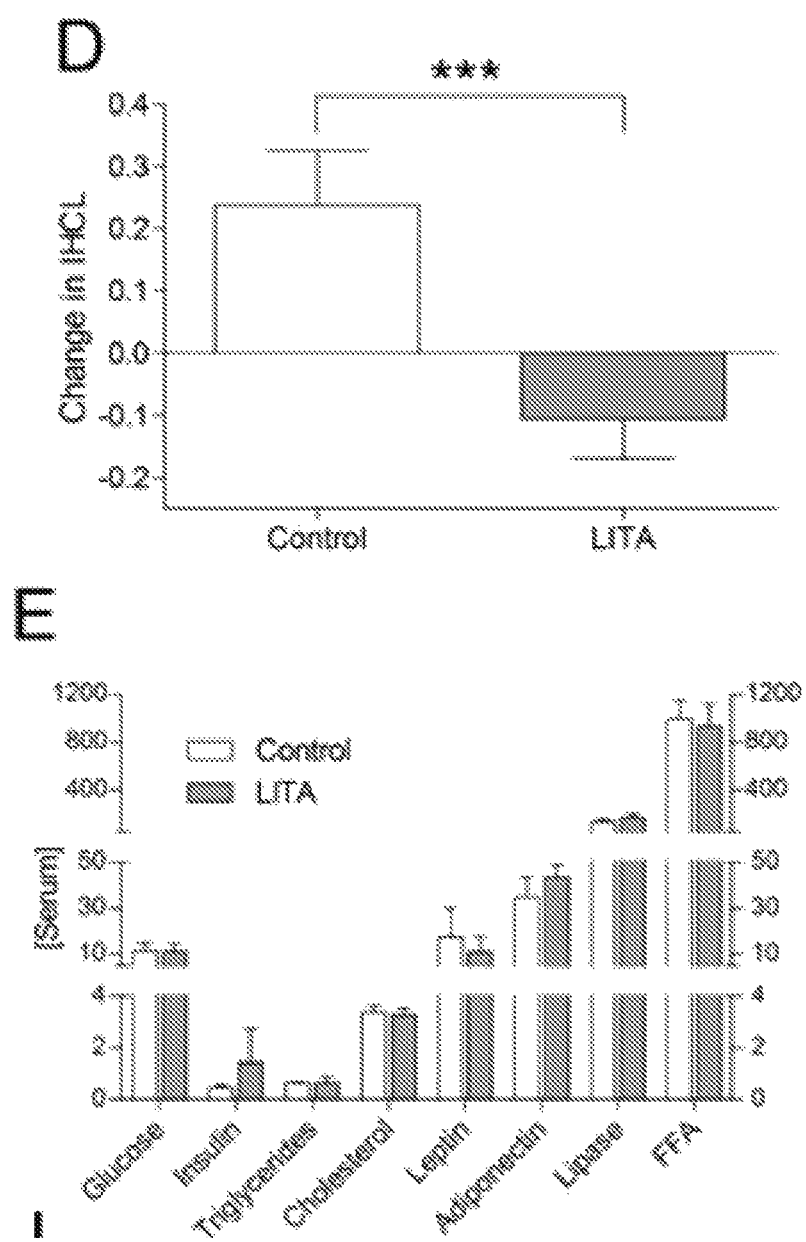
Figure 21:
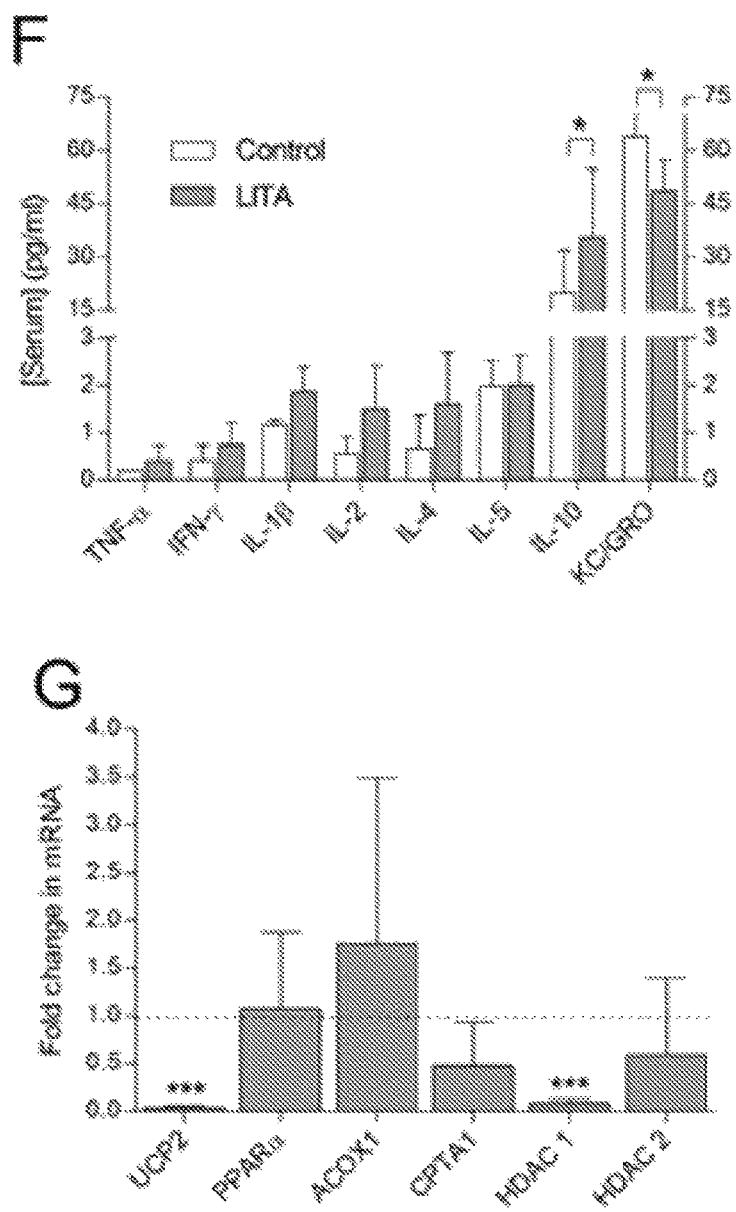
Figure 21:
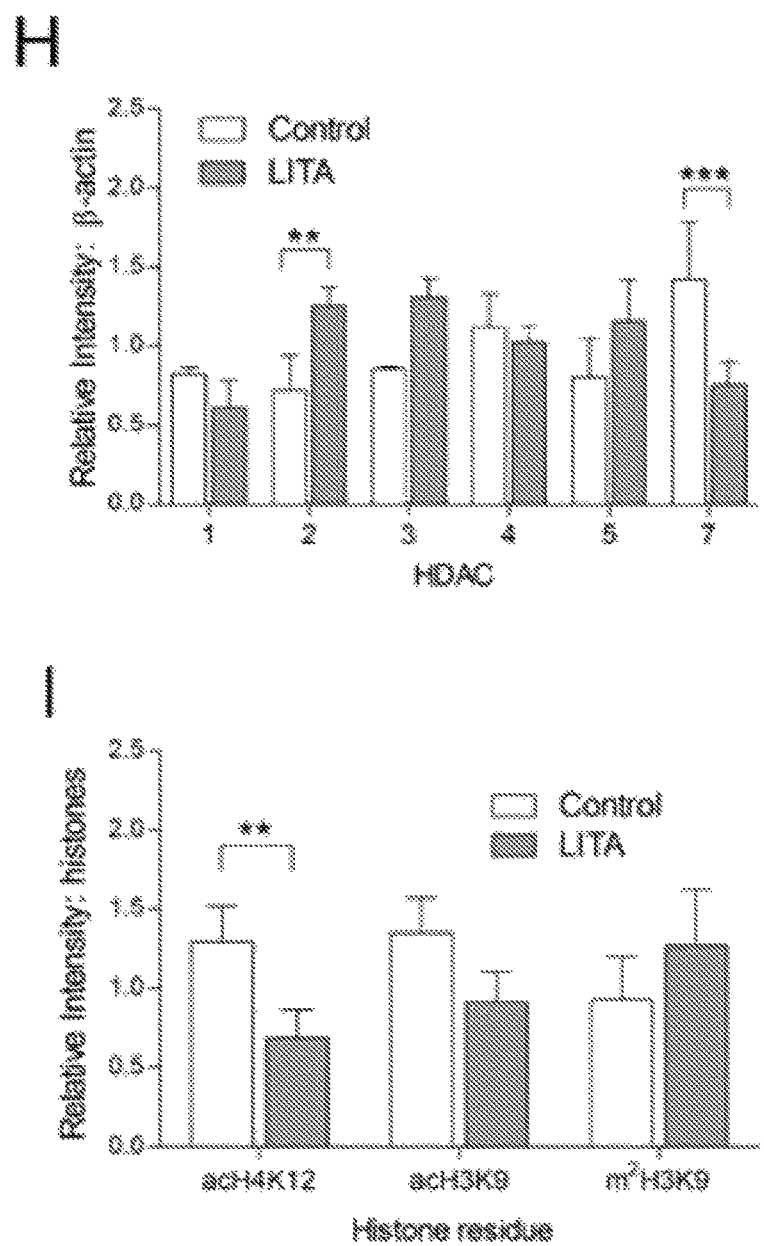

FIG. 21. The reparative effects of LITA nanoparticles in mice placed on a HFD diet. After 5 weeks placed on a high fat diet (HFD) mice were injected every three days with either liposome encapsulated acetate (LITA) nanoparticles or control (HEPES) for an additional 5 weeks. (A) Change in body weight (g); (B) Cumulative food intake (g/week); (C) Change in whole body adiposity (%); (D) Change in IHCL; (E) Plasma lipids and additional circulating peptides (glucose (mmol/L), insulin, triglycerides (mmol/L), triglycerides (mmol/L), Leptin (ng/ml), Adiponectin (ng/ml), Lipase (U/L), Free fatty acids (FFA) (µtmol/L); (F) Serum levels of inflammatory markers (([serum](pg/ml)), TNF-α, IFN-γ, IL-1β, IL-2, IL-4, IL-5, IL-10 and KC/GRO, respectively; (G) The fold change in hepatic mRNA levels in LITA compared to control groups, UCP2, PPARα, ACOX1, CPTA1, HDAC1 and HDAC2, respectively; (H) Expression of HDAC proteins (normalised to β-actin); (I) Expression of histone residues (normalised to total histone), acH4K12, acH3K9 and m$^2$H3K9, respectively. Data analysed by Student's t-test or two-way ANOVA with Bonferroni post hoc test; n=8/group; *=$p<0.05$, =$p<0.01$, *=$p<0.001$.

Figure 22:
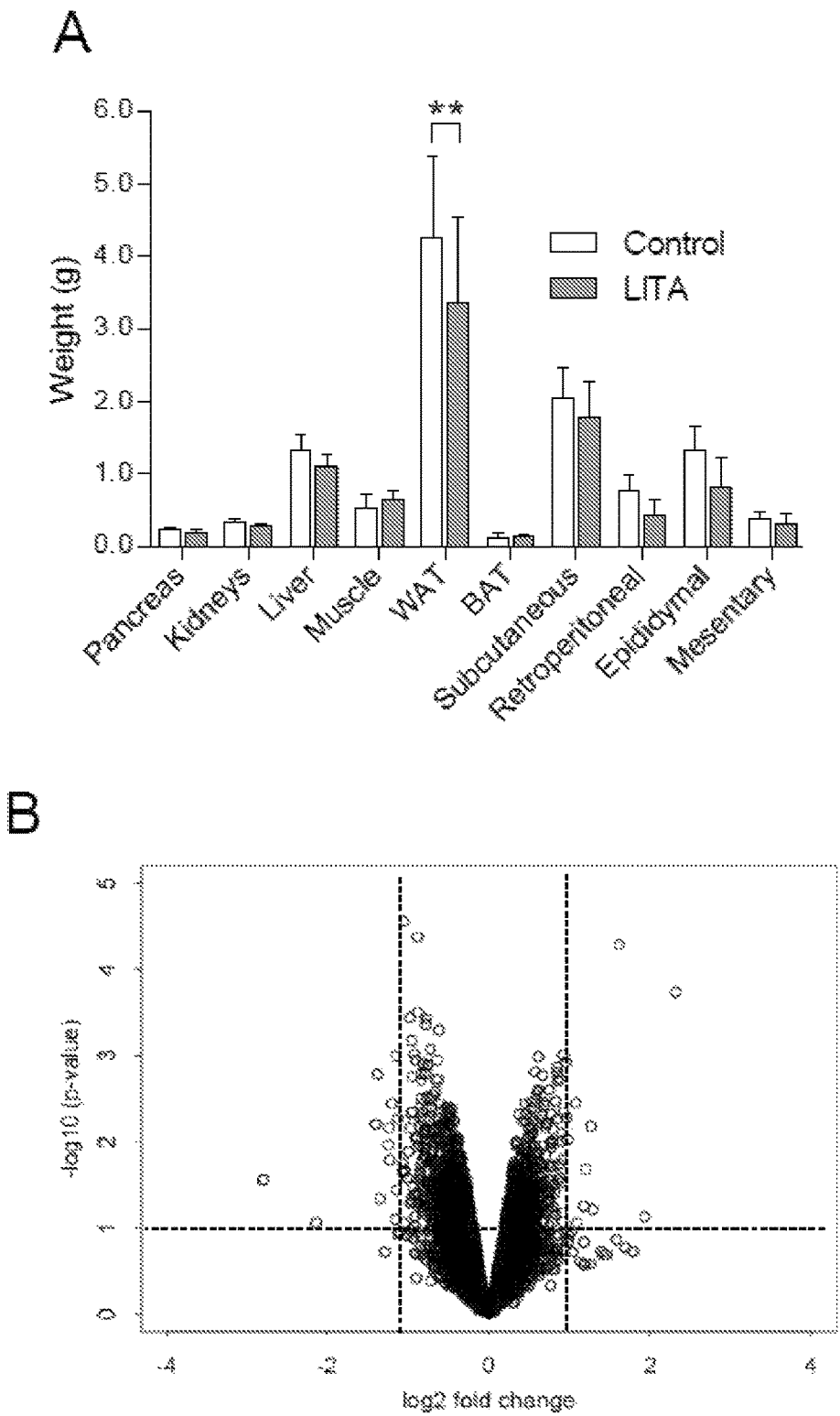

FIG. 22. The reparative effects of LITA nanoparticles in mice placed on a HFD diet. Mice were placed on a high fat diet (HFD) for 5 weeks. Chronic injections then began every three days with either liposome encapsulated acetate (LITA) nanoparticles or control (HEPES) for an additional 5 weeks (n=8/group). (A) Organ weight—pancreas, kidneys, liver, muscle, WAT, BAT, subcutaneous, retroperitoneal, epididymal, mesentary, respectively, (B) Microarray data (−log10 (p-value) vs log2 fold change); n=8/group; *=$p<0.05$, \*\*=p<0.01, \*\*\*=p<0.001. Data analysed by 2-way ANOVA with Bonferroni post-hoc test (GraphPad Prism).

Figure 23:
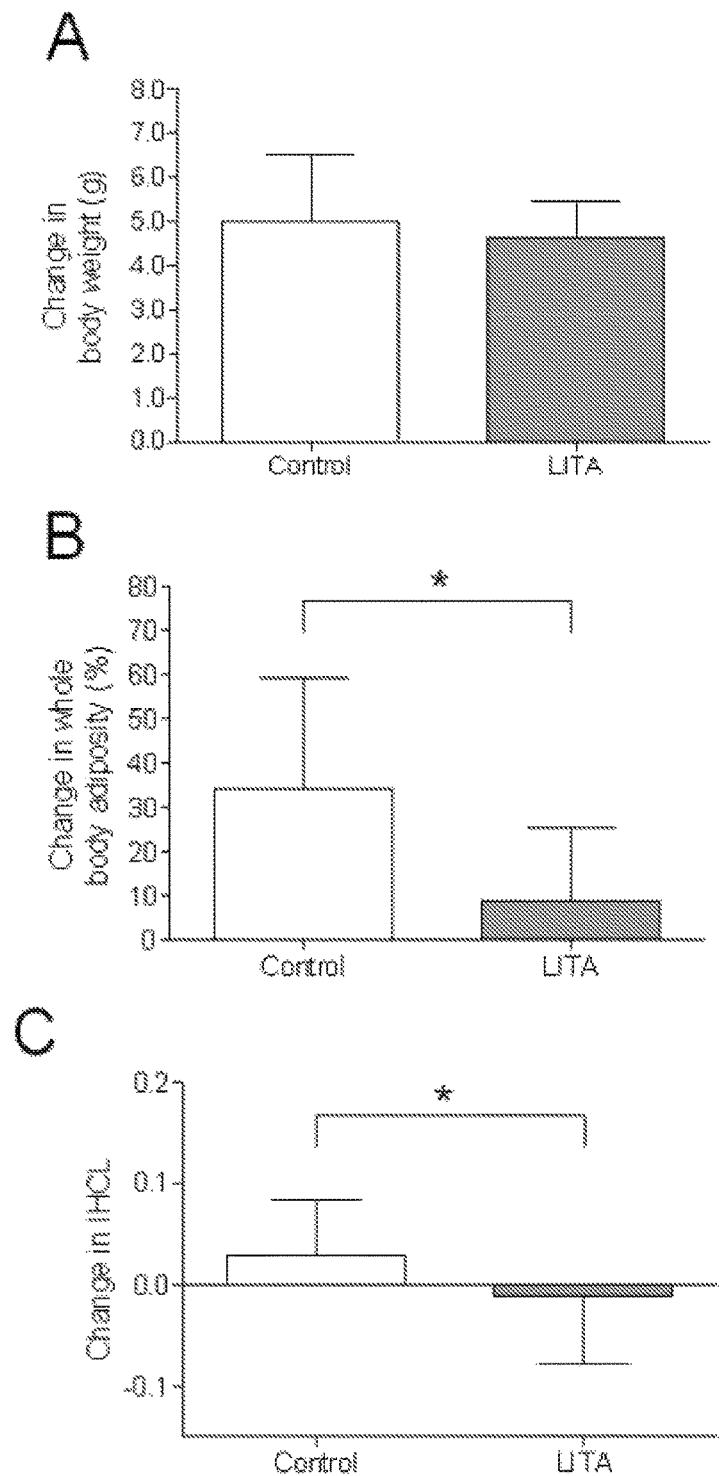
Figure 23:
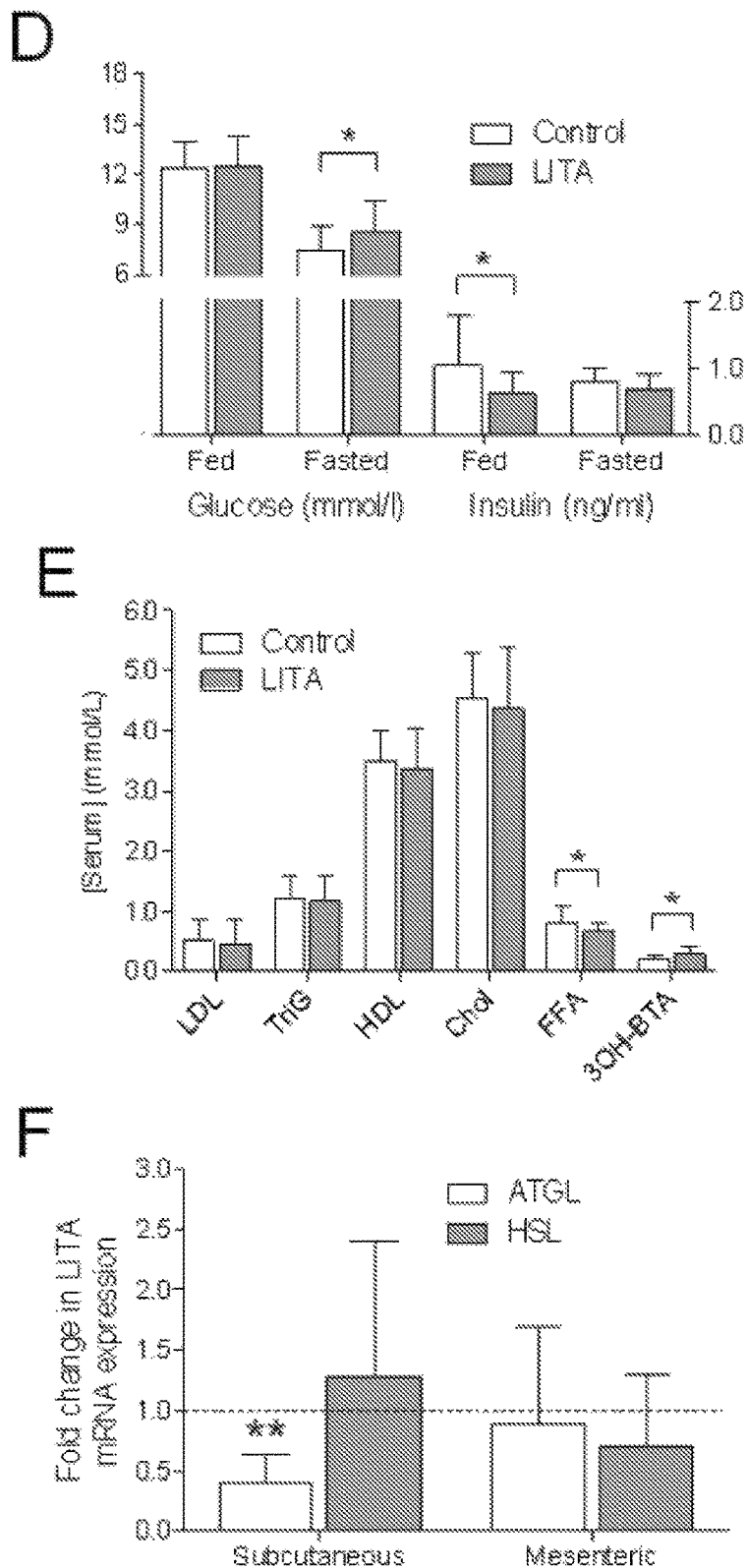
Figure 23:
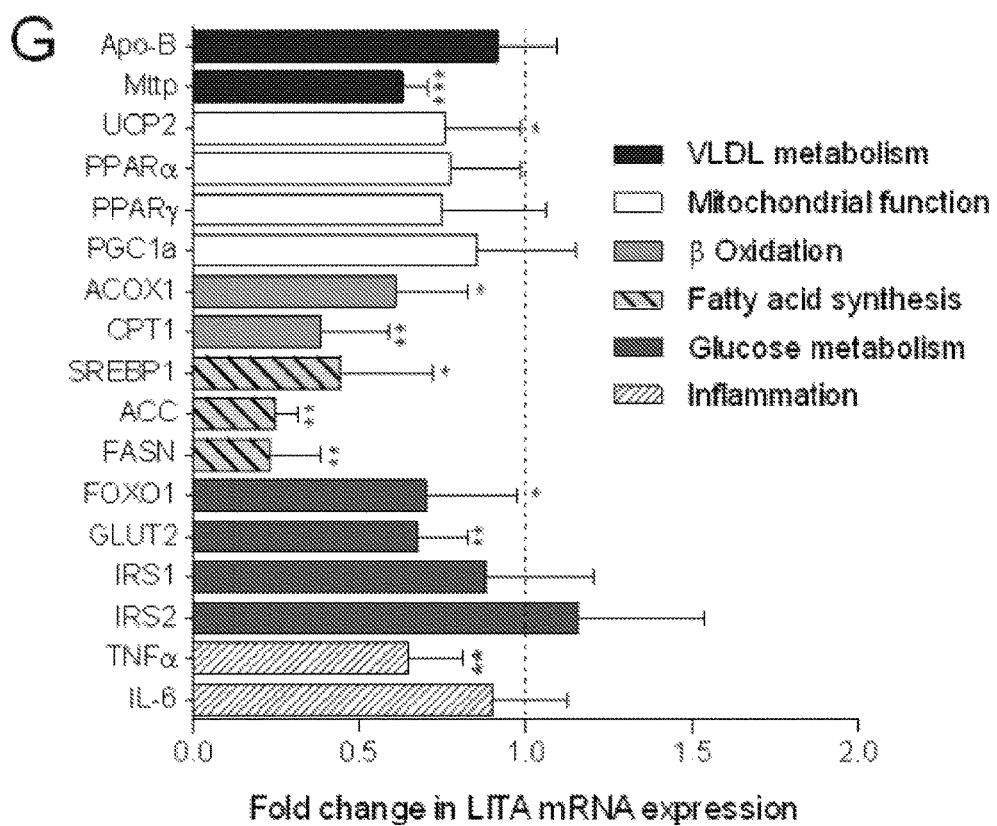
Figure 23:
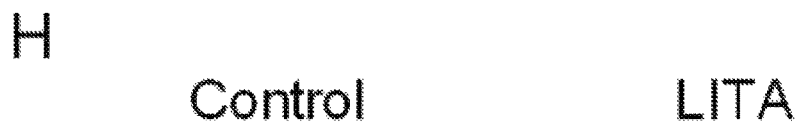
Figure 23:
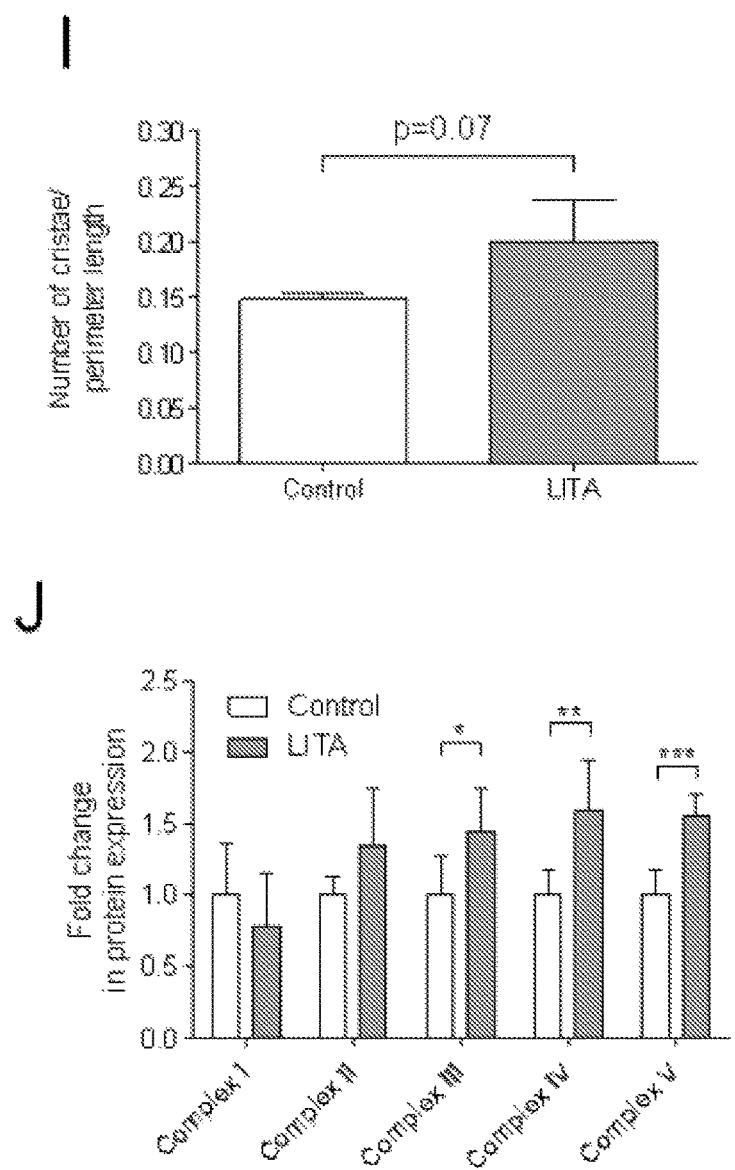

FIG. 23. The preventative effects of LITA nanoparticles in mice placed on a HFD diet. Mice were placed on a high fat diet (HFD) and injected every three days with either liposome encapsulated acetate (LITA) nanoparticles or control (HEPES) for 6 weeks. Overall change in; (A) Body weight (g), (B) Whole body adiposity (%), (C) IHCL. Fed and fasted levels of plasma (D) Fed and fasted levels of serum glucose (mmol/l) and insulin (ng/ml) (n=18/group), (E) Plasma lipids (mmol/L) (n=12/group), LDL, TriG, HDL, Chol, FFA and 3OH-BTA, respectively (F) Fold change in adipose tissue mRNA expression in LITA compared to control animals (n=6-8/group), subcutaneous and mesenteric (clear column is ATGL and shaded column in HSL); (G) Fold change in hepatic mRNA expression in LITA compared to control animals (n=6-8/group), genes (Apo-B, Mttp, UCP-2, PPARα, PPARγ, PGC1a, ACOX1, CPT1, SREBP1, ACC, FASN, FOX01, GLUT2, IRS 1, IRS2, TNFα, IL-6, respectively) grouped by function (VLDL metabolism, mitochondrial function, β oxidation, fatty acid synthesis, glucose metabolism and inflammation, respectively). (H) H&E staining of liver cross-section. (I) Number of cristae per perimeter length of mitochondrion (n=4/group). (J) Fold change in protein expression of mitochondrial complexes I-V (n=5/group). Data analysed by student's t-test or 2 way ANOVA with Bonferroni test for multiple comparisons where applicable (GraphPad Prism); n=24/group; \*=p<0.05, \*\*=p<0.01, \*\*\*=p<0.001.

Figure 24:
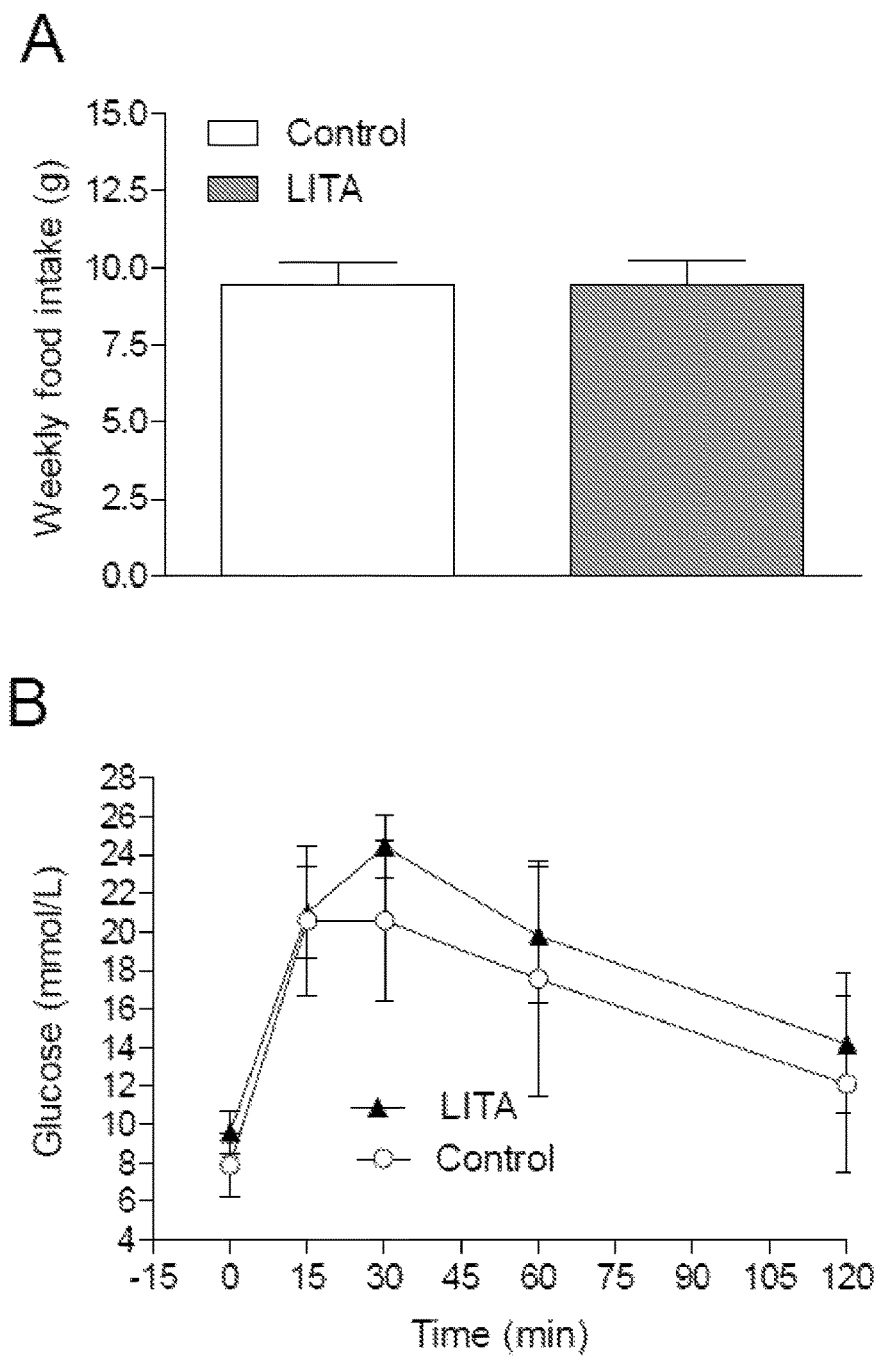
Figure 24:
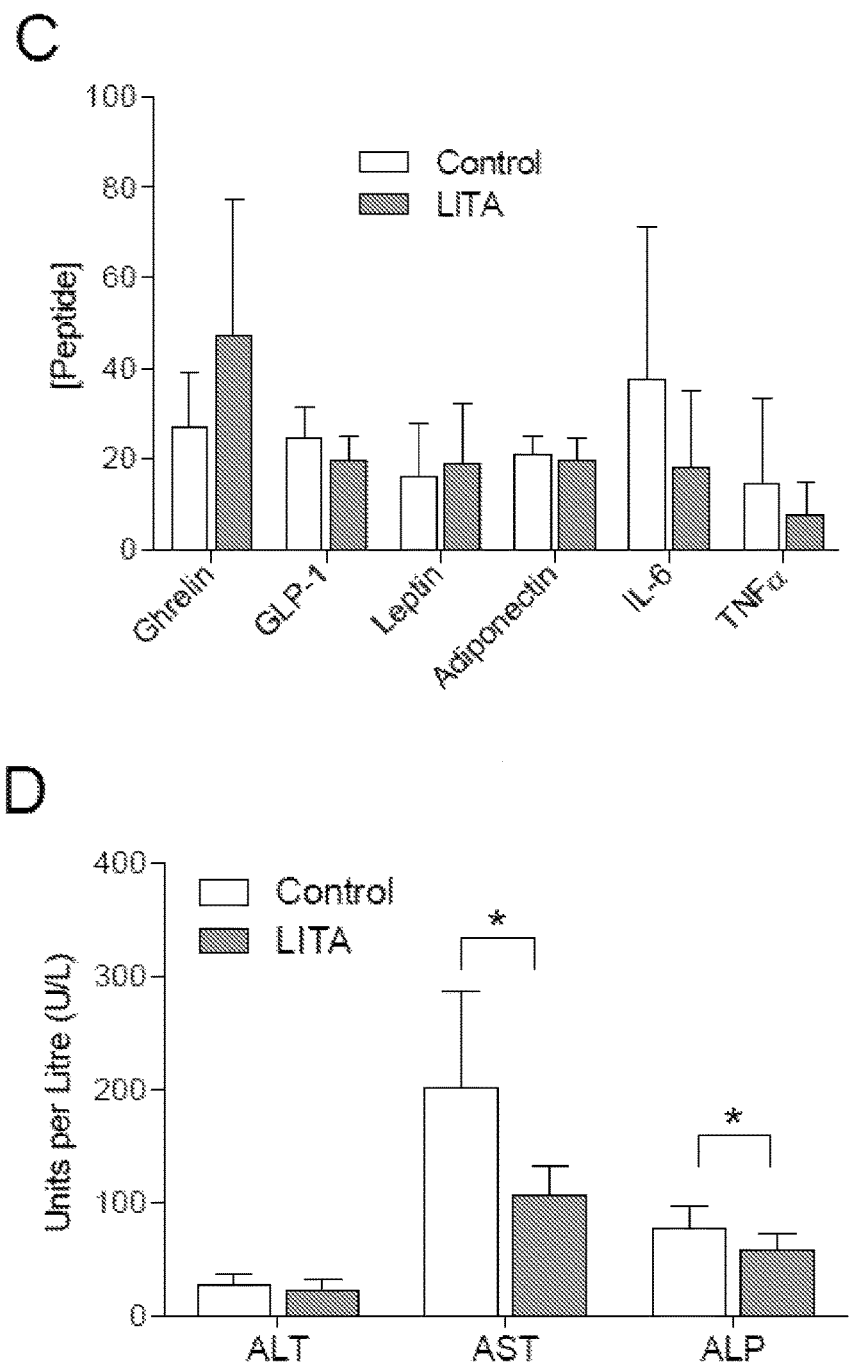

FIG. 24. The preventative effects of LITA nanoparticles in mice placed on a HFD diet. Mice were placed on a high fat diet (HFD) and injected every three days with either liposome encapsulated acetate (LITA) nanoparticles or control (HEPES) for 6 weeks. (A) Average weekly food intake (g), (B) A glucose tolerance test (GTT, glucose mmol/L per min) was performed following an overnight fast at the start of week 5 (n=10/group). (C) Additional circulating peptides (Adiponectin (ng/ml), ghrelin (ng/ml) and GIP (ng/ml) (n=6/group), Leptin (pg/ml), and interleukin-6 (pg/ml) (n=18/group), (D) Serum concentrations of 3 markers of liver function: Alanine transaminase (ALT), Aspartate transaminase (AST) and Alkaline phosphatase (ALP) (all U/L) (n=12/group); n=24/group; \*\*=p<0.01; Data analysed by 2 way ANOVA with Bonferroni post-hoc test (GraphPad Prism).

Figure 25:
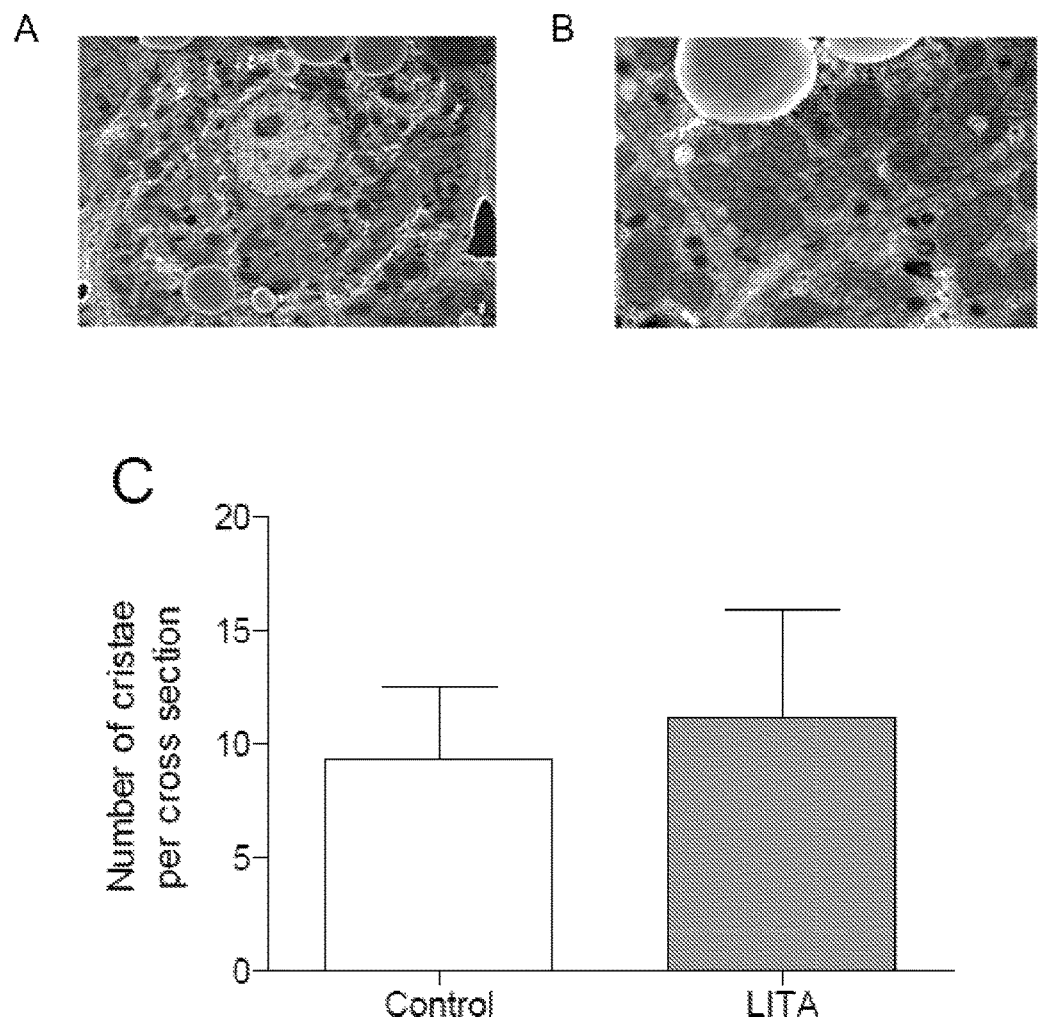
Figure 25:
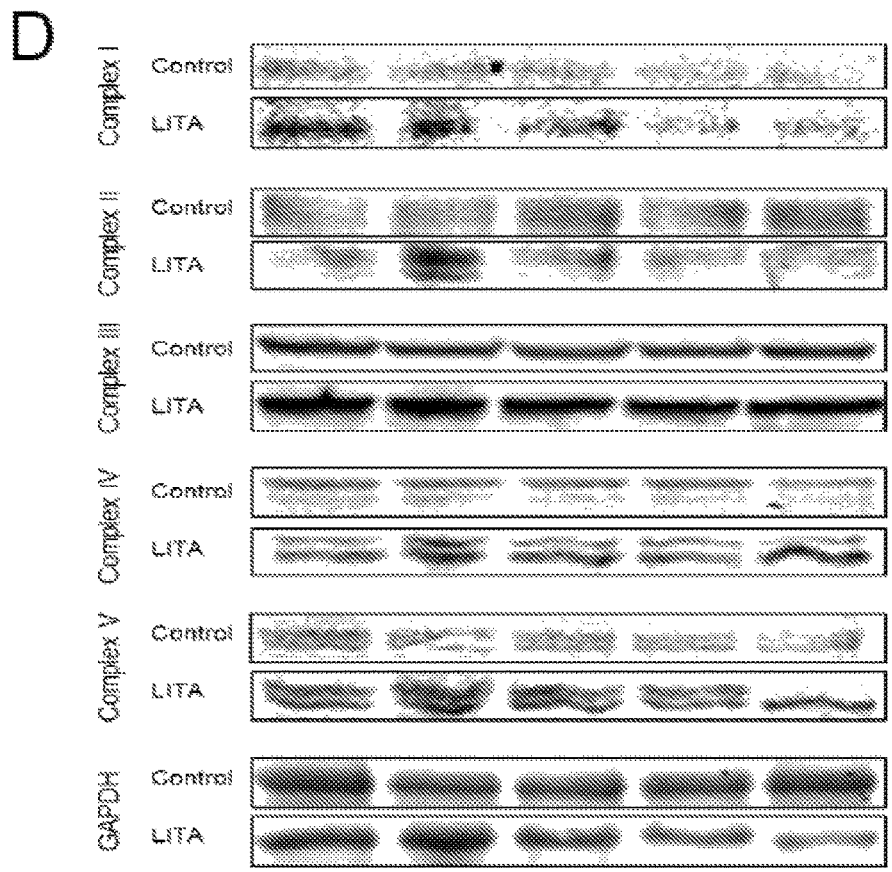
Figure 25:
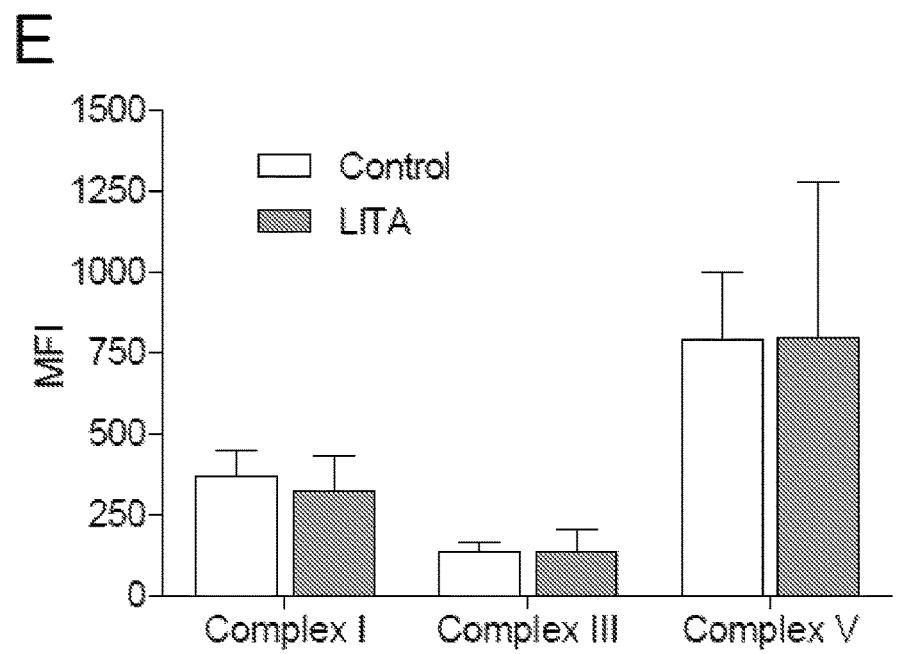

FIG. 25. The effects of chronic LITA nanoparticle administration on mitochondrial morphology and oxidative phosphorylation. Mitochondrial morphology of mice placed on a HFD and injected with either LITA or control nanoparticles for 6 weeks, (A) A representative transmission electron microscopy image (TEM) obtained at 1200× magnification used to calculate the number mitochondria, (B) A representative TEM image at 4800× magnification used to calculate the number cristae per mitochondrion, (C) Number of mitochondria per image, (D) Representative picture of WB showing mitochondrial complexes 1-V; (E) The mean fluorescence intensity (MFI) of oxidative phosphorylation complexes 1, III and V in control and LITA injected mice from Preventative NFD study; n=12/group; data analysed by 2-way ANOVA.

Figure 26:
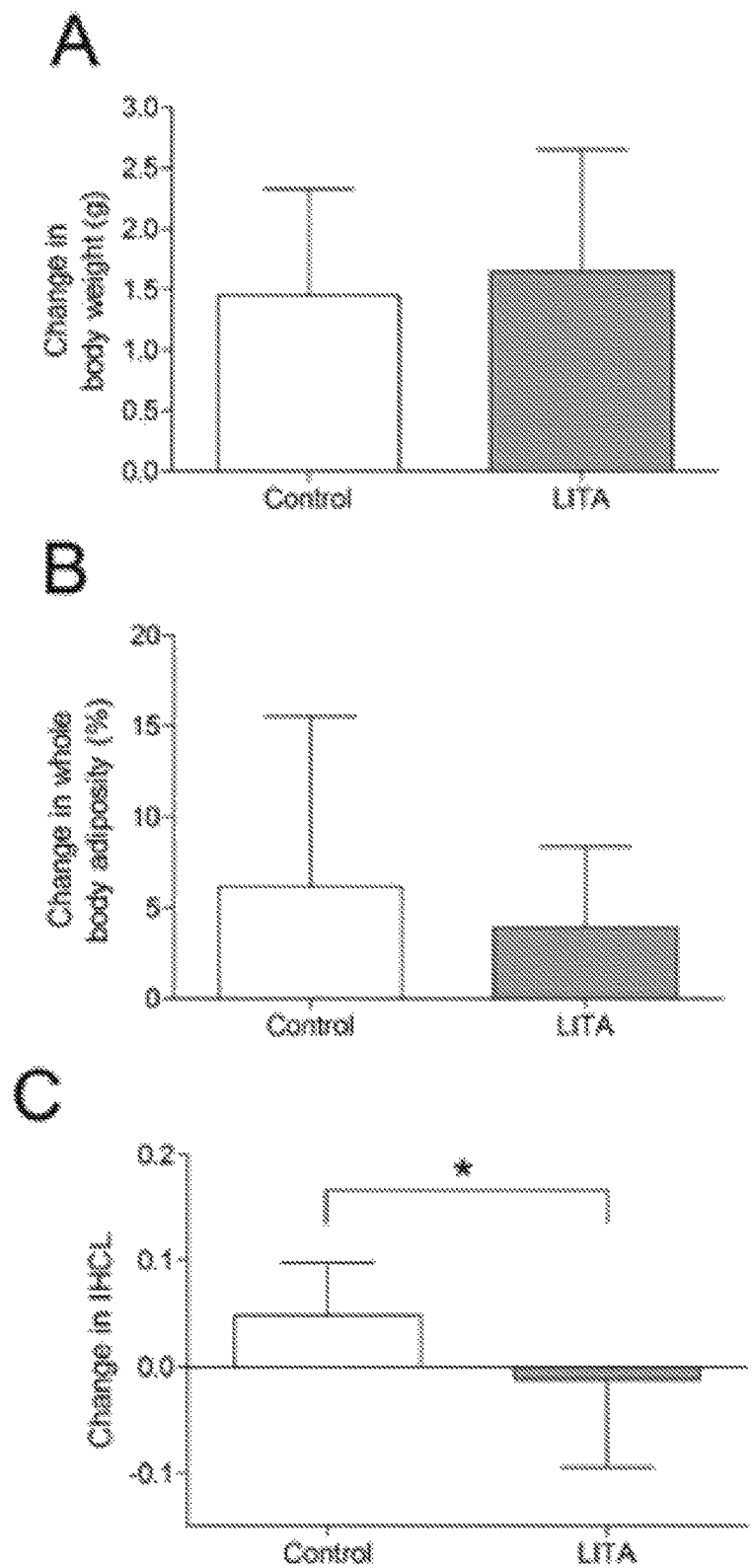
Figure 26:
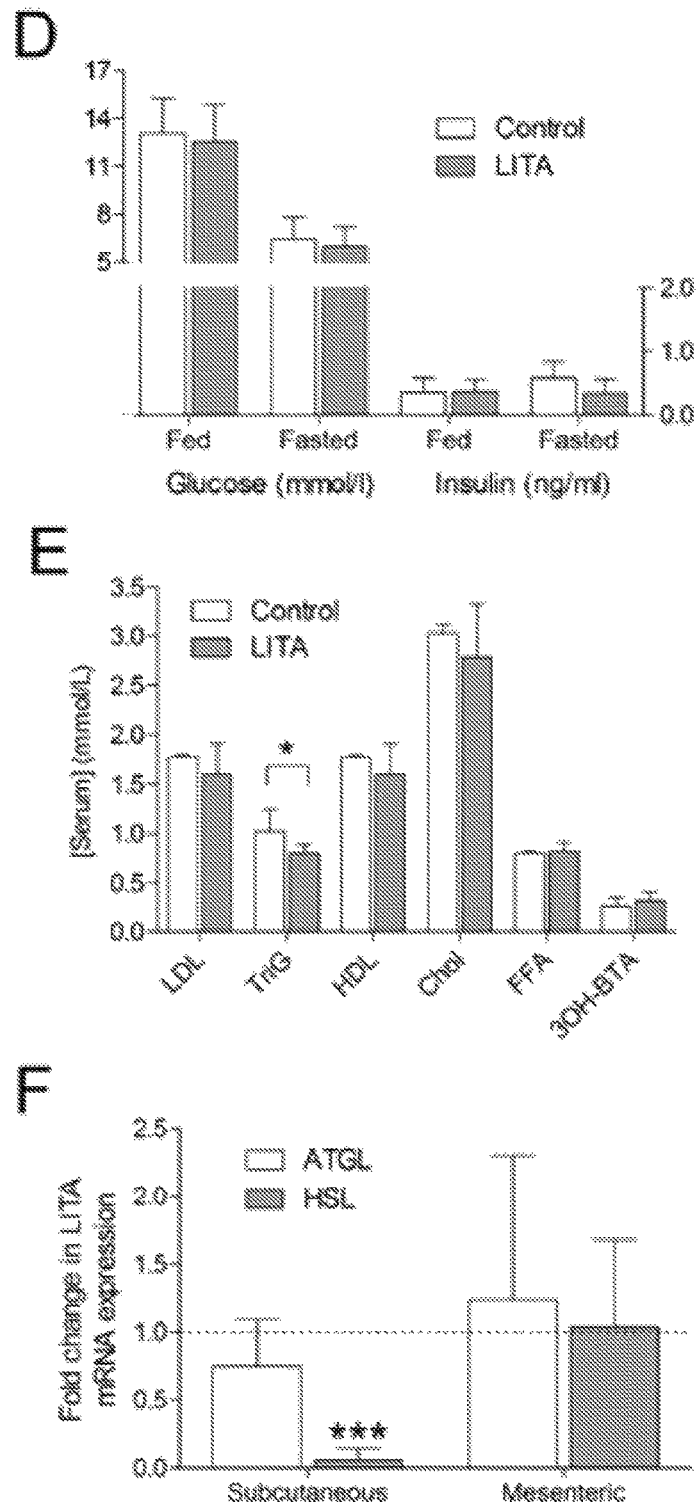
Figure 26:
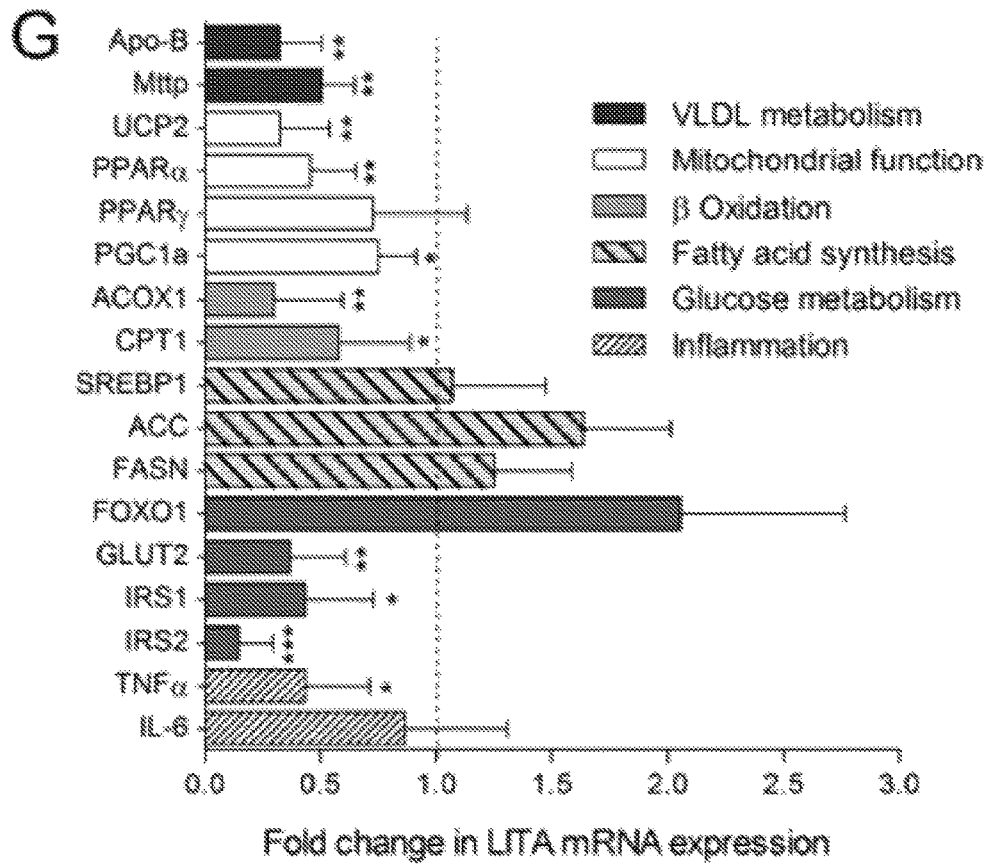
Figure 26:
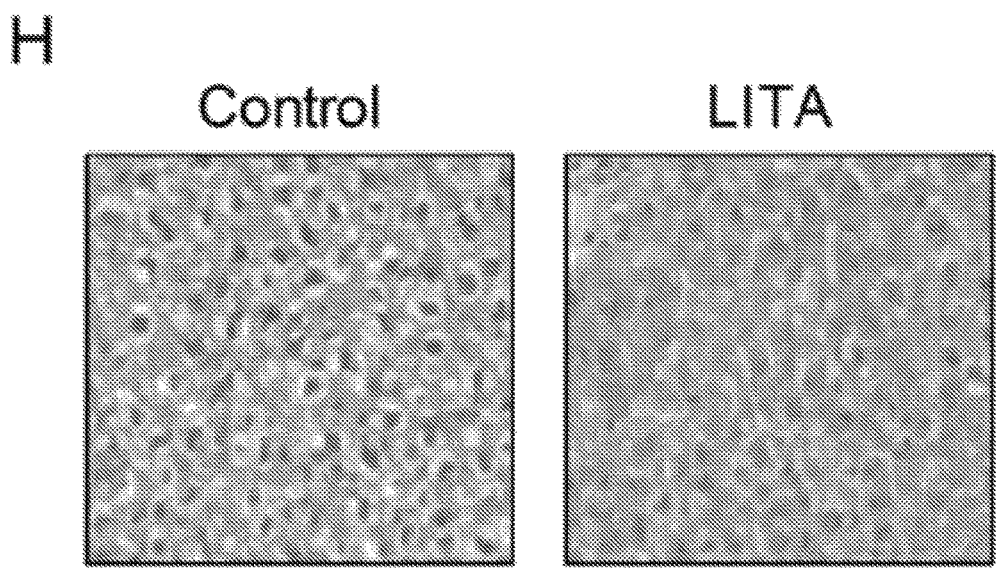

FIG. 26. The preventative effects of LITA nanoparticles in mice placed on a NFD diet. Mice were placed on a normal fat diet (NFD) and injected every three days with either liposome encapsulated acetate (LITA) nanoparticles or control (HEPES) for 6 weeks. Overall change in (A) Body weight (g), (B) Whole body adiposity (%), (C) IHCL. Fed and fasted levels of plasma (D) Plasma lipids (mmol/L) (n=6/group), (E) Fed and fasted levels of serum glucose and insulin (n=8/group), (F) Fold change in adipose tissue mRNA expression in LITA compared to control animals (n=6/group) (G) Fold change in hepatic mRNA expression in LITA compared to control animals (n=6/group), genes grouped by function. (H) H&E staining of liver cross-section. Data analysed by 2 way ANOVA with Bonferroni test for multiple comparisons (GraphPad Prism); n=24/group; \*=p<0.05, \*\*=p<0.01, \*\*\*=p<0.001.

Figure 27:
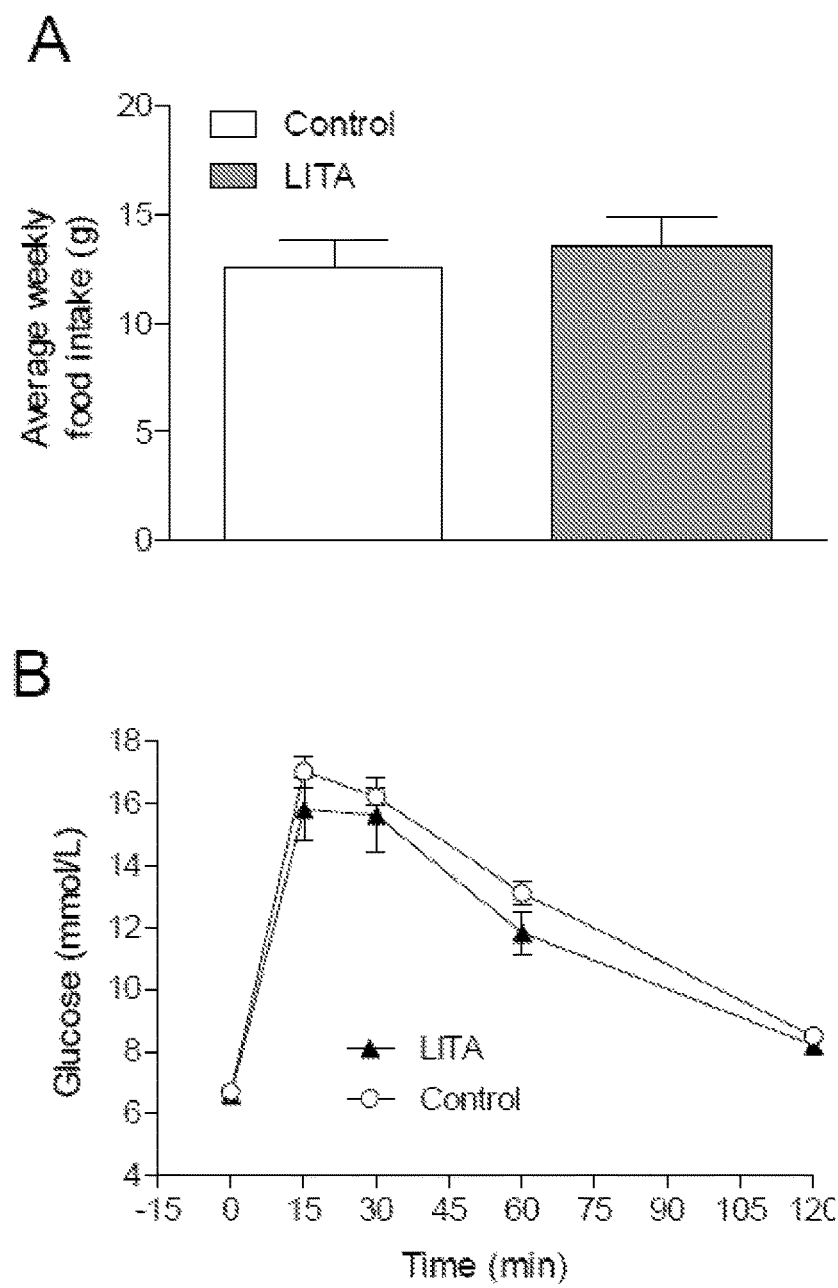
Figure 27:
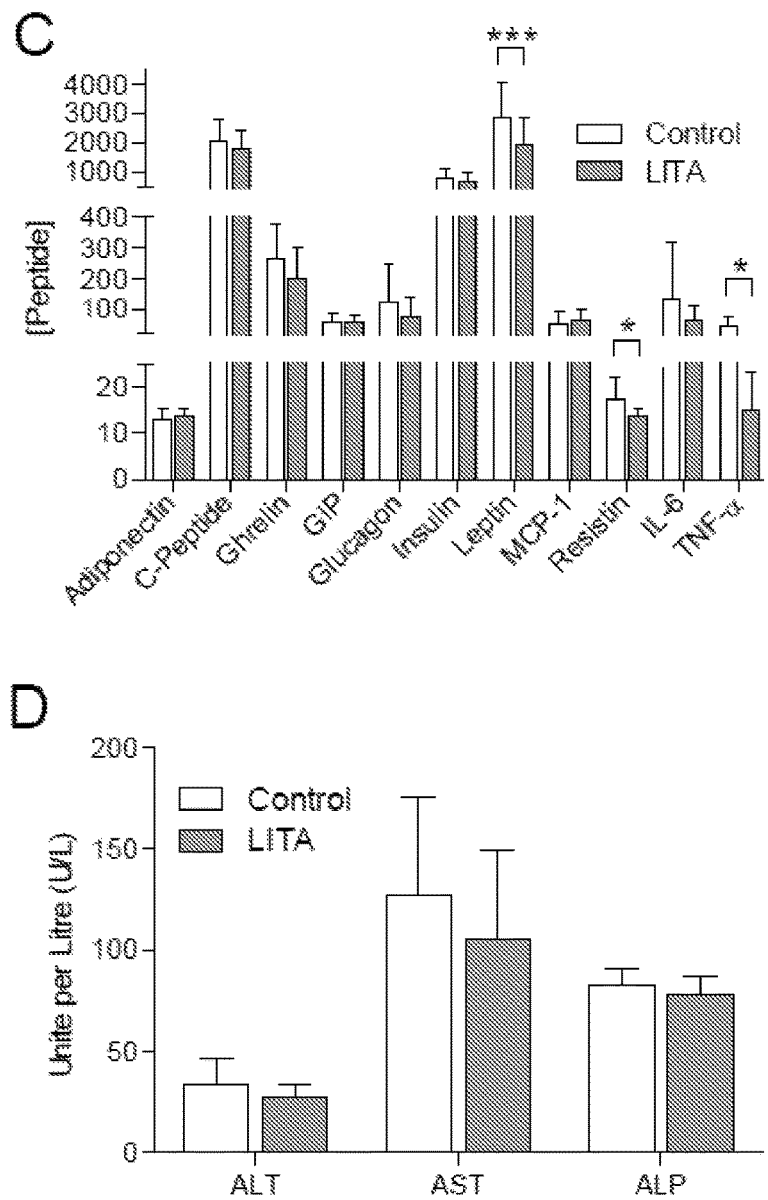
Figure 27:
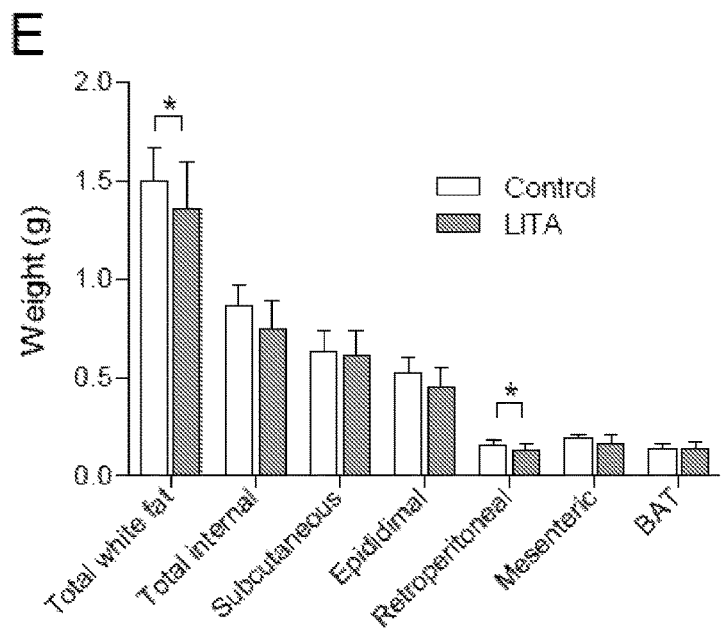

FIG. 27. The preventative effects of LITA nanoparticles in mice placed on a NFD diet. Mice were placed on a normal fat diet (NFD) and injected every three days with either LITA nanoparticles or control (HEPES) for 6 weeks. (A) Average weekly food intake (g) (n=24/group), (B) A glucose tolerance test (GTT) was performed following an overnight fast at the start of week 5 (n=10/group). (C) Additional circulating peptides (Adiponectin (ng/ml) (n=6/group), C-peptide (pg/ml), ghrelin (pg/ml), GIP (pg/ml), glucagon (pg/ml), insulin (pg/ml), Leptin (pg/ml), MCP-1 (pg/ml), Resistin (ng/ml), interleukin-6 (pg/ml) and TNF-α (pg/ml) (n=12/group), (D) Serum concentrations of 3 markers of liver function: Alanine transaminase (ALT), Aspartate transaminase (AST) and Alkaline phosphatase (ALP) (all U/L) (n=6/group). (E) Weights of adipose tissue depots (n=12/group). \*\*=p<0.01; Data analysed by 2 way ANOVA with Bonferroni post-hoc test (GraphPad Prism).

Figure 28:
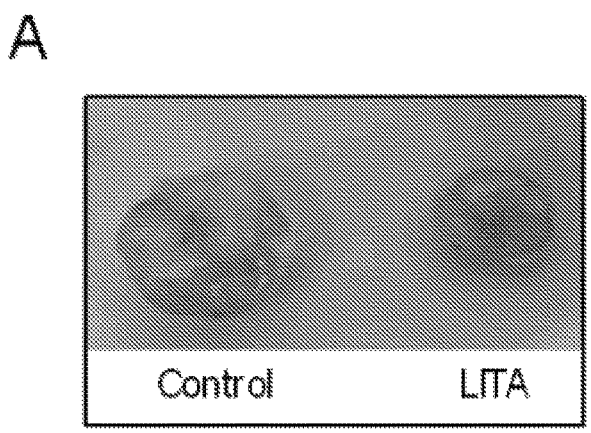
Figure 28:
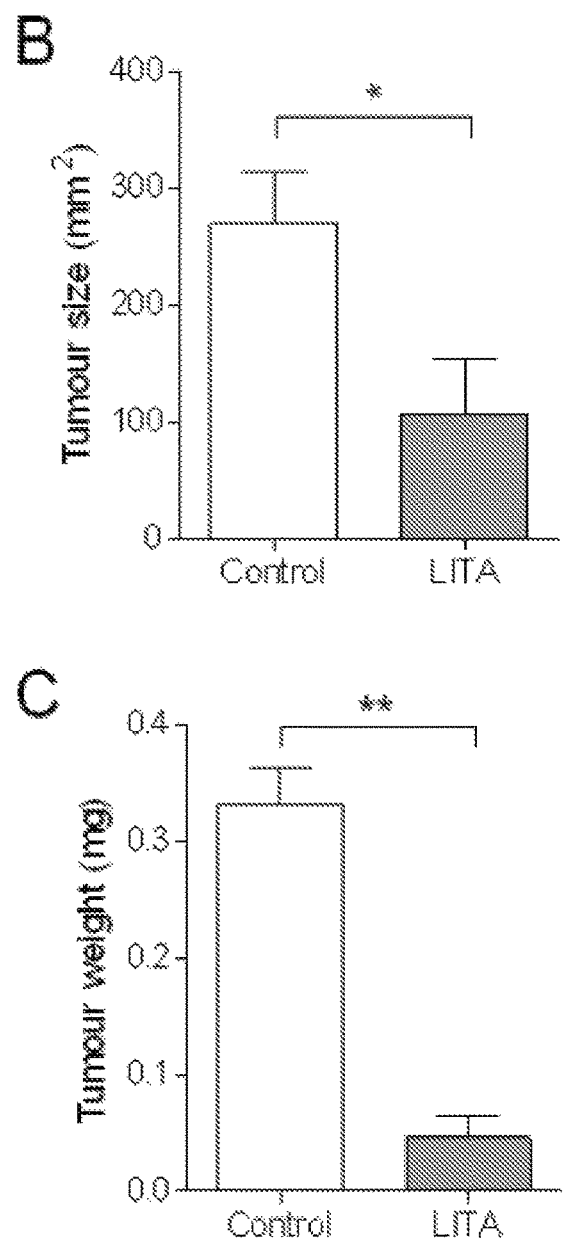
Figure 28:
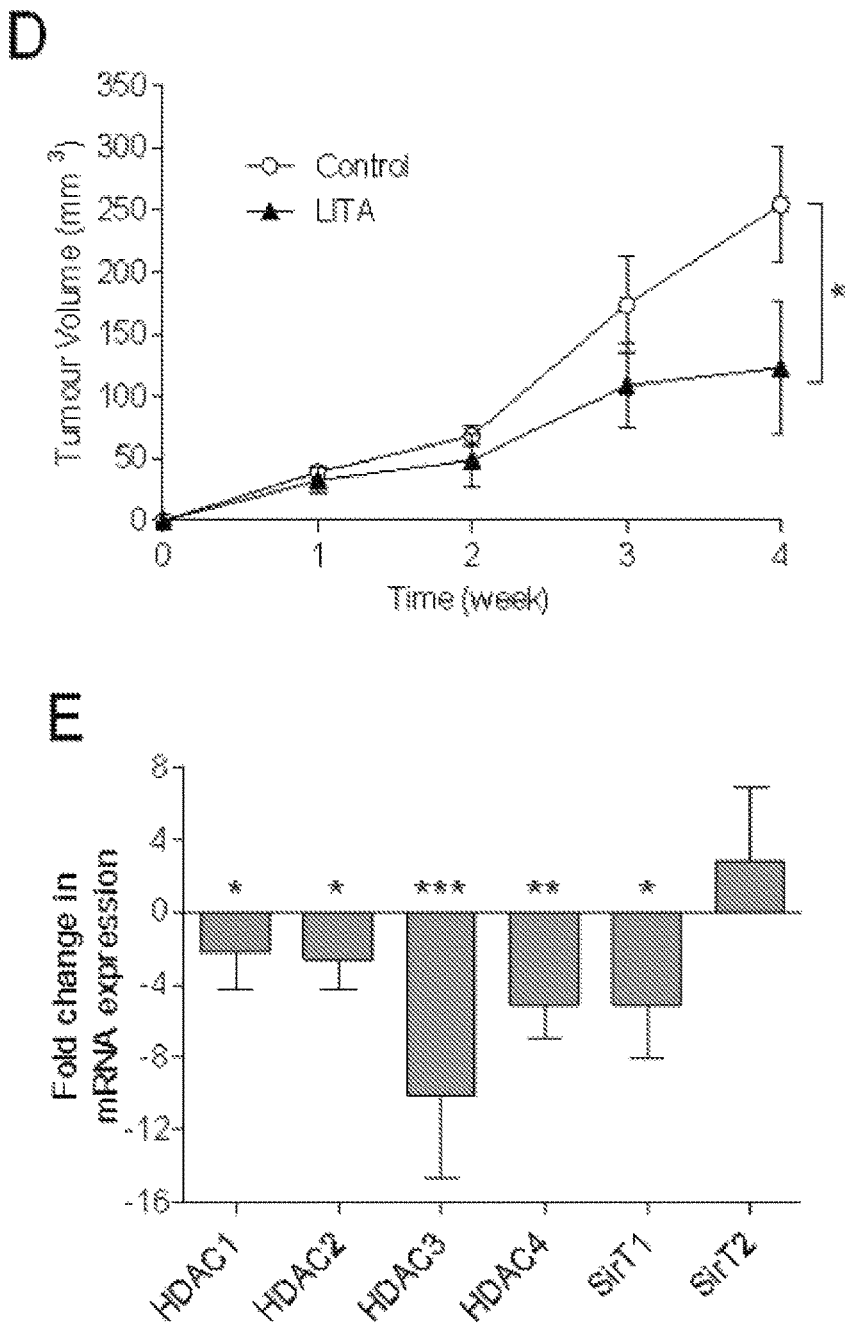

FIG. 28. The effects of LITA nanoparticles in murine HT-29 colorectal tumours. Mice were inoculated with HT-29 colorectal cancer cells and were injected every three days with either LITA nanoparticles or control (HEPES) nanoparticles for 4 weeks, once tumour was confirmed palpable. (A) Representative tumour grafts from LITA and Control injected animals, (B) Tumour size (mm2), (C) Tumour weight (mg), (D) Tumour volume (mm3) during the 4 week protocol, (E) Quantitative mRNA changes in xenograft tumour after chronic LITA administration normalized to control HEPES liposomes. Data analysed by Student's t-test or two-way ANOVA with Bonferroni post hoc test (GraphPad Prism); n=6/group; \*=p<0.05, \*\*=p<0.01, \*\*\*=p<0.001.

Figure 29:
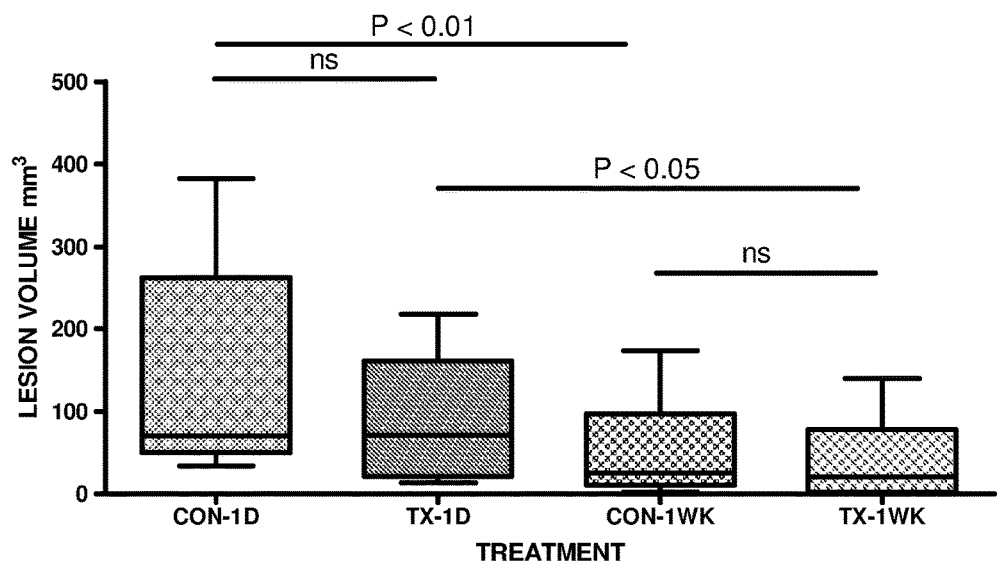

FIG. 29. MRI assessment of lesion volumes in rats treated with control (CON) or nanoparticles of Example 2 (TX): 24 h (1 D) and 1 week (1 WK) post-occlusion.

Figure 30:
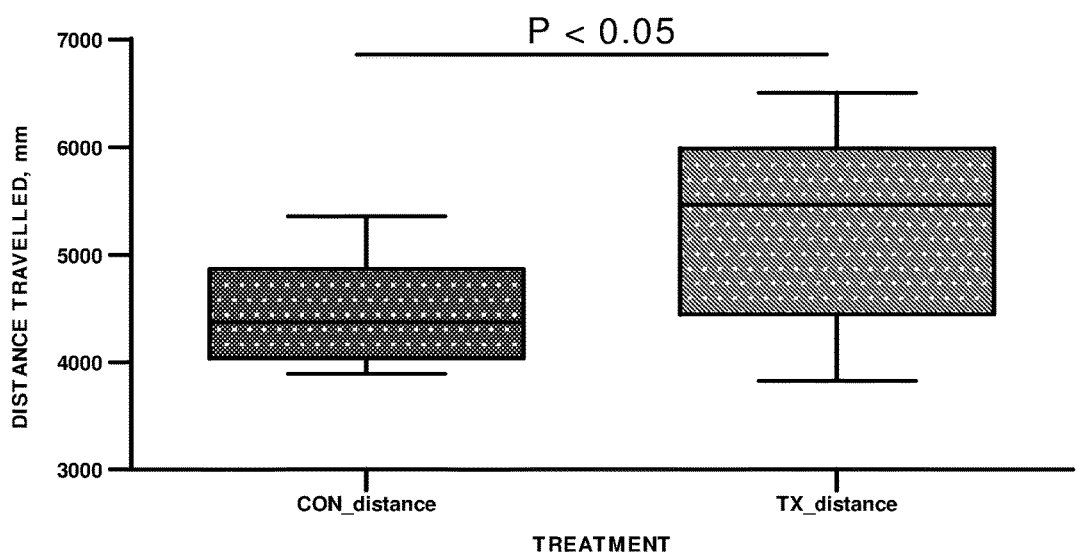
Figure 30:
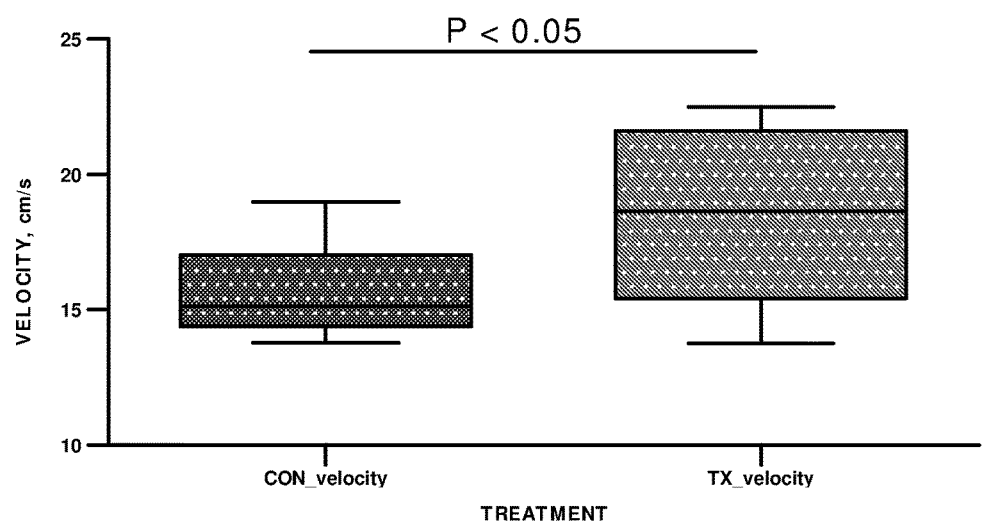

FIG. 30. (a) Distance travelled and (b) average velocity of rats receiving either the control (CON) or nanoparticles of Example 2 (TX).

EXAMPLES

Example 1

Preparation of Liposome Nanoparticles

Appropriate volumes of stock solutions of $N^1$-cholesteryloxycarbonyl-3,7-diazanonane-1,9-diamine (CDAN), 1,2-distearoyl-sn-glycero-3-phosphocholine (DSPC), cholesterol, and 1,2-distearoyl-sn-glycero-3-phosphoethanolamine-N-methoxy(polyethylene glycol)-2000 (DSPE-PEG2000) in an organic solvent (typically $CHCl_3$) were combined together in a 5 mL round bottom flask in the respective molar ratios 32:32:35:1 to produce a thin-film. This thin-film was then re-hydrated with a defined volume of 4-(2-hydroxyethyl)-1-piperazineethanesulfonic acid (HEPES) (4 mM, NaCl 135 mM, pH 6.5), sonicated to produce a lipid dispersion, buffered to pH 7, and purified by dialysis filtration to give a liposome suspension with predetermined total lipid concentrations.

Example 2

Preparation of Short-Chain Fatty Acid Encapsulated Liposomes

Appropriate volumes of stock solutions of $N^1$-cholesteryloxycarbonyl-3,7-diazanonane-1,9-diamine (CDAN), 1,2-distearoyl-sn-glycero-3-phosphocholine (DSPC), cholesterol, and 1,2-distearoyl-sn-glycero-3-phosphoethanolamine-N-methoxy(polyethylene glycol)-2000 (DSPE-PEG2000) in an organic solvent (typically $CHCl_3$) were combined together in a 5 mL round bottom flask in the respective molar ratios 32:32:35:1 to produce a thin-film. This thin-film was then re-hydrated with a defined volume of a solution of acetic acid (1M, $CH_3CO_2H$, pH 2.0), sonicated to produce a lipid dispersion, buffered to pH 7, and purified by dialysis filtration to give a liposome suspension with predetermined total lipid concentrations.

Liposome encapsulated acetate nanoparticles (also referred to herein as "LITA") were prepared, with each 1 mL solution containing approximately $10^{11}$ nanoparticles/ml. Particle sizes were determined, as shown in FIG. 1.

Example 3

Preparation of Fluorescent-Labelled Liposomes

Appropriate volumes of stock solutions of $N^1$-cholesteryloxycarbonyl-3,7-diazanonane-1,9-diamine (CDAN), 1,2-distearoyl-sn-glycero-3-phosphocholine (DSPC), cholesterol, 1,2-dioleoyl-sn-glycero-3-phosphoethanolamine-N-(lissamine rhodamine B sulfonyl) (DOPE-Rhodamine), and 1,2-distearoyl-sn-glycero-3-phosphoethanolamine-N-methoxy(polyethylene glycol)-2000 (DSPE-PEG2000) in an organic solvent (typically $CHCl_3$) were combined together in a 5 mL round bottom flask in the respective molar ratios 32:32:34:1:1 to produce a thin-film. This thin-film was then re-hydrated with a defined volume of 4-(2-hydroxyethyl)-1-piperazineethanesulfonic acid (HEPES) (4 mM, NaCl 135 mM, pH 6.5), sonicated to produce a lipid dispersion, buffered to pH 7, and purified by dialysis filtration to give a liposome suspension with predetermined total lipid concentrations.

To produce short-chain fatty acid encapsulated liposomes which comprise fluorescent labels, the procedure of Example 2 may be conducted with the lipid composition of Example 3.

Example 4

Encapsulation of Acetate at Varying Concentrations

Nanoparticles according to Example 2 were prepared using varying concentrations of acetate. The concentrations of acetate employed were 1 mM, 10 mM, 100 mM and 1M. The resultant particle size distributions of the nanoparticles produced are illustrated in FIG. 1. Once prepared, the amount of acetate encapsulated was quantified for each concentration and the results are illustrated in FIG. 2. These figures show that a range of nanoparticle sizes may be produced with a range of acetate concentrations encapsulated therein.

Example 5

Varying Lipid Compositions

Nanoparticle formulations comprising encapsulated acetate were prepared according to Example 2.
a) The amount of CDAN was varied from 10% to 32% and 50%. The nanoparticle size distributions are shown in FIG. 3, where it can be seen that increasing the amount of CDAN results in a decrease in the particle size distribution. FIG. 4 shows the 1H-NMR quantification of acetate in the nanoparticles formulated with varying levels of CDAN, and it can be seen that each result in encapsulated acetate. However, molar ratios in the region of 30% proved more effective.
b) The amount of component (ii) (DSPC) was varied from 10% to 32% and 50%. The nanoparticle size distributions are shown in FIG. 5, where it can be seen that increasing the amount of DSPC results in a broader particle size distribution, yet spread over smaller absolute particle sizes. FIG. 6 shows the $^1$H-NMR quantification of acetate in the nanoparticles formulated with varying levels of DSPC, and it can be seen that each result in encapsulated acetate. However, molar ratios in the region of 30% proved more effective.
c) The nature of component (ii) was varied from DSPC to DOPE and DLPC. The nanoparticle size distributions are shown in FIG. 7, where it can be seen that both DOPE and DLPC provide broader particle size distributions from approximately 30 to 100 nm. FIG. 8 shows $^1$H-NMR quantification of acetate in the nanoparticles formulated with these components, and it can be seen that acetate is encapsulated in both cases, albeit at a lower level than DSPC.
d) The amount of component (iii) was varied from 1% to 10%. The nanoparticle size distributions are shown in FIG. 9, where it can be seen that 10% cholesterol provides a very broad particle size distribution compared to 1%. FIG. 10 shows $^1$H-NMR quantification of acetate in the nanoparticles formulated with these components, and it can be seen that acetate is encapsulated in both cases.
e) The nature of component (iv) (DSPE-PEG) was varied in terms of the PEG group from a molecular weight of 2000 to 5000. The nanoparticle size distributions are shown in FIG. 11, where it can be seen that an increase in molecular weight to 5000 results in the formation of smaller nanoparticles compared to a molecular weight of 2000. FIG. 12 shows $^1$H-NMR quantification of acetate in the nanoparticles formulated with these components, and it can be seen that acetate is encapsulated in both cases to a similar extent.

Example 6

Nanoparticle Formulation and Thermo-Stability Characteristics

Nanoparticle formulations comprising encapsulated acetate were prepared according to Example 2, and the particle size stability (i.e. stability against aggregation) of the nanoparticles under different temperature conditions of either hot (35° C.) or cold (4° C.) temperature incubations for 18 hours before and after dialysis filtration were tested. Compared to FIGS. 1 and 2 (1 M acetate formulated according to Example 2 at room temperature) the results in FIG. 13 show that formation of the nanoparticles at room temperature within a reasonable timescale is optimal. In addition, $^1$H-NMR quantification in FIG. 14 illustrates that cold dialysis filtration (approximately 4° C.) was able to improve acetate retention over time within the nanoparticles.

Example 7

Biodistribution Studies in the Liver

Nanoparticles were prepared with rhodamine lipid incorporated therein as described in Example 3 and then administered to mice. Liver histology was performed on mice liver 2 h post standard dose administration (200 μL). Detection of the nanoparticles was confirmed through rhodamine fluorescence. DAPI (4',6-diamidino-2-phenylindole) staining was used to demonstrate the presence of intact hepatocytes within the field of view. Fluorescence filters were used to eliminate non-specific background fluorescence or other non-specific assay artefacts. Data demonstrate that the nanoparticles concentrate in the liver and mediate functional delivery of acetate to liver hepatocytes. In particular, the data suggests that cationic lipids (e.g. CDAN) are beneficial for functional delivery of encapsulated acetate to the liver.

Example 8

In vivo Xenograft Model for Colorectal Cancer

The desired cell line was seeded at 2.5×10$^5$ cells per T-25 flask (Nunc, USA) and grown as a monolayer in Dulbecco's Modified Eagle Medium (DMEM) (Sigma-Aldrich, UK), supplemented with 10% fetal calf serum (FCS) (Sigma-Aldrich, UK) in an incubator at 37° C. with 5% $CO_2$. Cells were maintained every 3-5 days while never exceeding 15 passages. Once the cells were approximately 80% confluent, the media was removed, they were harvested by removal of the media, washing with PBS, and followed by the addition of trypsin (Sigma-Aldrich, UK) for approximately 5 minutes. The media was removed and cells were washed with PBS three times and re-suspended in serum-free DMEM and centrifuged at 1,000 RPM for 5 minutes. The media was removed and cells were counted on a haemocytometer.

Colon cancer cell line HT-29 was prepared and injected into balb/c nude mice subcutaneously into the right flank with 5×10$^6$ cells in 100 μl of serum-free media, using a 25 gauge needle. Tumour bearing mice were divided into groups to receive a 200 μl, adminstration intraperitoneally of either the nanoparticle formulation according to Example 2 or the control nanoparticle which contained approximately 5×10$^8$ liposomes per injection (n=8). Identification of subcutaneous nude mouse xenograft tumours required 14 to 20 days. Once tumours were palpable, chronic injections were administered every three days and in parallel the tumours were measured by calliper to determine the volume estimated assuming an ellipsoid shape using the following equation: volume=length×width×depth×π/6.

The growth curve of the xenograph tumour model (FIG. 15) shows the group receiving the nanoparticle formulation of Example 2 exhibited a significant reduction in growth when compared to the control group (p<0.001). The difference in treatment groups provided substantial and confident findings that this novel nanoparticle has anti-tumour properties for colorectal cancer in particular.

Results are presented as mean±standard error of the mean (SEM) and 'n' refers to the number of animals or biological replicated per group. Analysis was carried out in GraphPad Prism version 4 (GraphPad Software, USA). Two-way ANOVA was applied for data analysis and statistical significance was regarded as P values <0.05.

Example 9

Reduction in Accumulated Weight Gain and Whole Body Adiposity

Pre-clinical relevance of the formulation according to Example 2 was carried out using an in vivo model over a 10 week period. Mice were grouped 4 per cage in individually ventilated cages (IVCs) at 22° C., 70% humidity and a 12:12 (6.30 am-6.30 pm) light:dark cycle. Mice had ad libitum access to water and at 5 weeks of age were placed on a high fat diet of 60% by kcal intake, which was provided by SSNIFF (England, UK) and is outlined below (Table 1).

TABLE 1

|  | High fat diet |
| --- | --- |
| Crude fat | 34 |
| Crude protein | 24.1 |
| Crude fibre | 6 |
| Crude ash | 6.1 |
| Starch | 2.2 |
| Sugar | 22.4 |
| Energy | 21.4 MJ ME/kg |

Mice were kept on a high fat diet for 5 weeks, during which time food intake and weight gained were monitored at least 3 times a week. At 5 weeks of age, the mice received chronic delivery of the nanoparticles of Example 2 or the control HEPES-containing nanoparticles by intraperitoneal injection every three days for another 5 weeks. The injection volume was 200 μL, which contained approximately 5×10$^8$ nanoparticles per injection. Mice remained on the high fat diet for the duration of the nanoparticle therapy. At week 5 and week 10, whole body adiposity was determined by $^1$H MRS (magnetic resonance scanning). This was carried out for the pre- and post-scan fat content to determine in vivo if the nanoparticles had an effect on whole body adiposity while consuming a high fat diet.

Prior to the scans, animals were fasted overnight for 16-18 hours. For the scan, mice were anaesthetised with 2-3% isoflurane 2/min oxygen, placed prone into the RF coil with the liver at the centre of the coil and scanned on a 4.7 T Unity Inova MR scanner (Varian Inc, USA). During the scan, a breathing pad was used to monitor respiration rate and a rectal probe was used to measure core temperature, which was maintained at 37° C. with a warm air blower.

The field homogeneity was optimised by shimming on the water signal of the whole mouse. A three plane scout image was taken in order to plan a series of contiguous axial slices over the mouse abdomen to give full liver coverage. Localised $^1$H liver MRS was performed using a PRESS sequence with a voxel 2×2×2 mm$^3$ placed using whole body MRI (magnetic resonance imaging) with the following parameters: TR 10 s, TE 9 ms, averages 64 and spectral width 20,000 Hz. Total scanning time was approximately 30 minutes per animal. Statistical analysis for determining IHCL using $^1$H liver MRS was carried out using MestRe-C software.

At the end of the 10 weeks there was a reduction in accumulative weight gain in the nanoparticle-administered group when compared to the control group, as illustrated in FIG. 16. In addition to weight reduction there was also a decrease in whole body adiposity, as shown in FIG. 17. This data concludes that even while remaining on a high fat diet, the nanoparticles protected against the increase in whole body adiposity that was influenced by the diet, as shown in the control group. Reductions were a result of the treatment properties of the nanoparticles.

Example 10

Nanoparticle Preparation and Bio-Distribution

Various imaging modalities were employed to confirm the passive, non-targeted delivery of the liposomal vector to both the liver and malignant tissue. Liposomal conjugations were distinguished by their encapsulated products or moieties introduced into the lipid bilayer (Table 2).

TABLE 2

| Molar Component (%) | DSPC | CDAN | Cholesterol | DSPE PEG$^{2000}$ | DOPE Rhodamine | Gadolinium DOTA DSA |
|---|---|---|---|---|---|---|
| (1) LIP | 32 | 32 | 35 | 1 | — | — |
| (2) LIP-XG | 32 | 32 | 31 | 5 | — | — |
| (3) LIP-Rhd | 32 | 32 | 34 | 1 | 1 | — |
| (4) LIP-XG-Rhd | 32 | 32 | 30 | 5 | 1 | — |
| (5) LIP-Gd | 32 | 32 | 34 | 1 | — | 1 |

Description of Table 2: (1) LIP: Standard liposome conjugation used for the encapsulation of 18F-FDG, acetate and HEPES; (2) LIP-XG: Liposomes conjugated with a higher DSPE PEG2000 percentage to increase tumour uptake in animal models of malignancy; (3) LIP-Rhd: Liposomes contained 1% of rhodamine (Rhd), a fluorescent lipid used for histological analysis; (4) LIP-XG-Rhd: LIP-XG contained an additional 1% of rhodamine for histological analysis. (5) LIP-Gd: Liposomes conjugated with gadolinium (Gd) for use in MRI bio-distribution analysis; LIP: Liposome; LITA: Liposome encapsulated acetate; DSPC: 1,2-distearoyl-sn-glycero-3-phosphocholine; CDAN: N1-cholesteryloxycarbonyl-3,7-diazanonane-1,9-diamine; DSPE PEG2000: 1,2-distearoyl-sn-glycero-3-phosphoethanolamine-N-methoxy (polyethylene glycol)-2000; DOTA: gadoterate meglumine; DOPE—Rhodamine:1,2-dioleoyl-sn-glycero-3-phosphoethanolamine-N-(lissamine rhodamine B sulfonyl); DSA: digital subtraction angiography.

Short term biodistribution was assessed in C57BL/6 mice following intraperitoneal (i.p.) injection with free 18F-FDG or 18F-FDG encapsulated liposomes (LIP-FDG). Representative PET, CT and PET/CT fusion images from the LIPFDG group acquired 30 min post-injection are shown in FIG. 1.8A. Liposomal delivery of 18FFDG was achieved in all tissue including liver, kidney and muscle. Interestingly, increased 18F-FDG uptake was observed in the heart and muscle (FIG. 18B). Tissue-specific accumulation of liposomes conjugated with rhodamine (LIP-Rhd) was examined using histological techniques (FIG. 18C-G). The highest concentrations of LIP-Rhd were observed in the liver and spleen, with lower quantities in the heart, kidneys, and brain (Table 3).

TABLE 3

| | Liver | Spleen | Kidney | Lungs | Heart | Brain | Muscle | Pancreas |
|---|---|---|---|---|---|---|---|---|
| 2 h | Y | Y | Y | Y | Y | Y | — | Y |
| 16 h | Y | Y | Y | — | Y | Y | — | Y |
| 24 h | Y | Y | Y | — | — | Y | — | Y |
| 48 h | Y | Y | — | — | — | Y | — | — |

Description of Table 3: Mice were injected i.p. with 200 µl of LIP-Rhd nanoparticle solution. Organs were collected and stained for rhodamine at 2, 16, 24 and 48 h post injection (n=3/time point); indicates the presence (Y) or absence (–) of rhodamine at these time points.

Xenograft uptake of nanoparticles formulated for enhanced delivery to malignant tissue is shown in FIG. 18H. Long-term nanoparticle accumulation was assessed by tracking biodistribution of liposomes formulated with lipid-gadolinium complexes embedded in the lipid membrane (LIP-Gd) using magnetic resonance imaging (MRI). Following a baseline scan, mice received i.p. injection of either LIP-Gd or control and scanned 24 h and 48 h post-injection. T1 changes in the liver, kidney, and subcutaneous fat are shown in FIG. 18I-K, respectively. Nanoparticles accumulated preferentially in the liver, indicated by the significant reduction in T1, at 24 h and 48 h post-injection (24 h: LIP-Gd: 495.9±37.4 msec, Control: 804.1±81.8 msec; p<0.05; 48 h: LITA-Gd: 503±66 msec, Control: 738±80 msec; p<0.05).

Example 11

Liposomal Encapsulated Acetate Formulation and Quantification

Following confirmation of preferential uptake in target tissues, liposomes were encapsulated with either acetate ("LETA" from Example 2), or low ionic strength buffer (HEPES) as control. LITA formulations and a liposome-free acetate solution were prepared +/−albumin, which is known to bind acetate, reducing its NMR signal. Albumin suppressed the NMR signal for acetate in free solution, whereas no reduction was observed in LITA nanoparticle solution (FIG. 19A-D); indicating acetate was successfully encapsulated within the liposome. To enable quantification of liposomal acetate, LITA formulations were scanned with a known concentration of lactate, as an internal standard. Liposomal acetate concentration was calculated as 26.45 µg (2.2 mM) per 100 µl (FIG. 19E-F). The concentration of acetate per LITA-injection was 2.6 mg/kg, an order of magnitude lower than previously used for intragastric or oral delivery in murine models. There was no difference in size between liposomal formulations (LITA: 102.3±7.5 nm; Control: 95.9±9.0 nm, p=0.6, FIG. 19G-I).

Example 12

In Vitro Effects of Acetate on Mitochondrial Respiration

In vitro mitochondrial respiration was assessed to determine if acetate was used as an energy source, at a concentration comparable to the dosage used with LITA protocols (2.2 mM per 100 µl injection). Acetate (5 mM) was found to significantly increase ATP production (p<0.01) (FIG. 20).

Example 13

Reparative Effects of Chronic LITA-Nanoparticle Administration in C57BL/6 Mice on a High Fat Diet The metabolic potential of LITA nanoparticles (Example 2) was assessed in multiple in vivo models, examining different metabolic outcomes. In the first, an obesogenic background was established by placing mice on a high fat diet (HFD) for 5 weeks. Mice subsequently received i.p. injection of LITA or control nanoparticles every 3 days for a further 5 weeks, while maintained on a HFD. The differences in body weight (FIG. 21A) or cumulative food (FIG. 21B) were observed between groups. Whole body adiposity and IHCL were determined by 1H MRS after the initial 5 weeks of HFD, and again following 5 weeks of chronic injections. Whole body adiposity (LITA: 9.0±16.7%; Control: 40±21.8%, p=0.02) (FIG. 21C) and IHCL (LITA: −0.11±0.06, Control: 2.4±0.9, p<0.0001) (FIG. 18D) were significantly reduced in LITA treated animals. White adipose tissue (WAT) was also reduced (LITA: 3.4±1.2 g, Control: 4.3±1.2 g, p<0.01), while brown adipose tissue (BAT) levels showed less change (FIG. 22A). The changes in circulating glucose, insulin or lipids were observed (FIG. 21E). LITA injected animals did demonstrate reduced serum chemokine KC/GRO (p<0.05), signifying reduced inflammatory tone, and increased IL-10 (p<0.05) (FIG. 21F), a marker for the inhibition of pro-inflammatory cytokine production. Quantitative RT-PCR of liver mRNA revealed significant reduction in UCP-2 expression in LITA treated animals (FIG. 21G). RT-PCR liver analysis demonstrated a LITA-induced reduction in HDAC1 expression (p<0.001) (FIG. 21G), while western blot analysis showed a significant difference in HDAC2 (p<0.01) and HDAC7 (p<0.001) (FIG. 21H). Normalisation of histone lysine proteins to total histone protein expression revealed a reduction in residue acH4K12 in the LITA group (FIG. 21I). Microarray analysis also confirmed significant changes in expression of metabolic related genes, including the HDAC class 1 (FIG. 22B).

Example 14

Preventative Effects of Chronic LITA-Nanoparticle Administration in C57BL/6 Mice in HFD In the second dietary model, the potential of LITA nanoparticles (Example 2) to prevent the development of outcomes associated with an obesogenic diet was assessed. Mice placed on a HFD received i.p. injections of LITA or control nanoparticles every 3 days for 6 weeks. The differences in body weight (FIG. 23A) or weekly food intake (FIG. 24A) were observed. In accord with the previous model, chronic LITA treatment significantly reduced accumulation of adiposity (LITA: 24.1±9.7%; Control: 30.8±9.7%, p=0.03) (FIG. 23B) and IHCL (LITA: −0.01±0.7, Control: 0.03±0.05, p=0.05) (FIG. 23C). LITA injection reduced serum insulin levels (LITA: 0.6±0.3 ng/ml, Control: 1.1±0.7 ng/ml, p<0.05), and elevated fasting glucose (LITA: 8.6±1.8 mmol/L, Control: 7.4±1.5 mmol/L, p=0.02) (FIG. 23D). A trend towards reduced glucose clearance was seen in LITA-injected mice following a glucose tolerance test (GTT) (FIG. 24B). The differences in insulin sensitivity were observed using the homeostatic model assessment (HOMA) index (LITA: 6.1±2.5, Control: 6.7±2.3, p=NS). There was also a trend toward reduced serum inflammatory markers in LITA-treated animals (TNF-α: LITA: 5.4±3.4 pg/ml, Control: 10.6±8.5 pg/ml, p=0.06; IL-6: LITA: 17.4±17.6 pg/ml, Control: 39.7±35.5 pg/ml, p=0.06) (FIG. 24C). There were minimal differences in serum lipid concentrations (FIG. 23E), despite LITA-injected mice presenting reduced subcutaneous adipose tissue (SAT) mRNA expression of adipose triglyceride lipase (ATGL) (p<0.01) (FIG. 23F), suggestive of a reduced mobilisation of peripheral lipids. There was a notable decrease in serum free fatty acids (FFA) in LITA-injected animals (LITA: 0.36±0.08 nmol/L, Control: 0.75±0.2 nmol/L, p<0.05), while serum concentration of the ketone, 3-hydroxybutyrate, were increased (LITA: 0.29±0.1 nmol/L, Control: 0.18±0.03 nmol/L, p<0.05) (FIG. 23E). Hepatic function was assessed via standard liver function tests and quantitative RT-PCR of mRNA. A decrease in serum levels of the liver function markers aspartate aminotransferase (AST) and alkaline phosphatase (ALP) was observed in LITA-injected animals (AST: LITA: 106±26 U/L, Control: 201±87 U/L, p=0.02 and ALP: LITA: 57.5±14 U/L, Control: 76.9±20 U/L, p=0.02) (FIG. 24D). Chronic LITA injection also led to a significant reduction in mRNA expression of genes involved in fatty acid synthesis (FAS); including sterol regulatory element-binding protein-1 (SREBP1), acetyl coenzyme-A carboxylase (ACC) and fatty acid synthase gene (FASN) (FIG. 23G). LITA administration also led to a significant reduction in mRNA expression of genes responsible for both β-oxidation; carnitine palmitoyltransferase-1 (CPT1), acyl coenzyme-A oxidase-1 (ACOX1), and VLDL synthesis; microsomal triglyceride transfer protein (Mttp) (FIG. 23G). In accord with the previous HFD model, LITA-injected mice demonstrated reduced levels of UCP-2 (FIG. 23G). Furthermore, LITA treated mice demonstrated reduced microvacuolation in the liver compared control treated mice (FIG. 23H). Transmission electron microscopy analysis of hepatic mitochondrial morphology revealed no difference in mitochondrial number (FIG. 25A-C) but a trend towards increased cristae/perimeter length in LITA-injected mice (p=0.07, FIG. 23I). Significant increases in protein expression of oxidative phosphorylation complex III (+62%), IV (+91%) and V (+69%) were observed in LITA animals (FIG. 23J and FIG. 25D). Chronic LITA injection led to a reduction in hepatic expression in forkhead box protein O1 (FOXO1) mRNA (FIG. 23G), indicative of reduced gluconeogenesis. Furthermore, a reduction in hepatic uptake of glucose was also observed following LITA administration, shown by reduced glucose transporter 2 (GLUT2) mRNA (FIG. 23G), and increased fasting glucose (FIG. 23D), without a concomitant difference in food intake.

Example 15

Preventative Effects of Chronic LITA Nanoparticle Administration in C57BL/6 Mice Placed on a Normal Fat Diet (NFD)

The next model assessed the effects of LITA delivery on a normal dietary background. Mice placed on a NFD received i.p. injections of LITA (Example 2) or control nanoparticles every 3 days for 6 weeks. The differences in body weight (FIG. 26A) or weekly food intake (FIG. 27A) were observed. The differences in whole body adiposity were observed (LITA: 3.9±4.4%, Control: 6.6±9.1%, p=NS) (FIG. 26B). A significant reduction in IHCL was seen in LITA injected mice (LITA: −0.01±0.08, Control: 0.05±0.05, p<0.05) (FIG. 26C). The differences were recorded regarding fed or fasted levels of insulin or glucose (FIG. 26D), or following a GTT performed after 5 weeks of chronic injection (FIG. 27B). A significant reduction in the HOMA-IR index was recorded in LITA injected animals, suggesting improved insulin sensitivity (LITA: 1.9±1.4; Control: 3.6±1.5, p=0.03). Serum inflammatory markers resistin and TNF-α were significantly reduced in mice that received LITA injection (Resistin: LITA: 13.6±1.8 ng/ml, Control: 17.2±4.8 ng/ml, p<0.05; TNF-α: LITA: 14.8±8.5 pg/ml, Control: 46.9±33.1 pg/ml, p<0.01). Serum levels of triglycerides (LITA: 0.79±0.09 mmol/L, Control: 1.03±0.22 mmol/L, p=0.05) (FIG. 26E) and leptin (LITA: 1921±935 pg/ml, Control: 2889±1209 pg/ml, p<0.001) (FIG. 27C) were also significantly decreased in LITA injected animals, with no differences in cholesterol, HDL or LDL (FIG. 26E). WAT and mesenteric AT were significantly reduced following LITA administration (WAT: LITA: 1.36±0.24 g, Control: 1.5±0.17 g, p<0.05; mesenteric: LITA: 0.16±0.04 g, Control: 0.19±0.01 g, p<0.05) (FIG. 27D). Isolated adipocytes from epididymal and subcutaneous depots were recorded in mean number, volume or surface area between groups. AT isolated from LITA-injected animals demonstrated reduced expression of hormone sensitive lipase (HSL) mRNA (Fold change compared to control: 0.05±0.08, p<0.001) (FIG. 26F), reflecting reduced mobilisation of peripheral lipids. Similar to the results of the preventative HFD model, quantitative RT-PCR of liver mRNA samples revealed a LITA-induced reduction in expression of genes involved in VLDL metabolism (Apo-B, Mttp), β-oxidation (ACOX-1, CPT-1), mitochondrial oxidation (PPARγ, PGC-1), glucose metabolism (GLUT-2, IRS-1, IRS-2) and inflammation (TNFα) (FIG. 26G). Histological examination revealed normal liver architecture for all mice on a NFD, with LITA injected mice revealing less microvacuolation than controls (FIG. 26H), indicative of reduced inflammation. Mitochondrial oxidative phosphorylation complex activity were compared between groups (FIG. 25E).

Example 16

Metabolic Effects of LITA Nanoparticle Administration on Xenograft Tumour Metastasis The administration of LITA nanoparticles (Example 2) led to a significant reduction in tumour size (LITA: 107±113 mm2, Control: 270±87 mm2, p=0.04) (FIG. 28A-C). Progression of tumour volume was significantly reduced in LITA injected animals (Tumour volume (week 4): LITA: 123±119 mm3, Control: 254±93 mm3, p<0.05) (FIG. 28D). Quantitative RT-PCR of xenograft mRNA revealed a significant decrease in expression of Class I HDACs; HDAC 1 (p<0.05), HDAC 2 (p<0.05), HDAC 3 (p<0.001) and HDAC 4 (p<0.01) in LITA injected animals (FIG. 28E). In addition, the expression of "silent mating type information regulation homologues" or SirT proteins, responsible for epigenetic silencing mRNA, was also significantly reduced in LITA injected animals (SirT1, p<0.05) (FIG. 28E).

Example 17

Effects of Nanoparticles on a Rat MCAO Model of Stroke

The potential effectiveness of the nanoparticles of Example 2 (encapsulating acetate) for the protection and recovery of brain tissue following stroke were tested on a mid-cerebral artery occlusion (MCAO) rat model.

Methods

Animals: Sprague-Dawley rats (male, 230-250 g, n=20 Harlan) were obtained and allowed to acclimatise for 5-7 days prior to induction of mid-cerebral artery occlusion (MCAO). They were randomly allocated to two groups with similar body weights.

Induction of stroke: Prior to induction of MCAO, neuroscore was performed (see below). For induction of MCAO, rats were anaesthesized with 2% isoflurane, oxygen-air mix (30:70). A midline incision was made to expose the common carotid artery and a blood sample taken from the jugular vein and plasma obtained (see below). A 5-0 monofilament nylon suture with a silicone rubber coated tip (0.33 mm diameter, 4-5 mm long) was introduced into the internal carotid artery and advanced 20-22 mm along the artery to obstruct blood flow to the mid-cerebral artery (MCA). An intraperitoneal (ip) injection of vehicle or treatment (1 ml) was given at occlusion. Animals were then allowed to recover from anaesthesia during MCAO. After 90 mins of MCAO, animals were anaesthetised and the filament was retracted completed to allow reperfusion of the MCA. Saline (3 ml) was given subcutaneously to attenuate possible dehydration. Body temperature was maintained using a heating blanket and a rectal probe during surgery.

Animals were given an intraperitoneal dose of either control nanoparticles (1 ml) or nanoparticles according to Example 2 (1 ml) daily for the 2 week observation period. Body weights and neuroscores were also recorded daily throughout the experimental period.

Assessment of Treatment: Magnetic resonance imaging (MRI) was performed at 24 h and 2 weeks post-occlusion. 1H magnetic resonance spectroscopy (MRS) of the striatum was also performed at the latter time-point (see below). Prior to MRI and MRS at the final timepoint, open field was also performed to assess the locomotor activity of the rats.

After MRI and MRS at the final time-point, the brains were perfusion-fixed with 4% paraformaldehyde (PFA, phosphate-buffered saline (PBS), see below). After perfusion, the brains were harvested and allowed to fix further in 4% PFA for a week prior to placement in 30% sucrose (PBS) for subsequent cryosectioning and immunofluorescence.

Magnetic resonance methods: Rats were anaesthetized with isoflurane, oxygen-air (30:70%) mix. The rat head was carefully located centrally in a 43 mm inner diameter quadrature volume MRI coil and then placed within the magnet bore of a 7 T Agilent MR scanner. T2-weighted MRI was performed at 24 h, 1 week and 2 weeks post-occlusion to show the size and extent of the MCAO lesion. Lesion volumes on the T2-weighted MR images were manually segmented.

Behavious—Neuroscore—Open field: The open field test was performed to evaluate locomotor activity and anxiety-like behaviour. Behavioural testing was carried out in a quiet and dimly lit behaviour room in white, featureless arenas. Rats were individually placed in the arena and their behaviour was recorded for 30 minutes via a video camera positioned on the ceiling, directly above the arenas. The total distance covered by the rat and the average speed was measured using EthoVision XT software (Noldus, Wageningen, Netherlands). After the end of the recording, animals were returned to their cages and the arenas were thoroughly cleaned with 70% IMS solution between each set of animals.

Results

MRI-Assessment of Lesion Volumes: Lesion volumes, as assessed by MRI, were smaller in rats treated with nanoparticles of Example 2 24 h post-occlusion compared to controls (91.33±24.63 mm$^3$ vs 143.4±44.1). At 1 week post-occlusion, lesions were decreased in both groups (FIG. 29) from that at 24 h post-occlusion.

Behaviour Assessment—Open field: Rats given nanoparticles of Example 2 travelled greater distances (P<0.05) and at greater speed (P<0.05) than those given the control-nanoparticle on occlusion (FIG. 30).

SUMMARY

These results indicate that nanoparticle encapsulated acetate acts as a potent multifunctional active pharmaceutical ingredient (API), capable of preventing and reversing the development of pathogenic signatures indicative of both obesity and cancer. Assessment of the bio-distribution of 18F-FDG, rhodamine and gadolinium conjugated liposomes using histology and imaging confirmed that LITA nanoparticles are naturally livertropic. In particular, the increased molarity percentage of DSPE-PEG$^{2000}$ in the liposome membrane led to preferential accumulation of liposomes in tumour tissue.

In all dietary models examined, chronic LITA administration significantly reduced intrahepatocellular lipids (IHCL) and adiposity in both reparative and preventative HFD paradigms. These changes occurred independently of reduced food intake or body weight. Importantly, more than merely slowing accumulation, LITA delivery actively reduced IHCL. Hepatic lipid accumulation represents a key intermediary in a succession of increasingly debilitating liver conditions and is strongly associated with the development of insulin resistance and diabetes. The LITA-induced reduction in IHCL suggests the nanoparticle is not only capable of preventing NAFLD, but may also modulate subsequent progression to hepatocellular carcinoma (HCC). LITA injection was found to reduce circulating levels of FFA and triglycerides, in HFD and NFD models respectively. Data indicating LITA administration decreases the expression of proteins involved in peripheral mobilisation of lipids, hepatic lipogenesis and lipid uptake, provides a prospective mechanism for the robust reduction in IHCL. In addition to reductions in adiposity and IHCL, investigation of liver function revealed additional beneficial effects. The reduction in UCP-2 expression, observed in both HFD and NFD models, reflects reduced proton leakage across the mitochondrial membrane, less disruption in electrochemical potential and increased organelle efficiency. The trend toward an increase in the number of cristae per perimeter length and increased protein expression of OXPHOS complexes in HFD model, indicate increased ATP production. Furthermore, the LITA-induced reduction in serum AST and ALP, indicated improved function.

LITA delivery led to reduced expression of TNF-α in liver in both NFD and HFD models, with a trend towards lower serum concentrations of TNF-α, IL-6 and resistin. Furthermore, were LITA administration to continue, the reductions in fat mass and IHCL observed in all dietary paradigms would be expected to contribute to an additional long-term improvement in inflammatory tone. The changes following LITA administration were not consistent across all dietary models, with reductions in fatty acid synthesis, circulating FFA, insulin and serum markers of inflammation and liver function, limited to HFD paradigms. Under normal dietary conditions increased hepatic acetate is associated with upregulation of fatty acid oxidation found during prolonged fasting. It is conceivable that compensatory homeostatic mechanisms interpreting the elevated level of hepatic acetate as a starvation signal led to the muted metabolic response to LITA administration on a NFD background.

Acetate supplementation leads to increased production of acetyl Co-A in the liver, which following mitochondrial uptake, can enter either the TCA cycle, increasing ATP production as observed in cell culture in the HFD model, or enter ketogenic pathways, as seen in the preventative HFD model. As ketogenesis occurs exclusively in liver mitochondrion, the LITA-induced increase in serum hydroxybutyrate is an important finding, indirectly confirming in vivo delivery of acetate to hepatic mitochondria. Given the apparent absence of expression of mitochondrial acetyl-CoA synthetase (AceCS2) in the liver, it is conceivable that acetate from LITA nanoparticles is converted to acetyl-CoA by the cytosolic enzyme (AceCS1), which subsequently enters the mitochondria. However, the data indicates the reverse, with chronic LITA injection reducing expression of genes controlling β-oxidative pathways in both NFD and HFD models. The manner and rate of acetate metabolism may account for these differences, with the comparatively stable and predominantly hepatic delivery afforded by liposomal nanoparticles, contrasting with the more immediate, global uptake following bolus injection or oral gavage.

Together, the results support a mechanism by which LITA-induced mitochondrial accumulation of acetyl-CoA, inhibits β-oxidation subsequently reducing lipid uptake, lipogenesis and hepatic uptake. Furthermore, these changes are consistent with the hypothesis that availability of acetate as a fuel generates metabolic signals that impair use of glucose through inhibition of glycolytic and gluconeogenic pathways. A shift away from carbohydrate metabolism might be expected to result in altered respiratory outcomes in LITA-injected animals yet no differences were observed following metabolic cage analysis. However, these results are supported by several publications reporting that energy expenditure is maintained following acetate infusion, since acetate replaces fat as an oxidative fuel.

The anti-tumorigenic effects attributed to SCFAs have been linked to changes in expression of HDAC enzymes, epigenetic markers that play a key role in cellular gene expression. The ineffectual metabolism of SCFA in cancer cells is thought to lead to the accumulation of acetyl-CoA in the nucleus, where it functions as an HDAC inhibitor altering the expression of genes involved in cellular proliferation, apoptosis, and differentiation. While previous studies have attempted to target and disrupt the altered cellular metabolism in colonic cancer cells via supplementation with the SCFA, butyrate, these results support this hypothesis; chronic administration of LITA led to significant reduced tumour growth and decreased mRNA expression in several classes of HDACs. Thus, it is predicted that LITA supplementation induces a switch in fuel selection, from aerobic glycolysis to mitochondrial beta-oxidation, representing a metabolic reprogramming of cancer cells towards a normal, non-proliferative state. The decreased expression of the histone deacetylase, SirT1, is of note given its role as an inhibitor of apoptosis and promoter for tumorigenesis.

Overall, LITA administration resulted in a comprehensive improvement in metabolic profile in animal models of both obesity and cancer; including reductions in tumour growth and amelioration of a wide range of metabolic syndrome associated outcomes, including reductions in IHCL, body fat, serum insulin, FFA and inflammatory tone. Administration has also proved valuable in a stroke model.

The invention claimed is:

1. A cationic liposomal nanoparticle for the delivery of one or more short-chain fatty acid therapeutic agents consisting of:

i) a cationic cholesterol derivative;
ii) a neutral phospholipid;
iii) cholesterol or a neutral cholesterol derivative;
iv) a neutral saturated fatty acid derivative of phosphatidylethanolamine or phosphatidylcholine, which derivative is PEGylated; and
v) a therapeutic agent consisting of a short-chain fatty acid;
vi) optionally aqueous 4-2-(hydroxyethyl)-1-piperazineethanesulfonic acid (HEPES) buffer;
vii) optionally NaCl;
viii) optionally a tumour targeting agent;
ix) optionally a fluorescent phospholipid;
x) optionally one or more lipids for improving magnetic resonance imaging or nuclear magnetic resonance imaging;
wherein the short chain fatty acid therapeutic agent is encapsulated within the nanoparticle.

2. The nanoparticle according to claim 1, wherein the short-claim fatty acid is selected from the group consisting of acetic acid, propionic acid, and butyric acid.

3. The nanoparticle according to claim 2, wherein the short-chain fatty acid is acetic acid.

4. The nanoparticle according to claim 1, sized in the range of 1 to 500 nm or 40-120 nm.

5. The nanoparticle according to claim 1, wherein the concentration of encapsulated therapeutic agent is in the range of 0.1 to 20mM or wherein the concentration of encapsulated therapeutic agent is in the range of 1 to 10 mM.

6. The nanoparticle according to claim 1, wherein the cationic cholesterol derivative is a cholesterol derivative having a polyamine hydrocarbon appendage wherein the polyamine appendage is optionally of the formula: $H_2N(CH_2)_xNH(CH_2)_yNH(CH_2)_zNHC(O)-$, wherein x is 1 to 10, y is 1 to 10, and z is 1 to 10.

7. The nanoparticle according to claim 1, wherein the neutral phospholipid is a saturated neutral phospholipid or wherein the neutral phospholipid is a phosphatidylcholine or phosphatidylethanolamine phospholipid.

8. The nanoparticle according to claim 1, wherein the neutral saturated fatty acid derivative of phosphatidylethanolamine or phosphatidylcholine, which derivative is PEGylated, comprises saturated fatty acid chains of $C_{12}$-20 or has a polyethylene glycol chain with a molecular weight of at least 100 or at least 1000.

9. The nanoparticle according to claim 1, wherein the molar ratio range of elements (i) to (iv) satisfies the following ranges:
(i) 20 to 40;
(ii) 20 to 40;
(iii) 25 to 55; and
(iv) 1 to 10, respectively.

10. The nanoparticle according to claim 1, wherein the tumour targeting agent is present and is a ligand for a receptor that is overexpressed in tumour cells relative to the expression of said receptors in the cells of non-tumourous tissue of mammals.

11. The nanoparticle according to claim 10, wherein the tumour targeting agent has a folate moiety, or wherein the tumour targeting agent is a phospholipid-polyethylene glycol-folate compound or tumour targeting agent is DSPE-PEG(2000)—Folate [distearoylphosphatidylethanolamine-polyethylene glycol (2000)—folate].

12. The nanoparticle according to claim 11, wherein the amount of the folate moiety present in the formulation is 1-2mol % of the total formulation.

* * * * *